US011155576B2

(12) United States Patent
Xu et al.

(10) Patent No.: US 11,155,576 B2
(45) Date of Patent: Oct. 26, 2021

(54) SYNTHETIC PEPTIDES, ENZYMATIC FORMATION OF PERICELLULAR HYDROGELS/NANOFIBRILS, AND METHODS OF USE

(71) Applicant: BRANDEIS UNIVERSITY, Waltham, MA (US)

(72) Inventors: Bing Xu, Newton, MA (US); Junfeng Shi, Waltham, MA (US); Yi Kuang, Kyoto (JP)

(73) Assignee: BRANDEIS UNIVERSITY, Waltham, MA (US)

( * ) Notice: Subject to any disclaimer, the term of this patent is extended or adjusted under 35 U.S.C. 154(b) by 637 days.

(21) Appl. No.: 15/303,172

(22) PCT Filed: Apr. 9, 2015

(86) PCT No.: PCT/US2015/025149
§ 371 (c)(1),
(2) Date: Mar. 6, 2018

(87) PCT Pub. No.: WO2015/157535
PCT Pub. Date: Oct. 15, 2015

(65) Prior Publication Data
US 2017/0037082 A1    Feb. 9, 2017

Related U.S. Application Data

(60) Provisional application No. 61/977,484, filed on Apr. 9, 2014, provisional application No. 62/105,871, filed on Jan. 21, 2015.

(51) Int. Cl.
| | | |
|---|---|---|
| *C07K 5/087* | (2006.01) | |
| *C07K 5/107* | (2006.01) | |
| *A61K 49/00* | (2006.01) | |
| *G01N 33/58* | (2006.01) | |
| *C07K 14/00* | (2006.01) | |
| *C07K 5/103* | (2006.01) | |
| *C07K 5/065* | (2006.01) | |
| *G01N 33/573* | (2006.01) | |

(52) U.S. Cl.
CPC ........ *C07K 5/0812* (2013.01); *A61K 49/0056* (2013.01); *C07K 5/06078* (2013.01); *C07K 5/1013* (2013.01); *C07K 5/1016* (2013.01); *C07K 14/001* (2013.01); *G01N 33/573* (2013.01); *G01N 33/582* (2013.01)

(58) Field of Classification Search
CPC ...... C07K 5/0812; C07K 5/1016; C07K 7/00; C07K 7/12; C07K 5/08; C07K 5/10
See application file for complete search history.

(56) References Cited

U.S. PATENT DOCUMENTS
| | | | | |
|---|---|---|---|---|
| 2010/0093084 A1* | 4/2010 | Xu | ............................ | B82Y 5/00 435/375 |
| 2012/0142616 A1 | 6/2012 | Gao et al. | | |
| 2014/0148410 A1 | 5/2014 | Xu | | |

FOREIGN PATENT DOCUMENTS
| | | | | |
|---|---|---|---|---|
| WO | 2010/151644 A2 | 12/2010 | | |
| WO | 2010/166705 A2 | 12/2012 | | |
| WO | 2012/166706 A2 | 12/2012 | | |
| WO | WO-2012166706 A2 * | 12/2012 | ........... | C07D 239/47 |
| WO | 2014/138367 A1 | 9/2014 | | |
| WO | 2015157535 A2 | 10/2015 | | |

OTHER PUBLICATIONS

Sato et al. "Hela Cells Consists of Two Cell Types, as Evidenced by Cytochemical Staining for Alkaline Phosphatase Activity: A Possible Model for Cancer Stem Cell Study", Advances in Stem Cells, 2013, 15 pages (Year: 2013).*
Yang et al., "Intracellular Hydrogelation of Small Molecules Inhibits Bacterial Growth", Angew. Chem. Int. Ed., 2007, pp. 8216-8219 (Year: 2007).*
Yang et al., ntracellular Enzymatic Formation of Nanofibers Results in Hydrogelation and Regulated Cell Death, Advanced Materials, 2007, pp. 3152-3156 (Year: 2007).*
Abaan et al., "The Exomes of the NCI-60 Panel: A Genomic Resource for Cancer Biology and Systems Pharmacology," 73(14):4372-82 (2013).
Gao et al., "Imaging Enzyme-Triggered Self-Assembly of Small Molecules Inside Live Cells," Nat. Commun. 3:1033 (2012).
International Search Report and Written Opinion for corresponding Application No. PCT/US2015/025149 (dated Oct. 16, 2015).
Wang et al., "A Structure-Gelatin Ability Study in a Short Peptide-Based 'Super Hydrogelator' System," Soft Matter 7:3897-3905 (2011).

(Continued)

*Primary Examiner* — Lianko G Garyu
(74) *Attorney, Agent, or Firm* — Troutman Pepper Hamilton Sanders LLP (Rochester)

(57) ABSTRACT

Disclosed are peptides that contain up to about 35 amino acids, including a plurality of aromatic amino acid residues and either (i) an amino acid residue that is phosphorylated or sulfated, or (ii) an amino acid comprising an ester-moiety linked via peptide bond, or both (i) and (ii), wherein the peptide is capable of self-assembly to form nanofibrils in the presence of an enzyme that hydrolyzes the phosphate group, the sulfate group, or the ester-moiety. These peptides are enzymatically responsive hydrogelators, and they can be used to form pericellular hydrogels/nanofibrils upon exposure to target cells that secrete or express a surface bound ectoenzyme having hydrolase activity suitable to induce peptide gelation. These materials, and compositions containing the same, can be used for in vitro and in vivo cellular imaging, treating cancerous conditions, collecting a secretome from a cell upon which the pericellular hydrogels/nanofibrils form, and screening the collected secretome.

13 Claims, 31 Drawing Sheets
(4 of 31 Drawing Sheet(s) Filed in Color)

Specification includes a Sequence Listing.

(56) References Cited

OTHER PUBLICATIONS

Yang et al., "Intracellular Enzymatic Formation of Nanofibers Results in Hydrogelation and Regulated Cell Death," Adv, Mater. 19:3152-6 (2007).
Yang et al., "Intracellular Hydrogelation of Small Molecules Inhibits Bacterial Growth," 46:8216-9 (2007).
Zhou et al., "Aromatic-Aromatic Interactions Enhance Interfiber Contacts for Enzymatic Formation of a Spontaneously Aligned Supramolecular Hydrogel," J. Am. Chem. Soc. 136(8):2970-3 (2014).
Ikeda et al., "Three-Dimensional Encapsulation of Live Cells by Using a Hybrid Matrix of Nanoparticles in a Supramolecular Hydrogel," Chemistry A European Journal 14:10808-10815 (2008).
Zhang et al., "Versatile Small Molecule Motifs for Self-Assembly in Water and Formation of Biofunctional Supramolecular Hydrogels," Langmuir. 27(2):529-37 (2011).

\* cited by examiner

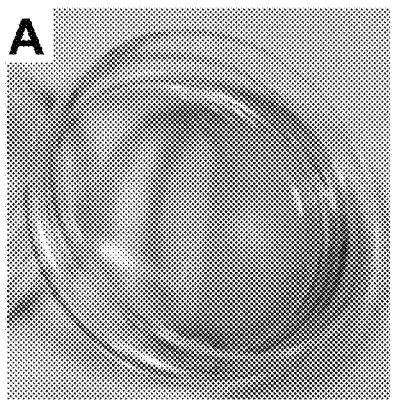 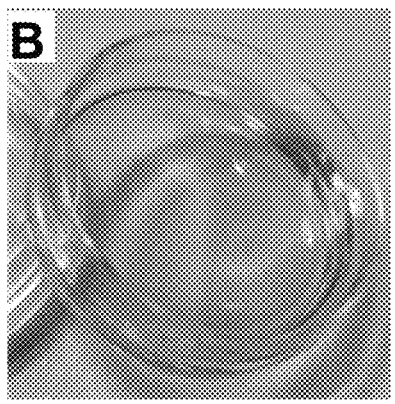
FIGS. 5A-5B
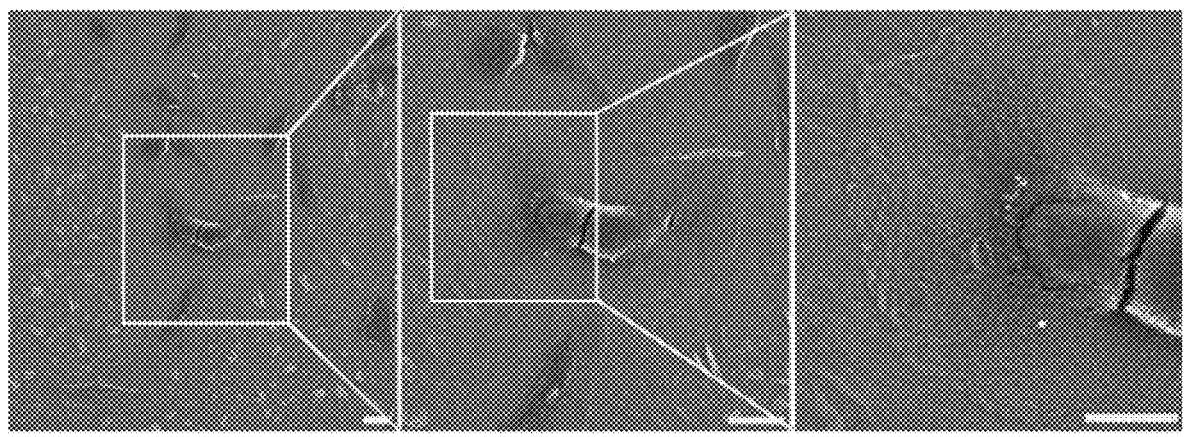
FIG. 6
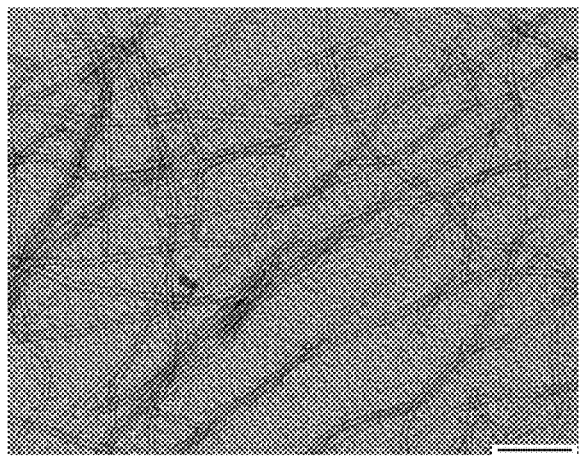 
FIG. 7     FIG. 8

FIGS. 32A-C

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: Naphthylalanine
<222> LOCATION: (1)..(1)
<223> OTHER INFORMATION: Xaa at position 1 is Naphthylalanine modified
      with an N-terminal (7-nitro-1, 2, 5-benzoxadiazolyl amino)
```

-continued

```
      propionyl group
<220> FEATURE:
<221> NAME/KEY: MOD_RES
<222> LOCATION: (4)..(4)
<223> OTHER INFORMATION: PHOSPHORYLATION

<400> SEQUENCE: 1

Xaa Phe Phe Tyr
1

<210> SEQ ID NO 2
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: Naphthylalanine
<222> LOCATION: (1)..(1)
<223> OTHER INFORMATION: Xaa at position 1 is Naphthylalanine modified
      with an N-terminal (7-nitro-1, 2, 5-benzoxadiazolyl amino)
      propionyl group
<220> FEATURE:
<221> NAME/KEY: Naphthylalanine
<222> LOCATION: (2)..(2)
<223> OTHER INFORMATION: Xaa at position 2 is Naphthylalanine
<220> FEATURE:
<221> NAME/KEY: MOD_RES
<222> LOCATION: (4)..(4)
<223> OTHER INFORMATION: PHOSPHORYLATION

<400> SEQUENCE: 2

Xaa Xaa Phe Tyr
1

<210> SEQ ID NO 3
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: Naphthylalanine
<222> LOCATION: (1)..(1)
<223> OTHER INFORMATION: Xaa at position 1 is Naphthylalanine modified
      with an N-terminal (7-nitro-1, 2, 5-benzoxadiazolyl amino)
      propionyl group
<220> FEATURE:
<221> NAME/KEY: CARBOHYD
<222> LOCATION: (4)..(4)
<223> OTHER INFORMATION: CARBOHYD is D-glucosamine residue at C-terminus
<220> FEATURE:
<221> NAME/KEY: MOD_RES
<222> LOCATION: (4)..(4)
<223> OTHER INFORMATION: PHOSPHORYLATION

<400> SEQUENCE: 3

Xaa Phe Phe Tyr
1

<210> SEQ ID NO 4
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MOD_RES
<222> LOCATION: (1)..(1)
<223> OTHER INFORMATION: ACETYLATION
<220> FEATURE:
<221> NAME/KEY: Naphthylalanine
<222> LOCATION: (3)..(4)
```

```
<223> OTHER INFORMATION: Xaa at positions 3-4 is Naphthylalanine
<220> FEATURE:
<221> NAME/KEY: MOD_RES
<222> LOCATION: (5)..(5)
<223> OTHER INFORMATION: PHOSPHORYLATION

<400> SEQUENCE: 4

Met Leu Xaa Xaa Tyr
1               5

<210> SEQ ID NO 5
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: Naphthylalanine
<222> LOCATION: (1)..(1)
<223> OTHER INFORMATION: Xaa at position 1 is Naphthylalanine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: 3- amino phenyl boronic acid group is attached
      to C-terminus
<220> FEATURE:
<221> NAME/KEY: MOD_RES
<222> LOCATION: (4)..(4)
<223> OTHER INFORMATION: PHOSPHORYLATION

<400> SEQUENCE: 5

Xaa Phe Phe Tyr
1

<210> SEQ ID NO 6
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MOD_RES
<222> LOCATION: (1)..(1)
<223> OTHER INFORMATION: FORMYLATION
<220> FEATURE:
<221> NAME/KEY: Naphthylalanine
<222> LOCATION: (3)..(4)
<223> OTHER INFORMATION: Xaa at positions 3-4 is Naphthylalanine
<220> FEATURE:
<221> NAME/KEY: MOD_RES
<222> LOCATION: (5)..(5)
<223> OTHER INFORMATION: PHOSPHORYLATION

<400> SEQUENCE: 6

Met Leu Xaa Xaa Tyr
1               5

<210> SEQ ID NO 7
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: Naphthylalanine
<222> LOCATION: (1)..(1)
<223> OTHER INFORMATION: Xaa at position 1 is Naphthylalanine
<220> FEATURE:
<221> NAME/KEY: MOD_RES
```

```
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: 3-amino phenyl boronic acid group is attached
      to C-terminus
<220> FEATURE:
<221> NAME/KEY: MOD_RES
<222> LOCATION: (4)..(4)
<223> OTHER INFORMATION: PHOSPHORYLATION

<400> SEQUENCE: 7

Xaa Phe Phe Tyr
1

<210> SEQ ID NO 8
<211> LENGTH: 4
<212> TYPE: PRT
<213> ORGANISM: Artificial
<220> FEATURE:
<223> OTHER INFORMATION: Derivative hydrogelator
<220> FEATURE:
<221> NAME/KEY: Naphthylalanine
<222> LOCATION: (1)..(1)
<223> OTHER INFORMATION: Xaa at position 1 is Naphthylalanine modified
      with an N-terminal (7-nitro-1, 2, 5-benzoxadiazolyl amino)
      propionyl group

<400> SEQUENCE: 8

Xaa Phe Phe Tyr
1

<210> SEQ ID NO 9
<211> LENGTH: 4
<212> TYPE: PRT
<213> ORGANISM: Artificial
<220> FEATURE:
<223> OTHER INFORMATION: Derivative hydrogelator
<220> FEATURE:
<221> NAME/KEY: Naphthylalanine
<222> LOCATION: (1)..(1)
<223> OTHER INFORMATION: Xaa at position 1 is Naphthylalanine modified
      with an N-terminal (7-nitro-1, 2, 5-benzoxadiazolyl amino)
      propionyl group
<220> FEATURE:
<221> NAME/KEY: Naphthylalanine
<222> LOCATION: (2)..(2)
<223> OTHER INFORMATION: Xaa at position 2 is Naphthylalanine

<400> SEQUENCE: 9

Xaa Xaa Phe Tyr
1

<210> SEQ ID NO 10
<211> LENGTH: 4
<212> TYPE: PRT
<213> ORGANISM: Artificial
<220> FEATURE:
<223> OTHER INFORMATION: Derivative hydrogelator
<220> FEATURE:
<221> NAME/KEY: Naphthylalanine
<222> LOCATION: (1)..(1)
<223> OTHER INFORMATION: Xaa at position 1 is Naphthylalanine modified
      with an N-terminal (7-nitro-1, 2, 5-benzoxadiazolyl amino)
      propionyl group
<220> FEATURE:
<221> NAME/KEY: CARBOHYD
<222> LOCATION: (4)..(4)
<223> OTHER INFORMATION: CARBOHYD is D-glucosamine residue at C-terminus

<400> SEQUENCE: 10
```

```
Xaa Phe Phe Tyr
1

<210> SEQ ID NO 11
<211> LENGTH: 5
<212> TYPE: PRT
<213> ORGANISM: Artificial
<220> FEATURE:
<223> OTHER INFORMATION: Derivative hydrogelator
<220> FEATURE:
<221> NAME/KEY: MOD_RES
<222> LOCATION: (1)..(1)
<223> OTHER INFORMATION: ACETYLATION
<220> FEATURE:
<221> NAME/KEY: Naphthylalanine
<222> LOCATION: (3)..(4)
<223> OTHER INFORMATION: Xaa at positions 3-4 is Naphthylalanine

<400> SEQUENCE: 11

Met Leu Xaa Xaa Tyr
1               5

<210> SEQ ID NO 12
<211> LENGTH: 4
<212> TYPE: PRT
<213> ORGANISM: Artificial
<220> FEATURE:
<223> OTHER INFORMATION: Derivative hydrogelator
<220> FEATURE:
<221> NAME/KEY: Naphthylalanine
<222> LOCATION: (1)..(1)
<223> OTHER INFORMATION: Xaa at position 1 is Naphthylalanine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: 3-amino phenyl boronic acid group is attached
      to C-terminus

<400> SEQUENCE: 12

Xaa Phe Phe Tyr
1
```

SYNTHETIC PEPTIDES, ENZYMATIC FORMATION OF PERICELLULAR HYDROGELS/NANOFIBRILS, AND METHODS OF USE

This application is a national stage application under 35 U.S.C. § 371 of PCT Application No. PCT/US2015/025149, filed Apr. 9, 2015, which claims the priority benefit of U.S. Provisional Patent Application Serial Nos. 61/977,484 filed Apr. 9, 2014, and 62/105,871 filed Jan. 21, 2015, each of which is hereby incorporated by reference in its entirety.

This invention was made with government support under R01CA142746 awarded by National Institutes of Health and DMR0820492 awarded by National Science Foundation. The government has certain rights in the invention.

FIELD OF THE INVENTION

The present invention relates generally to enzymatically responsive peptide hydrogelator precursors, the enzymatically activated hydrogelators and hydrogels formed therefrom, and use of the precursors to form pericellular hydrogels/nanofibrils upon exposure to target cells that secrete or express a surface bound ectoenzyme having hydrolase activity suitable to induce peptide gelation. These materials, and compositions containing the same, can be used for in vitro and in vivo cellular imaging, treating cancerous conditions, collecting a secretome from a cell upon which the pericellular hydrogels/nanofibrils form as well as screening the collected secretome.

BACKGROUND OF THE INVENTION

Cancer remains a major challenge to public health. The estimated new cases and deaths from cancer in the United States in 2013 were 1,660,290 and 583,350, respectively (American Cancer Society, *Cancer Facts & Figures* 2013: Atlanta: American Cancer Society; 2013). Conventional cancer chemotherapy has been largely unable to meet the challenge posed by the great complexity of cancer cells (Hanahan et al., "The Hallmarks of Cancer," *Cell* 100:57 (2000); Hanahan et al., "Hallmarks of Cancer: The Next Generation," *Cell* 144:646 (2011); Doroshow, "Overcoming Resistance to Targeted Anticancer Drugs," *N Engl J Med* 369:1852 (2013)) that causes cancer drug resistance (Hanahan et al., "Hallmarks of Cancer: The Next Generation," *Cell* 144:646 (2011); Holohan et al., "Cancer Drug Resistance: An Evolving Paradigm," *Nat Rev Cancer* 13:714 (2013)) and metastasis (Hanahan et al., "Hallmarks of Cancer: The Next Generation," *Cell* 144:646 (2011); Gupta et al., "Cancer Metastasis: Building a Framework," *Cell* 127:679 (2006)). Therefore, it is imperative to develop innovative approaches that differ drastically from the conventional ones for overcoming cancer drug resistance.

The present invention overcomes these and other deficiencies in the art.

SUMMARY OF THE INVENTION

A first aspect of the invention relates to a peptide comprising up to about 35 amino acids, including a plurality of aromatic amino acid residues and either (i) an amino acid residue that is phosphorylated or sulfated, or (ii) an amino acid comprising a covalently bonded ester-moiety, or both (i) and (ii), wherein, upon exposure to a cell that expresses an ectoenzyme that hydrolyzes the phosphate group, the sulfate group, or the ester-moiety, the peptide self-assembles to form nanofibrils externally of the cell. In certain embodiments, the peptide includes a fluorophore conjugated to the peptide.

Also encompassed by this aspect of the invention are enzymatically activated peptides, which are either (i) dephosphorylated or desulfated, (ii) comprising a carboxylic acid residues at the site of hydrolytic ester cleavage, or both (i) and (ii); and supramolecular hydrogels formed upon self-assembly of the enzymatically activated peptides.

A second aspect of the invention relates to a pharmaceutical composition comprising a pharmaceutically acceptable carrier and a peptide according to the first aspect of the invention. One or more structurally distinct peptides can be included in the composition.

A third aspect of the invention relates to a method for forming a nanofibril network on or near the surface of target cells. This method involves contacting a target cell that expresses a cell surface-bound enzyme having hydrolytic (hydrolase) activity, secretes an enzyme having hydrolytic (hydrolase) activity, or both, with the peptide according to the first aspect of the invention or the pharmaceutical composition according to the second aspect of the invention, wherein said contacting is effective to hydrolyze the phosphate group, the sulfate group, or the ester-moiety and cause in situ self-assembly of the peptides to form a nanofibril network on or near the surface of the target cell.

A fourth aspect of the invention relates to a method for collecting a target cell secretome. This method involves contacting a target cell that expresses a cell surface-bound enzyme having hydrolytic (hydrolase) activity, secretes an enzyme having hydrolytic (hydrolase) activity, or both, with a peptide according to the first aspect of the invention or the pharmaceutical composition according to the second aspect of the invention, wherein said contacting is effective to hydrolyze the phosphate group, the sulfate group, or the ester-moiety and cause in situ self-assembly of the peptide to form a nanofibril network on or near the surface of the target cells, whereby the nanofibril network retains the target cell secretome from the pericellular space of the target cell; separating the target cell secretome from the nanofibril network; and collecting the separated target cell secretome.

A fifth aspect of the invention relates to a method for screening a target cell secretome. This method involves collecting the separated target cell secretome according to the fourth aspect of the invention; and analyzing the target cell secretome.

A sixth aspect of the invention relates to a method for treating a cancerous condition in a subject. This method involves administering to a subject having a cancerous condition a therapeutically effective amount of the peptide according to the first aspect of the invention or the pharmaceutical composition according to the second aspect of the invention, wherein said administering is effective to hydrolyze the phosphate group, the sulfate group, or the ester moiety and cause in vivo self-assembly of the peptides to form a nanofibril network on or near the surface of cancer cells.

A seventh aspect of the invention relates to a method of in vivo imaging. This method comprises administering to a subject a diagnostically effective amount of the peptide according to the first aspect of the invention or the pharmaceutical compositions according to the second aspect of the invention, wherein the peptide includes a fluorophore or contrasting agent, and wherein said administering is effective to cause in vivo self-assembly of the peptides to form a nanofibril network on or near the surface of the target cells; and imaging the nanofibril network.

An eighth aspect of the invention relates to a method of in vitro imaging. This method involves contacting a target cell with a diagnostically effective amount of the peptide according to the first aspect of the invention or the pharmaceutical compositions according to the second aspect of the invention, wherein the peptide includes a fluorophore, and wherein said contacting causes the in vitro self-assembly of the peptide to form a nanofibril network on or near the surface of target cells, and imaging the nanofibril network to identify the target cell.

A ninth aspect of the invention relates to an in vitro screening method for inhibitors of ectoenzymes. This method involves incubating a cell population comprising target cells with a compound, imaging the cell population according to the eighth aspect of the invention and measuring fluorescence of the nanofibril network on or near the surface of target cells, and identifying compounds which decrease fluorescence of the target cells compared to target cells exposed to the peptide or composition but untreated by the compound.

The accompanying Examples demonstrate the unexpected observation of the selective formation of nanonets/hydrogels of small D-peptide derivatives in the pericellular space of cancer cells. As demonstrated in the accompanying Examples, enzyme-catalyzed molecular nanofibers: (i) form selectively on target cells that express an ectoenzyme; (ii) inhibit target cell migration, target cell survival, target cell growth, and the passage of intracellular signaling molecules to or from the target cell; (iii) enable the enzyme-catalyzed imaging of target cells; and (iv) enable the collection of target cell secretomes. Importantly, enzymatic formation of molecular nanofibrils inhibits survival of drug-resistant cancer cells. These unprecedented phenomena imply that the mechanisms of action of the molecular nanofibers significantly depart from the well-established ligand-receptor dogma of current anticancer drugs. Thus, use of the molecular nanofibers as a nanomedicine promises to overcome cancer drug resistance.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIGS. 1A-1B illustrate the hydrogelator D-2b and its precursor D-2a. FIG. 1A shows the enzyme catalyzed formation of pericellular hydrogel/nanonets to induce cell death. FIG. 1B illustrates the molecular structures of the precursor D-2a and the hydrogelator D-2b.

FIGS. 2A-2D are optical images of HeLa cells incubated with 560 µM D-2a (FIG. 2A), 280 µM D-2a (FIG. 2B), 140 µM D-2a (FIG. 2C), or 560 µM D-2b (FIG. 2D) for two hours. FIG. 2E is a series of scanning electron microscopy ("SEM") images of the pericellular hydrogels on HeLa cells treated with 560 µM D-2a (lower panel) and untreated HeLa cells (upper panel). The scale bar in FIG. 2E is 10 µM. FIG. 2F is transmission electron microscopy ("TEM") image of a hydrogel. FIG. 2G is a high magnification of the image shown in FIG. 2F, illustrating a junction of nanofibrils. The scale bars in FIGS. 2F-2G are each 100 nm.

FIG. 3A shows overlaid images and 3D stacked z-scan images of Congo red and DAPI stained HeLa and Ect1/E6E7 cells treated with D-2a (upper panel) or culture medium control (lower panel) for 12 hours. HeLa cells were treated with 280 µM D-2a; Ect/E6E7 cells were treated with 560 µM D-2a. Scale bar=10 µM. White dots outline the cells. FIG. 3B shows the comparison of phosphate activity in blank medium ("Blank"), medium incubated with HeLa cells ("Control"), pericellular hydrogels on HeLa cells treated with 560 µM D-2a ("Gel"), and the suspension medium of HeLa cells treated with 560 µM of D-2a ("Suspension"). FIG. 3C is an SDS-PAGE gel showing the protein composition in the Blank, Control, Gel, and Suspension. Arrows indicate protein bands that appear only in the lane of the Gel. FIG. 3D shows the cell viabilities of HeLa ("H"), Ect1/E6E7 ("E"), MES-SA ("M"), and MES-SA/Dx5 ("MD") cells treated with 280 µM of D-2a or HeLa cells treated with 280 µM D-2b for 48 hours. FIG. 3E shows the change in the relative amount of apoptosis signal molecules over time in HeLa cells treated with 280 µM of D-2a.

FIGS. 4A-4D show the formation of a hydrogel in HeLa cell conditioned medium 48 hours following treatment with 560 µM D-2a (FIG. 4A), 280 µM D-2a (FIG. 4B), 140 µM D-2a (FIG. 4C) D-2a, or 560 µM D-2b (FIG. 4D). Arrows show the gelation in FIGS. 4A-4B.

FIGS. 5A-5B are optical images of HeLa cells showing that a high gradient of phosphatases in the pericellular space promotes the formation of the pericellular hydrogel. FIG. 5A shows HeLa cells following treatment with 560 µM D-2a and phosphatase inhibitors (Pierce™: sodium fluoride, sodium orthovanadate, sodium pyrophosphate, and beta-glycerophosphate) for 2 hours. FIG. 5B shows HeLa cells following treatment with 560 µM D-2a and alkaline phosphatase ("ALP") (0.1 U/mL) for two hours.

FIG. 6 is a panel of SEM images of freeze dried HeLa cells treated with 280 µM D-2a for 2 hours. Scale bar=10 mm.

FIG. 7 is a TEM of a hydrogel formed by ALP induced enzymatic hydrogelation of D-2a in PBS buffer. The hydrogel was formed by incubating 0.6 U/mL of ALP with D-2a at 0.2 wt % for 6 hours. Scale bar=100 nm.

FIG. 8 is an optical image of Ect1/E6E7 cells incubated with 560 µM D-2a for 48 hours.

FIG. 10A shows the migration of HeLa cells after incubation with D-2a, D-2b, or culture medium alone (control) for 18 hours. FIG. 10B is a plot of time versus the percentage of cells attached to a Petri dish following the treatment of suspended HeLa cells with 560 µM of D-2a, D-2b, or culture medium alone (control).

FIG. 12A shows the distribution of D-2b around the HeLa cells due to pericellular dephosphorylation of D-2a. FIG. 12B illustrates the distribution of D-2b around HeLa cells via direct addition of D-2b. The arrows indicate the direction of motion of the D-2b molecules.

FIG. 14A shows the time dependent conversion of D-2a to D-2b by complete culture medium containing secretory enzymes from HeLa cells. FIG. 14B shows the time dependent degradation of L-2a, L-2b, and L-2c by complete culture medium containing secretory enzymes from HeLa cells.

FIGS. 16A-16B illustrates the relative MES-SA/Dx5 tumor volume in mice following in vivo treatment of mice with D-2a. FIG. 16A shows the relative tumor volume of mice injected subcutaneously and peritumorally every three days (six doses, starting day 1) with either 100 µl of D-2a at 8 µg/µL in PBS buffer or with PBS buffer alone as a control. Data are shown as mean±SD (n=6 for the group treated with 32 mg/kg of D-2a, and n=3 for the control group). *p<0.05, **p<0.01 by Student's t test. FIG. 16B show representative images of mice bearing tumors with similar initial volume ($V_0$) from the treated and control groups on $19^{th}$ day of treatment with D-2a.

FIG. 17A is an illustration of phosphatase-catalyzed spatiotemporal formation of fluorescent pericellular nanofibrils in co-culture mimicking tumor microenvironment. FIG. 17B shows the molecular structures of a related precursor (D-3a) and the corresponding hydrogelator (D-3b). ALP or tyrosine phosphatase ("PTP") converts D-3a to D-3b, which self-assembles in physiological condition to form fluorescent nanofibrils of D-3b. FIG. 17C contains a pair of fluorescent images showing that the fluorescent nanofibrils of D-3b selectively form on HeLa cells (the cancer cell, identified by arrows) and in HS-5 cells (the stromal cell, indicated by the arrow heads) in the co-culture of HeLa and HS-5. [D-3a]=500 µM, 6 hours (left panel) and 24 hours (right panel) incubation (scale bar=10 µm, the nuclei stained by Hoechst 33342, a DNA dye for live cells).

FIGS. 18A-F show confocal microscopy images. FIG. 18A shows images taken 24 hours after incubation of selected cell lines (PC-12 Adh, Caspan-2, A375, Ect1/E6E7, and C3H10T1/2 cells, respectively) with 500 µM D-3a. The scale bar is 10 nm. The images in FIG. 18B show the time course of fluorescence on HeLa cells incubated with D3-a for 30 minutes, 1 hour, 3 hours, and 6 hours, respectively. Nuclei were stained with Hoechst 33342. FIG. 18C is a 3D stacked z-scan image of fluorescence on HeLa cells treated with D-3a for 6 hours. FIG. 18D shows that no fluorescence was observed on HeLa cells after re-incubating the cells (from FIG. 18A, 6 hours) in fresh medium for 24 hours. FIG. 18E shows the fluorescence emission on stromal cells (HS-5, 24 hours) and cancer cells (A2780, A2780cis, PC-3, MES-SA, and MES-SA/Dx5, 24 h), incubated with D-3a. FIG. 18F shows the fluorescence on cancer cells (MCF-7) incubated with D-3a, in the absence (top panel) and presence (bottom panel) of a hormone (prednisolone). Scale bar: 100 µm for FIG. 18B, upper panels and FIG. 18D; 10 µm for FIG. 18B, lower panels, FIG. 18E, and FIG. 18F. [D-3a]=500 µM for enhancing spatiotemporal resolution. FIG. 18G shows the quantification of ectophosphatases on HeLa cells according to the amount of pericellular nanofibrils by measuring the fluorescence intensity of the molecules remaining on the cell surface. FIG. 18H is a plot of time versus the fluorescence of pericellular nanofibrils on HeLa cells treated with D-3a. The initial cell number is 5,000 cells/well. All the confocal microscope images were taken after removing the medium with D-3a and then adding the live cell image solution (Invitrogen Life Technologies A14291DJ). [D3-a]=500 µM for FIGS. 18G-H.

FIG. 19A shows the ectophosphatase-catalyzed dephosphorylation of the hydrogelator precursor molecule (e.g., D-2a), resulting in nanofibril formation by, e.g., D-2b near the cell surface (i.e., in the pericellular space). FIG. 19B is a schematic illustration of the self-assembly of hydrogelator molecules D-2b into a network of manofibrils. FIG. 19C is an illustration of the sequestration of the cancer cell secretome by nanonets/hydrogel formed in the pericellular space of cancer cells. FIG. 19D is a flow chart of the collection of proteins from the pericellular nanonets/hydrogels.

FIG. 20A is an image of a silver-stained SDS-PAGE gel showing proteins from the HeLa cell sercretome collected using the nanonets/hydrogel method ("2 h N") compared to proteins from the HeLa cell secretome collected using the conditioned medium method following 2 hours of incubation ("2 h CM"). As a control for the nanonets/hydrogel, a piece of hydrogel ("Gel") is analyzed in parallel. FIG. 20B is a graph showing the relative density of the 300, 160, 55, and 13 kDa protein bands corresponding to "2 h N" and "2 h CM" in trials 1 and 2. FIG. 20C is a graph showing, according to mass profiling, the number of total peptide and unique peptides in the HeLa cell secretome from the "2 h N" and "2 h CM" samples. FIG. 20D is a graph showing the number of total protein and unique protein (unique protein number ≥2) observed from protein mass spectrometry in the HeLa cell secretome from the "2 h N" and "2 h CM" samples. FIG. 20E is a graph showing the correlation of the unique peptide hits of proteins detected in the two trials of "2 h N". FIG. 20F is a graph showing the correlation of the unique peptide hits of protein detected in the two trials of "2 h CM". FIG. 20G shows a comparison between the proteins identified in "2 h N" and "2 h CM". The HeLa cell secretome reported in the literature (Wu et al., *Mol. Cell. Proteomics* 9:1100-1117 (2010), which is hereby incorporated by reference in its entirety) served as a reference. FIG. 20H shows the analysis of 122 proteins identified in the two trials of "2 h N". The subcellular location information of the proteins was collected from UniProt. FIG. 20I is a pie chart that represents the molecular functional profiles of the proteins in the secretome collected from the pericellular nanonets/hydrogel of HeLa cells ("2 h N") and culture medium ("2 h CM"). The predicted secretory properties of the proteins were analyzed using Secretome 2.0. Functional classification was analyzed using PANTHERS.

FIG. 21A is a scheme showing the collection of nanonets from HeLa cells exposed to FBS-free medium for different lengths of time. As a control, culture medium ("CM") was collected from HeLa cells exposed to FBS-free medium for 24 hours. FIGS. 21B-21C are graphs showing the number of total peptide and either unique peptides (21B) and identified proteins (21C) observed in N_0, N_4, N_8, N_12, and CM by protein mass spectrometry. FIG. 21D is a graph showing the change in unique peptide number of several essential proteins in secretome observed in the nanonets. FIG. 21E is a graph showing the change in unique peptide number observed in MS protein profiling.

FIG. 22A shows several pie charts which represent the molecular functional profiles of the cancer cell secretome collected following FBS-deprivation for different lengths of time: 0 h (N_0), 4 h (N_4), 8 h (N_8), and 12 h (N_12). FIG. 22B is a plot that represents the temporal behaviors of different categories of cancer secretome based on molecule functions, during the FBS-deprivation for different lengths of time (0 h, 4 h, 8 h, and 12 h) and incubation in conditioned media for 24 hours. FIG. 22C is a plot that illustrates the fluctuating range (shown as standard deviation) of the temporal behavior for categorized proteins in the secretomes.

FIG. 24A shows that 4 hour pre-incubation in DMEM and 4 hour pre-incubation in stromal cell conditioned DMEM leads to an increase of secretory proteins from HeLa cells, compared to HeLa cells incubated in complete MEM. FIG. 24B shows that 24 h CM collects significantly less secretory proteins than the pericellular nanonets do. FIG. 24C includes pie charts that represent molecular functional profiles of cancer secretome collected upon changing media.

FIGS. 32A-32C illustrate the formation of nanonets using D-1a. FIG. 32A is an illustration of the enzyme-catalyzed formation of nanonets. A precursor hydrogelator molecule is converted to a hydrogelator, triggering self-assembly of the hydrogelator. FIG. 32B shows the structures of a precursor hydrogelator (D-1a) and the corresponding hydrogelator (D-1b) of a D-peptide. FIG. 32C shows the optical image of the hydrogel of D-1b and the TEM image of the nanonets of D-1b in the hydrogel.

FIG. 33A is a Western blot showing the amount of tubulins in CM collected after 24 hours of incubation or pericellular nanonets collected after 3 to 9 hours of incubation. The bar graph shows the relative density of the tubulin bands. Both CM and nanonets were collected in FBS-free MEM. FIG. 33B shows viability of cells after cold shock and nanonet collection (incubated with D-2a for 4 hours in FBS-free MEM). Two trials, each has three repeats.

FIG. 38A shows molecular structures of the precursors D-3a and D-4a, and their corresponding hydrogelators D-3b and D-4b. FIG. 38B shows TEM images of the nanonets of D-3b in the hydrogel (inset) formed by enzyme-catalyzed dephosphorylation of D-3a with ALP (2 U/ml). Scale bars=100 nm.

DETAILED DESCRIPTION OF THE INVENTION

Figures 1A, 1B:
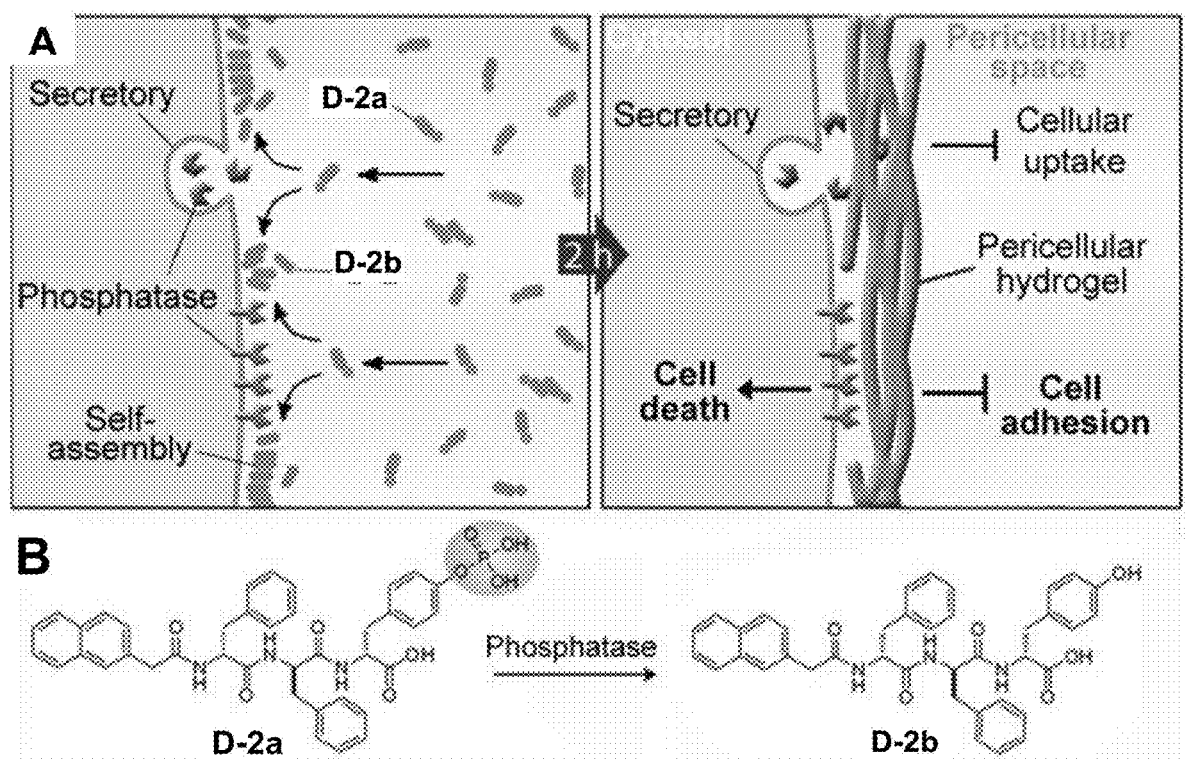

A first aspect of the invention relates to a peptide comprising up to about 35 amino acids, including a plurality of aromatic amino acid residues and either (i) an amino acid residue that is phosphorylated or sulfated, or (ii) an amino acid comprising a covalently bonded ester-moiety, or both (i) and (ii), wherein, upon exposure to a cell that expresses an ectoenzyme that hydrolyzes the phosphate group, the sulfate group, or the ester-moiety, the peptide self-assembles to form nanofibrils externally of the cell.

The peptides of the present invention are innocuous to normal cells, but upon exposure to cellular enzymes, particularly ectoenzymes, on the surface of or expressed by target cells, the peptides self-assemble into nanofibrils and nanonets on the surface of target cells. Exemplary ectoenzymes include, without limitation, phosphatases, sulfatases, and peptidases (esterases), particularly those having hydrolytic (hydrolase) activity.

Target cells that can be covered by the nanofibrils/nanonets include cells that express or secrete the ectoenzyme. Exemplary target cells include without limitation, cancer cells, mammalian progenitor cells, virus-infected cells, bacterial pathogens, protozoa, and fungi.

As used herein, the term "nanofibril" is defined as a fiber of material having any shape wherein at least one dimension, e.g. the diameter, width, thickness, and the like, is about 100 nm or less. Nanofibril diameters may be about 50 nm or less, about 40 nm or less, about 30 nm or less, about 20 nm or less, about 10 nm or less, about 5 nm or less, about 4 nm or less, about 3 nm or less, about 2 nm or less, or about 1 nm or less in diameter. Although a hydrogelator upon self-assembly, as described herein, forms nanofibrils, persons of skill in the art should appreciate that such a hydrogelator may also form microfibrils that are larger than 100 nm thick.

As used herein, the term "nanonet" or "nanonets" is defined as a three-dimensional assembly of nanofibrils. As used herein, the term "nanonet(s)" does not preclude the assembly from containing a portion of fibrils that are larger than 100 nm thick.

Peptide nanofibril self-assembly occurs both in vivo and ex vivo. Nanofibrils and nanonets have the capacity to physically alter the target cells and their interactions with the cellular microenvironment. Use of these peptides, and compositions thereof, is contemplated for the treatment of patients with cancerous or precancerous conditions, as well as for the inhibition of target cell migration, inhibiting target cell survival, inhibiting target cell growth, and/or inhibiting passage of intracellular signaling molecules to or from the nanofibril network-covered target cells.

In certain embodiments, the peptides of the present invention do not contain lysine residues. The presence of a lysine residue is believed to inhibit the pericellular hydrolysis of the phosphate group, the sulfate group, or the ester-moiety, presumably by promoting cell uptake prior to hydrolysis.

In one embodiment, the aromatic amino acids used in the peptides of the present invention include natural and/or non-natural aromatic amino acid residues, without limitation, any one or more of phenylalanine, phenylalanine derivatives, tyrosine, tyrosine derivatives, tryptophan, and tryptophan derivatives. Any known or hereinafter developed phenylalanine derivatives, tyrosine derivatives, or tryptophan derivatives can be used in the present invention, as long as the derivatives facilitate self-assembly of the nanofibrils. Exemplary derivatives of these amino acids include the addition of one or more ring substituents.

The peptides can include all D-amino acids, all L-amino acids, or a mixture of L-amino acids and D-amino acids. In preferred embodiments, the peptide includes only D-amino acids or a mixture of D-amino acids and L-amino acids where the D-amino acid content is greater than 50%, 60%, 70%, 80%, 90%, or 95%.

As a consequence of utilizing entirely D-amino acids or a high proportion of D-amino acids, it is possible to render the peptide protease resistant, e.g., resistant to proteinase K digestion.

In certain embodiments, a phosphorylated amino acid residue is present in the peptide without any other moiety to inhibit self-assembly. Alternatively, the peptide can include both the phosphorylated amino acid residue and an amino acid residue comprising an ester-moiety linked via peptide bond (to said residue). Exemplary amino acids residues that are readily phosphorylated and catalytically dephosphorylated by an enzyme possessing hydrolase activity include, without limitation, serine, threonine, tyrosine, and histidine.

In certain embodiments, a sulfated amino acid residue is present in the peptide without any other moiety to inhibit self-assembly. Alternatively, the peptide can include both the sulfated amino acid residue and an amino acid residue comprising an ester-moiety linked via peptide bond (to said residue). Exemplary amino acids residues that are readily sulfated and catalytically desulfated by an enzyme possessing hydrolytic activity include, without limitation, serine, threonine, tyrosine, and hydroxyproline.

In certain embodiments, the peptide does not possess a phosphorylated or sulfated amino acid residue, but instead includes only the amino acid conjugated to an ester-moiety linked via peptide bond. In this and the preceding embodiments, the amino acid residue to which an ester-moiety is linked, typically though not necessarily via peptide bond, can be any amino acid, whether or not the amino acid contains an aromatic side chain. In these embodiments, the ester-moiety can be any ester-containing compound that also possesses a primary amino group that can react with the C-terminal carboxylic acid to form a peptide bond. Suitable ester moieties include, without limitation, 4-(2-aminoethyl)-4-oxobutanoic acid; 5-aminovaleric acid; 4-[(8-aminooctyl)amino]-4-oxobutanoic acid; 4-[(5-amino-1-oxopentyl)amino]butanoic acid; and 4-[(5-aminopentyl)amino]-4-oxobutanoic acid.

In each of the preceding embodiments, the peptide may optionally include an N-terminal amino acid capped by a capping moiety. The capping moiety preferably includes an acyl group due to the reaction of a carboxylic acid with the N-terminal amino group to form a peptide bond.

The capping moiety may or may not include an aromatic or heteroaromatic group. Exemplary capping moieties include, without limitation, alkylacyls such as acetyl, proprionyl, or fatty acid derivatives, or an arylacyl such as 2-naphthalacetyl or 3-((7-nitrobenzo(c)-1,2,5-oxadiazol-4-yl)amino)proprionyl, or heteroarylacyls such as an acylated nucleoside. These capping moieties can protect against enzymatic degradation of the peptide, as well as promote self-assembly in the case where aromatic groups are present in the capping moiety.

Exemplary nucleobases include, without limitation, thyminyl, uracilyl, cytosinyl, adeninyl, and guaninyl. These nucleobases are preferably acylated, e.g., acetyl, proprionyl, etc.

In certain embodiments, the capping moiety may or may not include a fluorophore, a chemotherapeutic agent, an antiangiogenic agent, a thermoablative nanoparticle, an immunomodulating agent, or an antigen. Numerous examples of each of these categories are well known in the art.

In certain embodiments, where the peptide does not include a C-terminal linked ester moiety, the peptide may instead include at its C-terminal amino acid a glycoside moiety or 3-aminophenyl boronic acid, which is linked to the peptide by a peptide bond. The glycoside can be any monosaccharide or disaccharide, including without limitation, fructosyl, galactosyl, glucosyl, or mannosyl. One exemplary glycoside is D-glucosamine ("GlcN"). In accordance with this embodiment, the peptide may comprise an N-terminal heterocyclic aromatic group. The heterocyclic aromatic group can protect against enzymatic degradation of the peptide, as well as promote self-assembly.

In certain embodiments, the peptides does not contain a nucleobase capping moiety except when the peptide also includes a C-terminal glycoside moiety, 3-aminophenyl boronic acid, or a C-terminal ester moiety.

The peptides of the present invention can have any length that is sufficient to allow for self-assembly once the enzyme (preferably an ectoenzyme having hydrolase activity) dephosphorylates, desulfates, and/or de-esterifies the peptide. This includes peptides up to about 35 amino acids, up to about 30 amino acids, up to about 25 amino acids, up to about 20 amino acids, up to about 15 amino acids, or up to about 10 amino acids. In certain embodiments, the peptides contain from 3 to 10 amino acids.

In certain embodiments, the peptide contains about 10 percent up to about 100 percent of aromatic amino acid residues.

Although numerous oligopeptides are known to form supermolcular hydrogels, those containing multiple aromatic groups facilitate aromaticaromatic interactions that likely stabilize the intermolecular hydrogen bonding in water to afford the hydrogels. Du et al., "Supramolecular Hydrogels Made of Basic Biological Building Blocks," Chem. Asian J. 9(6):1446-1472 (2014), which is hereby incorporated by reference in its entirety. Examples include, without limitation, the conjugation of aromatic moieties (e.g., phenyl, naphthyl, fluorenyl, pyrenyl, cinnamoyl) via simple amide bond to either or both of aromatic amino acids (e.g., phenylalanine, tyrosine, tryptophan) and non-aromatic amino acids. In addition, aromatic derivatives of amino acids can be used, such as naphthylalanine.

Exemplary peptides of the present invention include, without limitation: NapAc-Phe-Phe-Tyr(phospho), one example of which, formed using D-amino acids, is shown below:

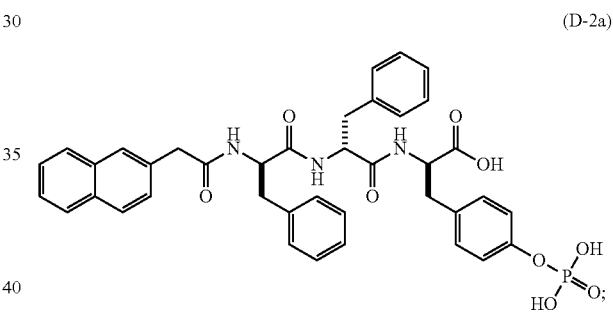

(D-2a)

NBD-Prop-Nal-Phe-Phe-Tyr(phospho) (SEQ ID NO:1), one example of which, formed using D-amino acids, is shown below:

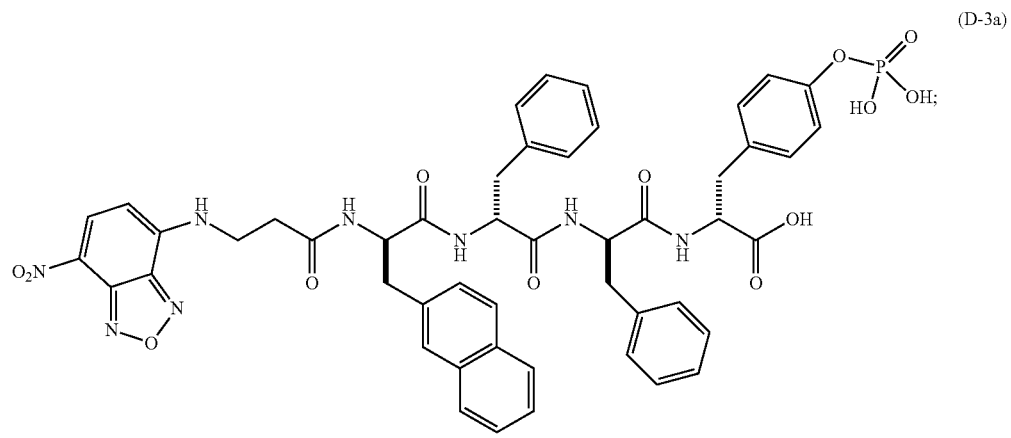

(D-3a)

NBD-Prop-Nal-Nal-Phe-Tyr(phospho) (SEQ ID NO:2), one example of which, formed using D-amino acids is shown below:
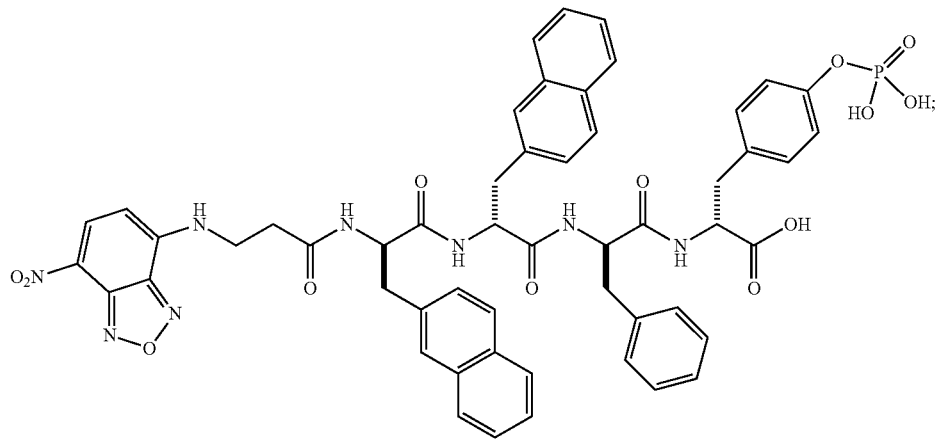
(D-4a)
Thy-Phe-Tyr(phospho)-GlcN, whose L-amino acid and D-amino acid variants are shown below, formed using D-GlcN:
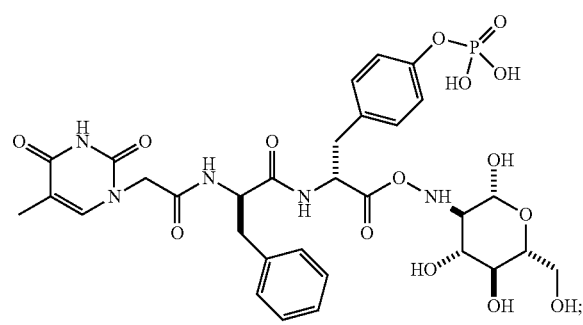
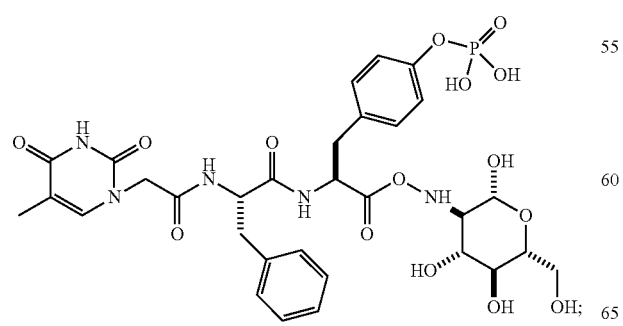
Thy-Phe-Phe-Tyr(phospho)-GlcN, whose L-amino acid and D-amino acid variants are shown below, formed using D-GlcN:
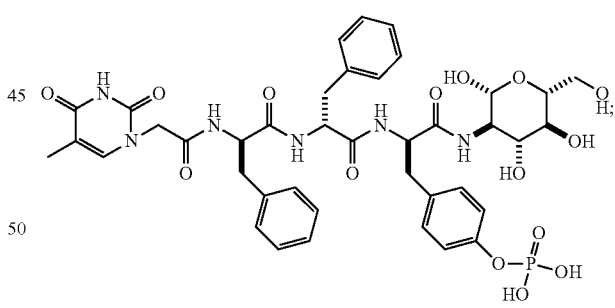
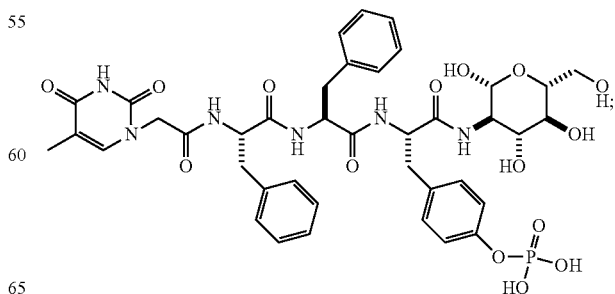

NBD-Prop-Phe-Phe-Tyr(phospho), one example of which, formed using D-amino acids, is shown below:
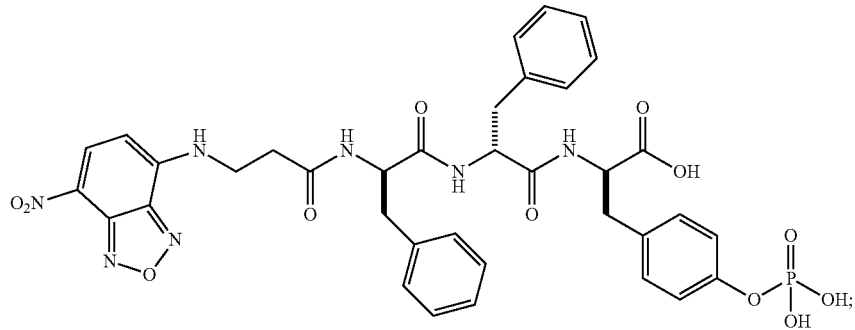
NBD-Prop-Nal-Phe-Phe-Tyr(phospho)-GlcN (SEQ ID NO:3), one example of which, formed using D-amino acids, is shown below:
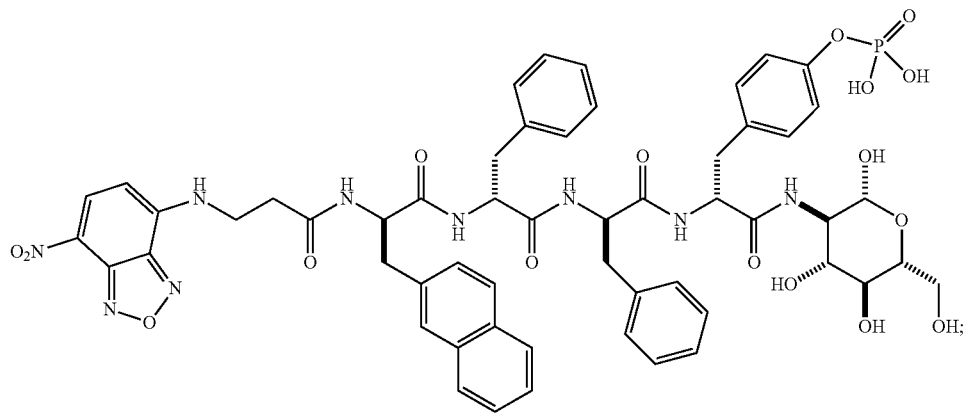
NBD-Prop-Phe-Phe-Tyr(phospho)-GlcN, one example of which, formed using D-amino acids, is shown below:
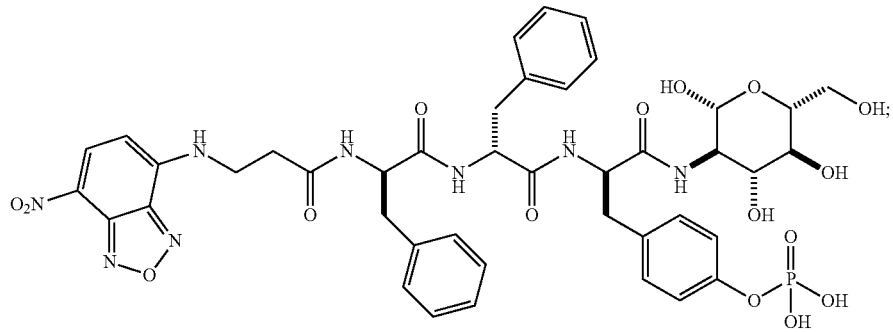

NapAc-Phe-Tyr(phospho)-AEOBA, whose L-amino acid and D-amino acid variants are shown below:
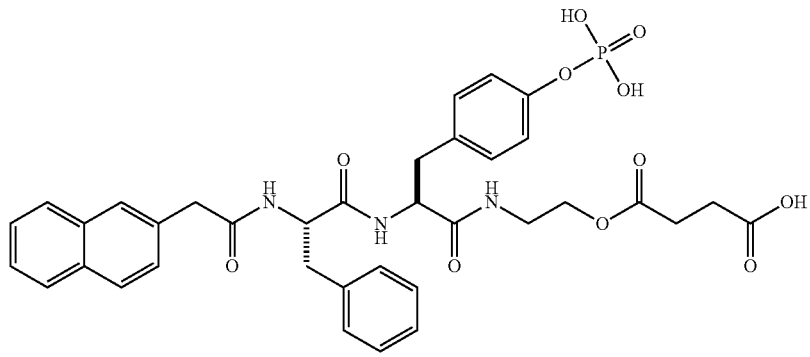
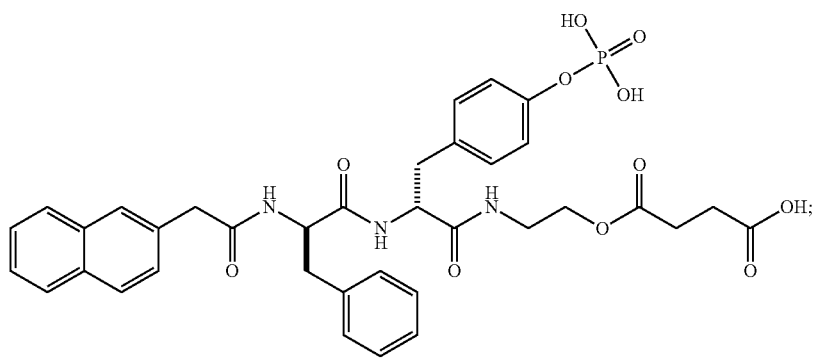
Ac-Met-Leu-Nal-Nal-Tyr(phospho) SEQ ID NO:4);
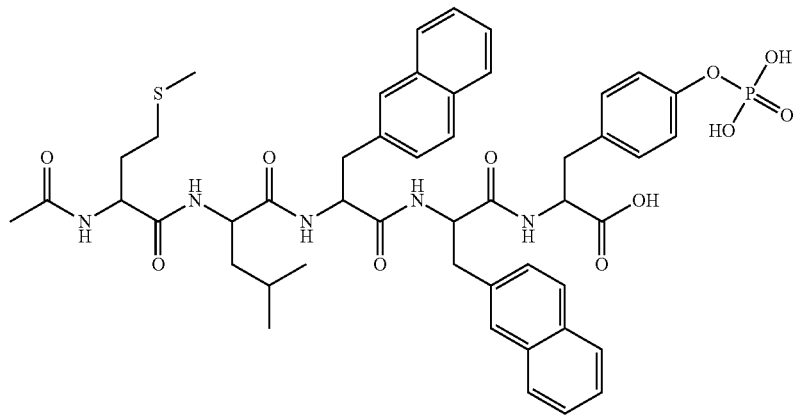 [SMILES: CSCCC(NC(C)=O)C(=O)NC(CC(C)C)C(=O)NC(Cc1ccc2ccccc2c1)C(=O)NC(Cc1ccc2ccccc2c1)C(=O)NC(Cc1ccc(OP(=O)(O)O)cc1)C(=O)O]

Ac-Nal-Phe-Phe-Tyr(phospho)-APBA (SEQ ID NO:5), whose amino acid residues can be L-amino acids, D-amino acids, or a combination thereof, as shown below:

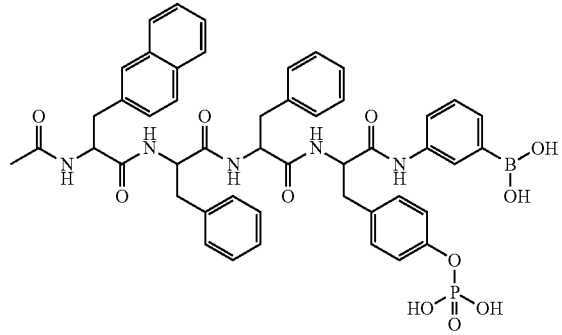 [SMILES: CC(=O)NC(Cc1ccc2ccccc2c1)C(=O)NC(Cc1ccccc1)C(=O)NC(Cc1ccccc1)C(=O)NC(Cc1ccc(OP(=O)(O)O)cc1)C(=O)Nc1cccc(B(O)O)c1]

Formyl-Met-Leu-Nal-Nal-Tyr(phospho) (SEQ ID NO:6), whose L-amino acid and D-amino acid variants are shown below, except that Nal and Tyr residues can be L- or D-amino acids, or any combination thereof:

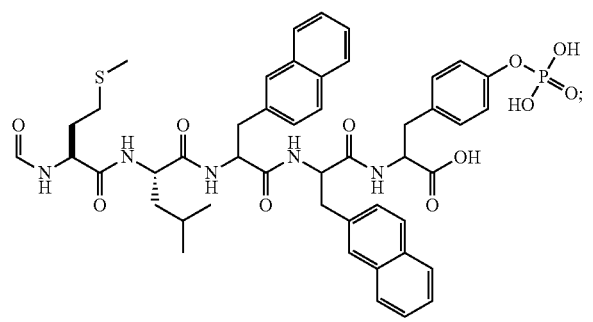

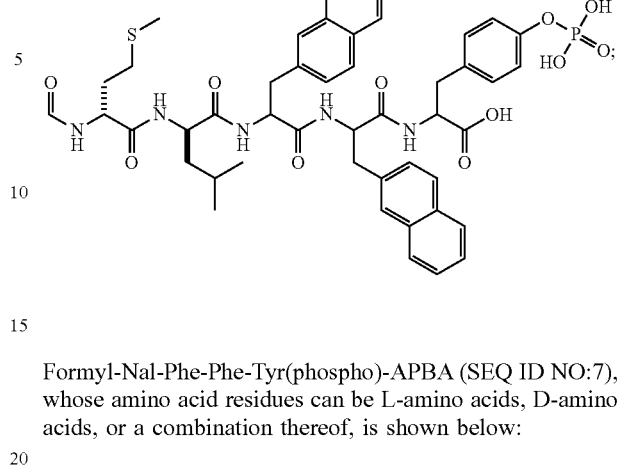

Formyl-Nal-Phe-Phe-Tyr(phospho)-APBA (SEQ ID NO:7), whose amino acid residues can be L-amino acids, D-amino acids, or a combination thereof, is shown below:

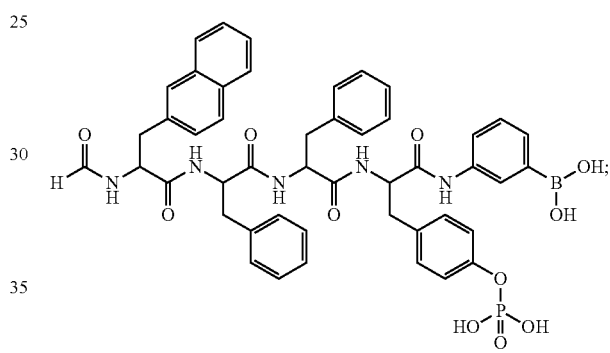

and

NapAc-Phe-Phe-Tyr(phospho)-APBA, whose amino acid residues can be L-amino acids, D-amino acids, or a combination thereof, is shown below:

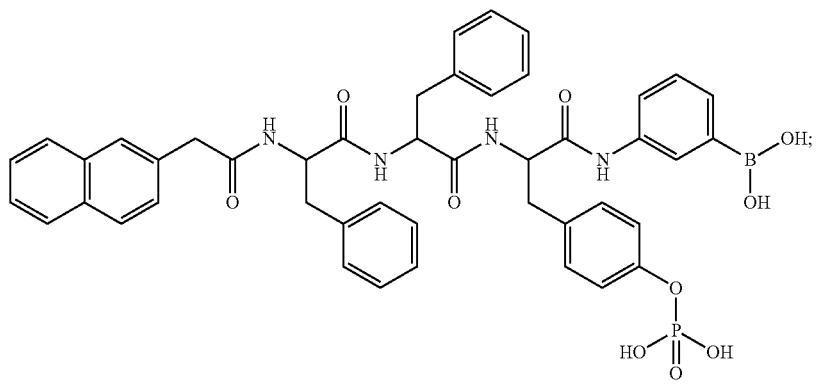

where Ac is an acetyl group; NapAc is a 2-naphthalenyl-acetyl group; NBD-Prop is a (7-nitro-1,2,5-benzoxadiazolyl amino)proprionyl group, Glcn is D-glucosamine; AEOBA is 4-(2-aminoethyl)-4-oxobutanoic acid; APBA is 3-aminophenyl boronic acid; and Thy is a thyminylacyl group.

The peptides of the present invention can be synthesized using standard peptide synthesis operations. These include both 9-Fluorenylmethyloxy-carbonyl ("FMOC") and tert-Butyl oxy carbonyl ("tBoc") synthesis protocols that can be carried out on automated solid phase peptide synthesis instruments including, without limitation, the Applied Biosystems 431A, 433A synthesizers and Peptide Technologies Symphony or large scale Sonata or CEM Liberty automated solid phase peptide synthesizers. This can be followed with standard HPLC purification to achieve a purified peptide product.

Where N-terminal capping groups or C-terminal moieties are introduced, these can also be introduced using standard peptide synthesis operations as described above. For example, carboxylic acid containing precursors can be coupled by peptide bond to the N-terminus of the peptide, and amino containing precursors can be coupled by peptide bond to the C-terminus of the peptide.

In general, amino groups present in lysine side chains (if present), as well as the N-terminal amino group, can be reacted with reagents possessing amine-reactive functional groups using known reaction schemes. Exemplary amine-reactive functional groups include, without limitation, activated esters, isothiocyanates, and carboxylic acids. Reagents to be conjugated include those listed above.

In general, guanidine groups present in arginine can be reacted with reagents possessing guanidine-reactive groups using known reaction schemes. Exemplary guanidine-reactive functional groups include, without limitation, NHS esters using gas phase synthesis (McGee et al., *J. Am. Chem. Soc.*, 134 (28):11412-11414 (2012), which is hereby incorporated by reference in its entirety).

In general, thiol groups present in cysteine (or cysteine derivative) side chains can be reacted with reagents possessing thiol-reactive functional groups using known reaction schemes. Exemplary thiol-reactive functional groups include, without limitation, iodoacetamides, maleimides, and alkyl halides. Reagents to be conjugated include those listed above.

In general, carboxyl groups present in glutamic or aspartic acid side chains, or at the C-terminal amino acid residue, can be reacted with reagents possessing carboxyl-reactive functional groups using known reaction schemes. Exemplary carboxyl-reactive functional groups include, without limitation, amino groups, amines, bifunctional amino linkers. Reagents to be conjugated include those listed above.

In each of the types of modifications described above, it should be appreciated that the conjugate can be directly linked via the functional groups of the peptide and the reagent to be conjugated, or via a bifunctional linker that reacts with both the peptide functional groups and the functional groups on the reagent to be conjugated.

In general, the peptides of the present invention can be either (i) dephosphorylated or desulfated, (ii) hydrolyzed at an ester bond, or both (i) and (ii) to form a derivative hydrogelator. Exemplary derivative hydrogelators include: NapAc-Phe-Phe-Tyr; NBD-Prop-Nal-Phe-Phe-Tyr (SEQ ID NO:8); NBD-Prop-Nal-Nal-Phe-Tyr (SEQ ID NO:9); Thy-Phe-Tyr-GlcN; Thy-Phe-Phe-Tyr-GlcN; NBD-Prop-Phe-Phe-Tyr; NBD-Prop-Nal-Phe-Phe-Tyr-GlcN (SEQ ID NO:10); NBD-Prop-Phe-Phe-Tyr-GlcN; NapAc-Phe-Tyr-AEOBA; Ac-Met-Leu-Nal-Nal-Tyr (SEQ ID NO:11); Ac-Nal-Phe-Phe-Tyr-APBA (SEQ ID NO:12); and NapAc-Phe-Phe-Tyr-APBA, wherein the amino acids are all D-amino acids, all L-amino acids, or a combination of both D-amino acids and L-amino acids.

A second aspect of the invention relates to a pharmaceutical composition comprising a pharmaceutically acceptable carrier and a peptide according to the first aspect of the invention, which is present in an effective amount.

In certain embodiments, more than one peptide can be provided. The peptides can be similar in structure, but possess different conjugated agents as described above. In alternative embodiments, the peptides can be structurally distinct, including different structures that are nevertheless capable of self-assembly due to the structural compatibility of the aromatic amino acids residues in the different peptides.

In certain embodiments, the carrier is an aqueous medium that is well tolerated for administration to an individual, typically a sterile isotonic aqueous buffer. Exemplary aqueous media include, without limitation, normal saline (about 0.9% NaCl), phosphate buffered saline ("PBS"), sterile water/distilled autoclaved water ("DAW"), as well as cell growth medium (e.g., MEM, with or without serum), aqueous solutions of dimethyl sulfoxide ("DMSO"), polyethylene glycol ("PEG"), and/or dextran (less than 6% per by weight.)

To improve patient tolerance to administration, the pharmaceutical composition preferably has a pH of about 6 to about 8, preferably about 6.5 to about 7.4. Typically, sodium hydroxide and hydrochloric acid are added as necessary to adjust the pH.

The pharmaceutical composition suitably includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The composition may also include solubilizing agents, preservatives, stabilizers, emulsifiers, and the like. A local anesthetic (e.g., lidocaine) may also be included in the compositions, particularly for injectable forms, to ease pain at the site of the injection.

Effective amounts of the peptide will depend on the nature of use, including the nature of the cancerous condition which is being treated, tumor volume and stage, and its location(s). By way of example only, suitable peptide concentrations may range from about 1 µM to about 10 mM, preferably about 10 µM to about 5 mM, about 50 µM to about 2 mM, or about 100 µM to about 1 mM. The volume of the composition administered, and thus, dosage of the peptide administered can be adjusted by one of skill in the art to achieve optimized results. As demonstrated in Example 7, infra, 800 µg per day, repeated every third day was effective. This can be adjusted lower to identify the minimal effective dose, or tailored higher or lower according to the nature of the tumor to be treated.

Further aspects of the invention relate to methods of forming a nanofibril network on or near the surface of target cells, methods of collecting a cancer cell secretome, a screening method for a target cell secretome, and methods of treating a cancerous condition in a patient.

In accordance with another aspect of the invention, relating to methods of forming a nanofibril network on or near the surface of target cells, the method involves contacting a target cell that expresses a cell surface-bound enzyme having hydrolytic (hydrolase) activity, secretes an enzyme having hydrolytic (hydrolase) activity, or both, with a peptide of the invention or a pharmaceutical composition containing the same, wherein the contacting is effective to hydrolyze the phosphate group, the sulfate group, or the ester moiety and cause in situ self-assembly of the peptides to form a nanofibril network on or near the surface of the target cell. As a consequence of forming the nanofibril network on or near the target cell surface, one or more of the following occurs: target cell migration is inhibited, target cell survival is inhibited, target cell growth is inhibited, and/or passage of intracellular signaling molecules to or from the nanofibril network-covered target cell is inhibited. With regard to the latter property, it is believed that the nanofibril network results in sequestration of cell signaling molecules by the gel outside the cell. The sequestered cell signaling molecules include both molecules produced and secreted by the target cell cells as well as signaling molecules produced and secreted by non-target cells in the cancer microenvironment. The target cell can be ex vivo or in vivo (in accordance with the method of treatment described below).

When performed ex vivo or surgically recovered from an individual subsequent to an in vivo treatment in accordance with the present invention, the nanofibril network which sequesters or contains cell signaling molecules can be harvested and used independently either for raising therapeutic antibodies to cancer cells (a passive anti-cancer vaccine component) or as a component in an active anti-cancer vaccine formulation. In accordance with these embodiments, the method further comprises raising antibodies against the cancer cell signaling molecules recovered from the hydrogel.

In each of the above embodiments relating to methods of forming a nanofibril network on or near the surface of target cells, the target cells may be cancer cells. In accordance with these embodiments of the method of forming a nanofibril network on or near the surface of target cells, the nanofibril network results in a gel outside cells to sequester cell signaling molecules, wherein the cell signaling molecules are from cancer cells or from a cancer microenvironment. In other embodiments, the gel containing the cancer cell signaling molecules is used for raising antibodies against cancers. In additional embodiments, the contacting is effective to inhibit cancer cell migration, inhibit cancer cell survival, inhibit cancer cell growth, and/or inhibit passage of intracellular signaling molecules to or from the nanofibril network-covered cancer cell.

In accordance with another aspect of the invention, relating to methods of collecting a target cell secretome, the method involves contacting a target cell that expresses a cell surface-bound enzyme having hydrolytic (hydrolase) activity, secretes an enzyme having hydrolytic (hydrolase) activity, or both, with an effective amount of the peptide according to the invention or a pharmaceutical composition containing the same, wherein the contacting is effective to hydrolyze the phosphate group, the sulfate group, or the ester moiety and cause in situ self-assembly of the peptide to form a nanofibril network on or near the surface of the target cells to retain target cell secretome from the pericellular space of the target cell. This method further involves separating the target cell secretome from the nanofibril network and collecting the separated target cell secretome.

In one embodiment, separating the target cell secretome from the nanofibril network involves cold shock to detach the nanofibril network from the target cells, and centrifugation to separate the nanofibril network from the target cells. This is particularly useful for target cells (whose secretome is being recovered) that are ex vivo. The target cells can be cultured with the peptides in vitro or alternatively, exposed in vivo to the peptides and then harvested by tissue sample and treated ex vivo. Thus, in the latter approach, the contacting is carried out in a mammal, which may be human.

In another embodiment, where the target cells are exposed in vivo to the peptides, the nanonet can be disrupted by shear forces caused by suction (and optionally irrigation with saline) at the site where peptides were introduced, and then the nanonet constituents, including the disassembled hydrogelators and the secretome, are recovered.

As described above, as a consequence of forming the nanofibril network on or near the target cell surface, passage of intracellular signaling molecules to or from the nanofibril network-covered target cell is inhibited. It is believed that the nanofibril network results in sequestration of cell signaling molecules by the gel outside the cell. The sequestered cell signaling molecules include both molecules produced and secreted by the target cell cells as well as signaling molecules produced and secreted by non-target cells in the cancer microenvironment. In some embodiments, the gel containing the cancer cell signaling molecules is used for raising antibodies against cancers.

The target cell can be ex vivo or in vivo (in accordance with the fifth aspect of the invention described below). The target cell may also be a cancer cell, as noted above.

In accordance with another aspect of the invention, relating to a screening method for a target cell secretome, the method involves forming a nanofibril network on or near the surface of target cells in the manner described above, separating the target cell secretome from the nanofibril network and collecting the separated target cell secretome as described above, and then analyzing the target cell secretome. In certain embodiments the analyzing comprises one or more of electrophoresis, microarray analysis, and mass spectrometry. In certain embodiments collection of the secretome can be temporarily controlled such that the analyzing is effective to register the temporal profiles of the target cell secretome.

In accordance with another aspect of the invention, relating to methods of treating a cancerous condition in a subject, the method involves administering to a subject having a cancerous condition a therapeutically effective amount of a peptide of the invention or a pharmaceutical composition containing the same, wherein the administering is effective to hydrolyze the phosphate group, the sulfate group, or the ester moiety and cause in vivo self-assembly of the peptides to form a nanofibril network on or near the surface of cancer cells, which has the effects noted above. Exemplary subjects include any mammal that is susceptible to cancerous conditions including, without limitation, rodents, rabbits, canines, felines, ruminants, and primates such as monkeys, apes, and humans.

In this aspect of the invention, the contacting step is effective to inhibit target cell migration, inhibit target cell survival, inhibit target cell growth, and/or inhibit passage of intracellular signaling molecules to or from the nanofibril network-covered target cell.

Administration of the peptide or pharmaceutical composition can be carried out using any suitable approach. By way of example, administration can be carried out parenterally, subcutaneously, intravenously, intradermally, intramuscularly, intraperitoneally, by implantation, by intracavitary or intravesical instillation, intraarterially, intralesionally, intradermally, peritumorally, intratumorally, or by introduction into one or more lymph nodes. In certain embodiments, administration is carried out intralesionally, intratumorally, intradermally, or peritumorally. This administration can be repeated periodically during the course of a treatment regimen, for example, one or more times per week, daily, or even one or more times per day.

In certain embodiments, the peptide is conjugated with a chemotherapeutic agent, an antiangiogenic agent, an immunomodulating agent, or an antigen. In one embodiment, the peptide may be conjugated with a thermoablative nanoparticle. In accordance with this embodiment, the method of treating a cancerous condition in subject further comprises exposing a tumor-containing region of the subject's body to a suitable energy source (e.g., ultrasound, laser light, near infrared light, or alternating magnetic field), thereby causing thermal heating of the thermoablative nanoparticle and destroying cancer cells covered by the nanofibril network.

In these several aspects of the invention relating to methods of forming a nanofibril network on or near the surface of target cells, methods of collecting a cancer cell secretome, a screening method for a target cell secretome, and methods of treating a cancerous condition in a patient, the target cells express a cell surface-bound phosphatase, secrete a phosphatase, or both; express a cell surface-bound sulfatase, secrete a sulfatase, or both; express a cell surface-bound esterase, secrete an esterase, or both; or any combination thereof. In these embodiments, the enzyme produced by the target cells is an ectoenzyme having hydrolytic activity, i.e., the enzyme hydrolyzes a phosphate group, a sulfate group, or a (carboxyl) ester group.

The target cells to be treated in accordance with these aspects can be a cancer cell and may be present in a solid tumor, present as a metastatic cell, or present in a heterogenous population of cells that includes both cancerous and noncancerous cells. Exemplary cancer conditions include, without limitation, cancers or neoplastic disorders of the brain and CNS (glioma, malignant glioma, glioblastoma, astrocytoma, multiforme astrocytic gliomas, medulloblastoma, craniopharyngioma, ependymoma, pinealoma, hemangioblastoma, acoustic neuroma, oligodendroglioma, meningioma), pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), lymph node cancer, lung (Adenocarcinoma, Oat Cell, Non-small Cell, Small Cell, Squamous Cell, Mesothelioma), skin (melanoma, basal cell, squamous cell, Kapsosi's Sarcoma), bone cancer (Ewing's Sarcoma, Osteosarcoma, Chondrosarcoma), head and neck (laryngeal, pharyngeal, and esophageal cancers), oral (jaw, salivary gland, throat, thyroid, tongue, and tonsil cancers), eye, gynecological (Cervical, Endrometrial, Fallopian, Ovarian, Uterine, Vaginal, and Vulvar), genitourinary (Adrenal, bladder, kidney, penile, prostate, testicular, and urinary cancers), and gastrointestinal (appendix, bile duct (extrahepatic bile duct), colon, gallbladder, gastric, intestinal, liver, pancreatic, rectal, and stomach cancers). Suitable cancer target cells include cancer cells derived from the forms of cancer.

Use of the peptides and pharmaceutical compositions can be coordinated with previously known therapies. For instance, where the peptide is conjugated with a thermoablative nanoparticle, after formation of the pericellular nanofibril network, a tumor-containing region of the subject's body can be exposed to a suitable energy source, thereby causing thermal heating of the thermoablative nanoparticle and destruction of cancer cells covered by the nanofibril network.

In addition, chemotherapeutic agents, immunotherapeutic agents, or radiotherapeutic agents, as well as surgical intervention can be used in a coordinated manner with the peptides or pharmaceutical compositions of the present invention. Thus, a chemotherapeutic agent, an immunotherapeutic agent, or a radiotherapeutic agent can be administered to a patient before or after treatment with the peptides or pharmaceutical compositions of the present invention. Alternatively, surgical resection of a tumor can be carried out before or after treatment with the peptides or pharmaceutical compositions of the present invention.

Additional target cells that express ectoenzymes of the types described above are mammalian progenitor cells, virus-infected cells, bacterial pathogen, protozoa, and fungi. Some of the bacterial pathogens expressing an ectoenzyme are described in PCT Publication No. WO 02/10442 to Zyskind, which is hereby incorporated by reference in its entirety. Ectophosphatase activities have been reported in several microorganisms (Freitas-Mesquita et al., *Int. J. Mol. Sci.* 15:2289-2304 (2014), which is hereby incorporated by reference in its entirety), including protozoa such as *Leishmania* (Remaley et al., *Exp. Parasitol.* 60:331-341 (1985); De Almeida-Amaral et al., *Exp. Parasitol.* 114:334-340 (2006), which are hereby incorporated by reference in their entirety), *Trypanosoma* (Fernandes et al., *Z. Naturforschung* 52C:351-358 (1997); Meyer-Fernandes et al., *Z. Naturforschung* 54:977-984 (1999); Dos-Santos et al., *Int. J. Parasitol.* 42:819-827 (2012), which are hereby incorporated by reference in their entirety), and bacteria, such as *Mycobacterium bovis* (Braibant et al., *FEMS Microbiol. Lett.* 195: 121-126 (2001), which is hereby incorporated by reference in its entirety). In fungi, ectophosphatases have been described in a large number of species (Freitas-Mesquita et al., *Int. J. Mol. Sci.* 15:2289-2304 (2014), which is hereby incorporated by reference in its entirety), including *Aspergillus fumigatus* (Bernard et al., *Microbiology* 148:2819-2829 (2002), which is hereby incorporated by reference in its entirety), and *Candida albicans* (Portela et al., *Oral Dis.* 16:431-437 (2010), which is hereby incorporated by reference in its entirety).

Further aspects of the invention relate to methods of in vivo and in vitro imaging, as well as in vitro screening of inhibitors of ectoenzymes.

For in vivo imaging, a subject is administered a diagnostically effective amount of the peptide of the invention or a pharmaceutical composition containing the same, wherein the administering is effective to hydrolyze the phosphate group, the sulfate group, or the ester moiety and cause in vivo self-assembly of the peptides to form a nanofibril network on or near the surface of the target cells, and then imaging the nanofibril network. In this embodiment, the peptide can be conjugated with a fluorophore or magnetic nanoparticle that serves as a contrast agent. In this aspect of the invention, administration can be carried out using the approaches described above for therapeutic use, but preferably intralesionally, intratumorally, intradermally, or peritumorally.

In vivo imaging of target cells (e.g., tumor cells, metastatic cells, and/or cancer cells) may be used to identify target cells and/or tissues comprising target cells prior to, during, and/or following surgical resection of a tumor (i.e., for evaluating a surgical margin of tumor tissues in a subject). Preferred peptides for use in this aspect of the invention are those that include a fluorophore whose fluorescence can be observed in real time, or those that include a magnetic/thermoablative particle as a magnetic resonance imaging contrast agent.

For in vitro imaging, a cell population comprising target cells is administered a diagnostically effective amount of the peptide of the invention, which includes a fluorophore agent, or a pharmaceutical composition containing the same, allowing the in vitro self-assembly of the peptide to form a nanofibril network on or near the surface of target cells, and imaging the nanofibril network on or near the surface of target cells, wherein the imaging is effective to identify target cell populations in vitro.

In accordance with these aspects of the invention, any of the above embodiments may comprise a cancer cell as the target cell.

In select embodiments, the peptide comprises a fluorophore in which case the nanofibril network is rendered fluorescent. In other embodiments, the peptide may comprise an MRI contrasting agent.

A further aspect of the invention relates to an in vitro screening method for inhibitors of ectoenzymes (e.g., phosphatases, esterases, sulfatases). This method involves incubating a cell population containing target cells with a compound, imaging the cell population using the in vitro imaging of the invention, wherein the imaging is effective to detect the target cells, and identifying compounds which decrease the detection of the target cells in vitro, as compared to target cells exposed to the peptide or composition but not the compound. Similarly, this method can be used to identify compounds that enhance ectoenzyme activity, by identifying compounds that enhance the detection of the target cells in vitro.

EXAMPLES

The following examples are intended to illustrate the present invention, but are not intended to limit the scope of the appended claims.

Materials and Methods for Examples 1-6

Cell Culture:

All cell lines were purchased from the American Type Culture Collection (ATCC, Manassas, Va., USA). HeLa cells were propagated in MEM supplemented with 10% fetal bovine serum ("FBS") and antibiotics in a fully humidified incubator containing 5% $CO_2$ at 37° C. Ect1/E6E7 cells were propagated in keratinocyte serum-free medium supplemented with 0.1 ng/ml human recombinant EGF, 0.05 mg/ml bovine pituitary extract, and additional calcium chloride 44.1 mg/L in a fully humidified incubator containing 5% $CO_2$ at 37° C. MES-SA cells were propagated in McCoy's 5A supplemented with 10% FBS and antibiotics in a fully humidified incubator containing 5% $CO_2$ at 37° C. MES-SA/dx5 cells were propagated in McCoy's 5A supplemented with 10% FBS, antibiotics, and 10 nM taxol in a fully humidified incubator containing 5% $CO_2$ at 37° C.

Pericellular Hydrogelation:

An 11.2 mM (8.09 mg/mL) stock solution of D-2a was prepared in $ddH_2O$. The pH was adjusted to 7.4 using 1N NaOH. $2\times10^5$ cells in exponential growth phase were seeded in 35 mm Petri dish with 1 mL complete culture medium. Following overnight incubation, the medium was replaced with 1 mL of medium containing D-2a (diluted from the stock solution immediately prior to use). Petri dishes were incubated at 37° C. for two hours. Next, dishes were removed from the incubator and titled on a bench to visualize the pericellular hydrogel. Prior to co-incubation with phosphatase inhibitors, cells were washed three times with medium containing Pierce phosphatase inhibitor cocktail (Thermo) (contains sodium floride, sodium orthovanadate, sodium pyrophosphate, and beta-glycerophosphate). Next, 1 mL of medium containing both the inhibitor cocktail and D-2a was applied to the cells.

Conditioned Medium:

$2\times10^5$ of cells in exponential growth phase were seeded in a 35 mm Petri dish with 1 mL complete culture medium. Following overnight incubation, 1 mL of new medium was replaced and incubated for 24 h at 5% $CO_2$, 37° C. The medium was next removed and centrifuged at 10,000 rpm for 5 minutes. The suspension was placed into a 1.5 mL Eppendorf® tube and stored at −20° C. Stored conditioned medium was thawed and warmed to 37° C. in water bath immediately before use.

Transmission Electron Microscopy ("TEM"):

Carbon coated copper grids were glow-discharged to increase their hydrophilicity prior to use. Pericellular hydrogel/nanofibrils were obtained by incubating D-2a at 280 µM with HeLa cells for 2 hours. Cell culture medium was removed in order to expose the pericellular hydrogel. The carbon coated side of the grid was gently pressed onto the pericellular hydrogel for 1 second. Next, the sample-loaded surface was washed using a drop of $ddH_2O$. To remove excess water from the grid, the edge of the grid was immediately tilted and blotted three times against a filter paper. The grid was stained by letting the grid touch a drop of 2.0% (w/v) uranyl acetate with the sample-loaded surface. Excessive stain solution was removed by gently touching the grid with a drop of $ddH_2O$. The grid was then dried by touching the edge of the grid with a filter paper for 3 times. The grid was air dried for a few minutes and examined immediately.

Scanning Electron Microscopy ("SEM"):

Cells in exponential growth phase were seeded in glass bottomed 35 mm Petri dishes at a concentration of $2\times10^4$ cells/well and allowed to attach for 24 hours (37° C., 5% $CO_2$). Next, the cell culture medium was replaced with culture medium containing D-2a. Cells were incubated for an additional 12 hours. Cells were washed three times with PBS. Excess solution was removed by touching a filter paper to the edge of the dish. Holding the edge of the plastic dish using a set of long tweezers, the dish was immersed into liquid $N_2$ for 5 seconds (the glass cracks during the freezing) and quickly transferred into a freeze dryer. After drying overnight, the dish was removed from the freeze dryer. The glass bottom was carefully detached from the dish using tweezers, and placed in a sputter coater for coating of gold (2 nm thick). The coated glass was imaged immediately.

Confocal Microscopy:

Cells in exponential growth phase were seeded in a glass bottomed culture chamber at $2\times10^4$ cells/well. Cells were allowed to attach for 24 hours at 37° C., 5% $CO_2$. The culture medium was removed, and replaced with culture medium containing D-2a at 280 µM. Following 12 hours of incubation, cells were washed 3 times with PBS prior to being stained with 0.1 mg/mL Congo red and 0.6 µM DAPI in PBS buffer (30 minutes at 37° C. in the dark). Next, cells were rinsed three times with PBS, and then kept in PBS for imaging.

Cell Migration Assay:

Cell migration was evaluated using the wound healing assay with the CytoSelect™ Wound Healing Assay Kit (Cell Biolabs, Inc). Wound healing inserts with width at 0.9 mm were placed into 24-well plates. 0.8 mL of HeLa cells at $2\times10^5$ cells/mL were added to either side of the insert and incubated overnight to form a confluent layer. Inserts were then carefully removed to expose the gap. After removing the culture medium, new medium containing the molecules was added to cells. The cells were next incubated at 37° C., 5% $CO_2$ for 18 hours. Images of gaps before and after the addition of the molecules were captured using a microscope at a magnification of ×40. Cell migration was quantified by measuring the change in gap distance.

Cell Adhesion Assay:

Cells in exponential growth phase were detached using 0.25% trypsin-EDTA. After neutralizing trypsin by addition of complete culture medium, the cells were collected by centrifuge (1000 rpm, 3 min). The cell pellet was suspended by addition of culture medium to a concentration of $4×10^5$ cells/mL. 1 mL of the cell suspension was mixed with 1 mL of 2×D-2a or D-2b containing culture media. The resulting solutions were added into 96 well plate at 100 μL/well. After the desired time of incubation at 37° C., 5% $CO_2$, the solution was gently removed, and then 100 μL of culture medium and 10 μL of 5 mg/mL MTT were added to each well. Following 4 hour incubation in the dark, 100 μL of 10% SDS with 0.01M HCl was added to each well to stop the reduction reaction and to dissolve the purple. After incubation of the cells at 37° C. for overnight, the viability was measured. Data represent the mean±standard deviation of three independent experiments.

Phosphatase Activity Assay:

Phosphatase activity was evaluated by the alkaline phosphatase assay using the Abcam Alkaline Phosphatase Assay Kit following the supplied protocol. In brief, 50 μL of 5 mM pNPP solution in assay buffer was mixed with 80 μL of the sample solutions in 96 well plate. The mixed solution was incubated at 25° C., protected from light. 20 μL of stop solution was added to each test and the OD at 405 nm of the solution was measured in a microplate reader.

Cell Viability Assay:

Cells in exponential growth phase were seeded in a 96 well plate at a concentration of $2×10^4$ cells/well. The cells were allowed to attach to the wells for 24 hours at 37° C., 5% $CO_2$. The culture medium was removed and 100 μL culture medium containing compounds (immediately diluted from fresh prepared stock solution of 10 mM) at gradient concentrations (0 μM as the control) was placed into each well. After culturing at 37° C., 5% $CO_2$ for 48 hours, each well was added by 10 μL of 5 mg/mL MTT (3-(4,5-dimethylthiazoL-2-yl)-2,5-diphenyltetrazolium bromide), and the plated cells were incubated in the dark for 4 hours. 100 μL 10% SDS with 0.01M HCl was added to each well to stop the reduction reaction and to dissolve the purple. After overnight incubation of the cells at 37° C., the OD at 595 nm of the solution was measured in a microplate reader. Data represent the mean±standard deviation of three independent experiments.

Apoptosis Pathway Assay:

The apoptosis pathway was evaluated using the PathScan® Apoptosis Multi-Target Sandwich ELISA Kit (Cell Signaling Technology) following the supplied protocol. Cells in exponential growth phase were seeded in a 6 cm Petri dish at a concentration of $10×10^5$ cells/dish (5 dishes). Cells were allowed to attach to the wells for 24 hours at 37° C., 5% $CO_2$. The culture medium was removed and 5 mL medium containing 280 μM D-2a (immediately diluted from fresh prepared stock solution of 11.2 mM) was placed into each dish. At 0, 6, 12, 24, or 32 hours, the medium was removed and cells were washed three times with cold PBS buffer. 0.9 mL lysis buffer was used to lyse cells in each dish, and 0.9 mL of diluents buffer was used to dilute each of the cell lysate. The lysate was incubated in the provided 96 well plate at 4° C. for 24 hours.

Example 1

Phosphatase-Catalyzed Dephosphorylation of D-2a Results in Localized Self-Assembly of Pericellular Hydrogels/Nanonets on the Surface of Cancer Cells Napthalene capped tripeptide precursor molecule D-2a and hydrogelator molecule D-2b, synthesized according to Yang et al. (*Small* 3:558-562 (2007), which is hereby incorporated by reference in its entirety), are comprised of the tripeptide D-Phe-D-Phe-D-Tyr (FIG. 1B). The D-Tyr of D-2a is phosphorylated (FIG. 1B). Alkaline-phosphatase ("ALP") catalyzed dephosphorylation of precursor molecule D-2a (0.20 wt %/2.77 mM) forms hydrogelator molecule D-2b (0.18 wt %/2.77 mM), which self assembles to form the nanofibrils of a hydrogel.

Figures 2A, 2B, 2C, 2D:
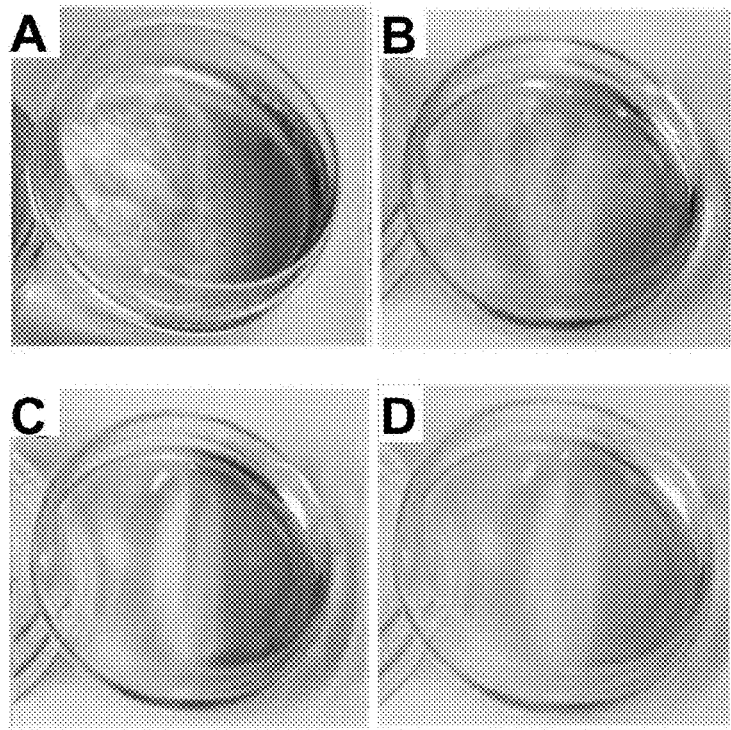
FIGS. 2A-2G are images illustrating the enzymatic formation of the hydrogel/nanonets on the cells.

Unexpectedly, treatment of a confluent layer of HeLa cells with either 560 or 280 μM D-2a (2 hours at 37° C.) results in the formation of a hydrogel-like soft material (hydrogel) on the cell surface (FIGS. 2A, 2B). Little hydrogelation was observed when cells were treated with 140 μM D-2a (FIG. 2C).

Liquid chromatography-mass spectrometry ("LC-MS") analysis revealed that the hydrogel of FIG. 2A contained D-2b at a concentration of approximately 2.05 mM (Table 1), which is higher than the concentration of D-2a initially used for the treatment of the HeLa cell monolayers (500 μM D-2a) (FIG. 2A, Table 1). This result indicates that the conversion of D-2a to D-2b leads to the pericellular accumulation of D-2b for hydrogelation on the surface of HeLa cells. In contrast, incubation of HeLa cells with D-2b at a concentration as high as 560 μM resulted in hardly any hydrogelation (FIG. 2D), further suggesting that phosphatase-catalyzed dephosphorylation of D-2a results in localized self-assembly of D-2b in the pericellular space for hydrogelation. This notion agrees with the finding that phosphatase inhibitors (Pierce™) prevent formation of the pericellular hydrogel on the surface of HeLa cells (FIG. 5A).

TABLE 1

Conversion and degradation of D-2a and L-2a. Composition of the pericellular hydrogel/nanofibrils and the suspension medium of HeLa cells after incubation with D-2a or L-2a at 560 μM at 37° C. for 12 hours.

| Precursor | Pericellular hydrogel (μM) | Suspension medium (μM) | |
|---|---|---|---|
| D-2a | D-2b | D-2b | |
|  | 2053.9 | 502.5 | |
| L-2a | [a]N/A | L-2b | L-3 |
|  |  | 176.6 | 270.4 |

[a]N/A: no pericellular hydrogel/nanofibrils detected.

Example 2

The Phosphatase Gradient Promotes Dynamic Pericellular Hydrogelation

Figures 4A, 4B, 4C, 4D:
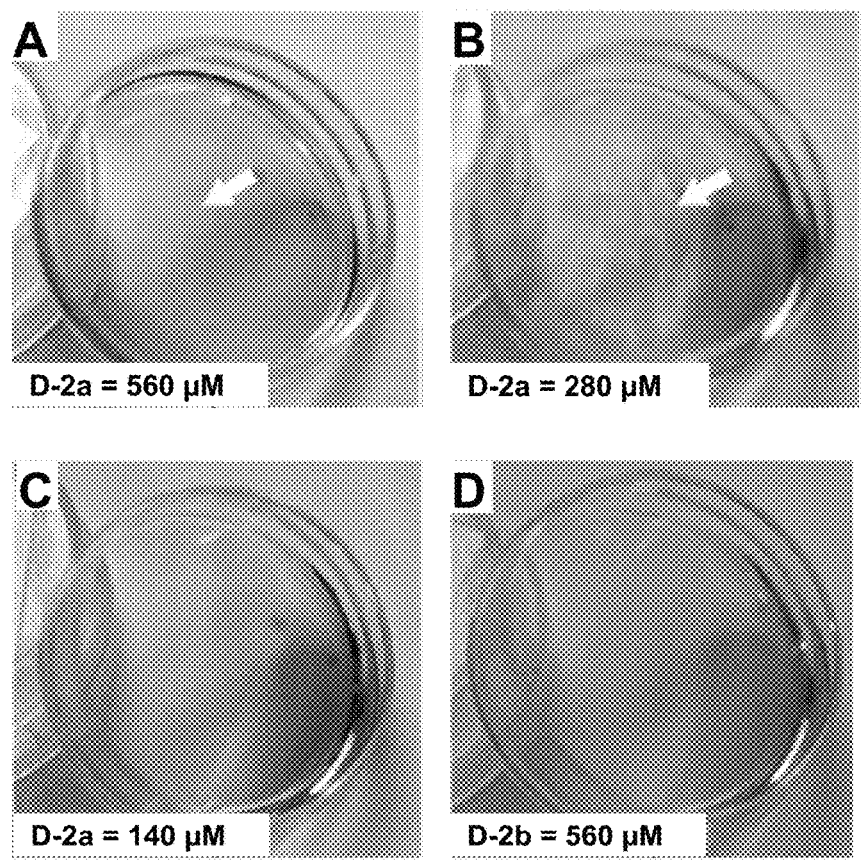
FIGS. 4A-4D are optical images of HeLa cell conditioned medium.

HeLa cell conditioned medium ("CM") dephosphorylates D-2a to form D-2b nanofibrils. CM treated with either 560 or 280 μM D-2a for 48 hours completely transforms from a solution to a hydrogel (FIGS. 4A, 4B). Similar to experiments conducted with HeLa cells incubated with either 140 μM D-2a or 560 μM D-2b for two hours (FIGS. 2C-2D), CM containing either 140 μM D-2a or 560 μM D-2b fails to form a hydrogel following 48 hours of incubation (FIGS. 4C-4D).

These results confirm that the secretory phosphatases present in HeLa cell conditioned medium are sufficient to convert D-2a to D-2b, thereby contributing to the formation of a hydrogel.

Since surface and secretory phosphatases are present on or near the cell membrane, the concentration of phosphatases is expected to be high in the pericellular space, resulting in the selective formation of pericellular hydrogels following incubation with D-2a. The homogenous distribution of D-2b in the CM would not be expected to produce pericellular hydrogels. Direct incubation of CM with 560 µM D-2b for 48 hours allows for the even distribution of D-2b throughout the CM (FIG. 4D), similar to what is seen when HeLa cells are directly incubated for 2 hours with 560 µM D-2b. Thus, direct incubation of HeLa cells with D-2b does not form pericellular hydrogels. Moreover, incubation of HeLa cells with 560 µM D-2a in the presence of ALP (0.1 U/mL) for 2 hours results in hardly any pericellular hydrogelation (FIG. 5B), indicating that the phosphatase gradient promotes the dynamics of the pericellular accumulation of the hydrogelators (i.e., D-2b).

Example 3

Pericellular Hydrogels Consist of Networks of Nanofibrils which Form Nanonets

Figure 2E:
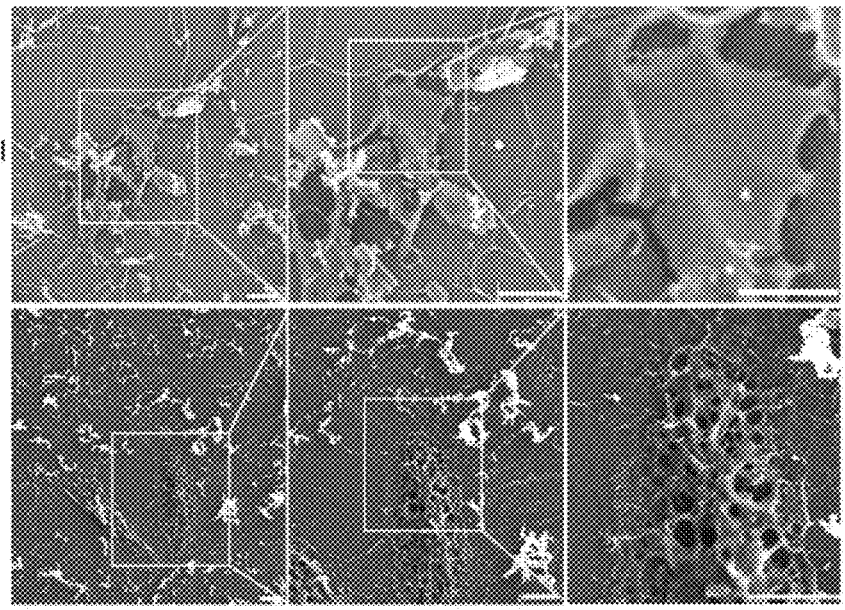

SEM reveals that the surface of the HeLa cells incubated with D-2a differs from the surface of untreated HeLa cells. Since the organic solvents traditionally used for cell fixation and washing cell monolayers (i.e., alcohol or acetone) destroy the supramolecular structure of the nanofibrils within the hydrogels, cell monolayer samples were instead freeze-dried for SEM analysis. While untreated HeLa cells exhibit a smooth surface (FIG. 2E, top), cells treated with 560 µM D-2a are covered in porous structures (i.e., nanonets) (FIG. 2E, bottom). Additionally, cells treated with 280 µM D-2a display fiber-like structures attached closely to the cell surface (FIG. 6). These results coincide with the pericellular hydrogelation observed on HeLa cells treated with 280 and 560 µM D-2a (FIGS. 2A, 2B).

Figure 2F:
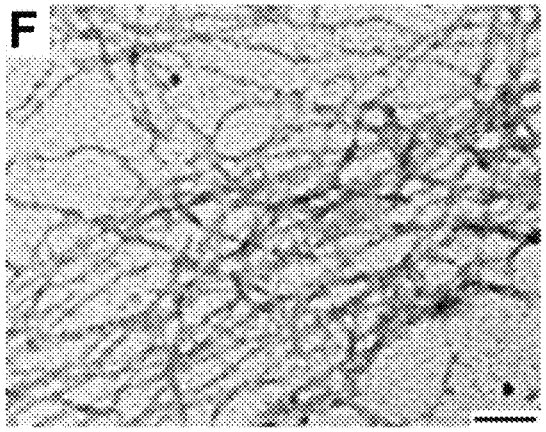
Figure 2G:
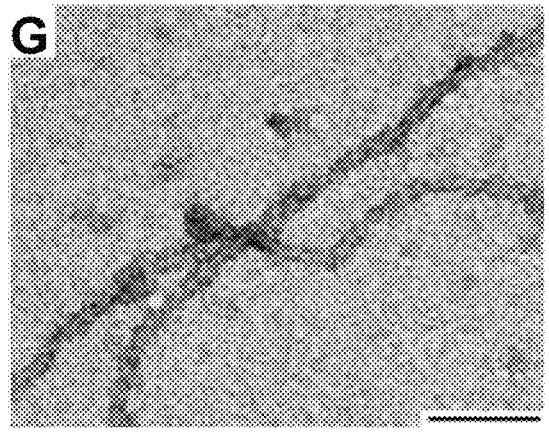

Negative stained TEM of the pericellular hydrogel on HeLa cells treated with 280 µM D-2a reveals that the hydrogel consists of networks of nanofibrils (FIG. 2F) that have diameters of about 20 nm (FIG. 2G). That is, the nanofibrils form nanonets. Similar to the nanofibrils of D-2b formed by the addition of ALP into the solution of D-2a in PBS buffer (FIG. 7), these cell-surface nanofibrils entangle with each other to form the matrices of the hydrogel. Moreover, negative staining TEM shows the rough dark edges on the pericellular nanofibrils (FIG. 2G), indicating that other biomacromolecules likely attach to the nanofibrils.

Example 4

Figures 3A, 3B, 3C:
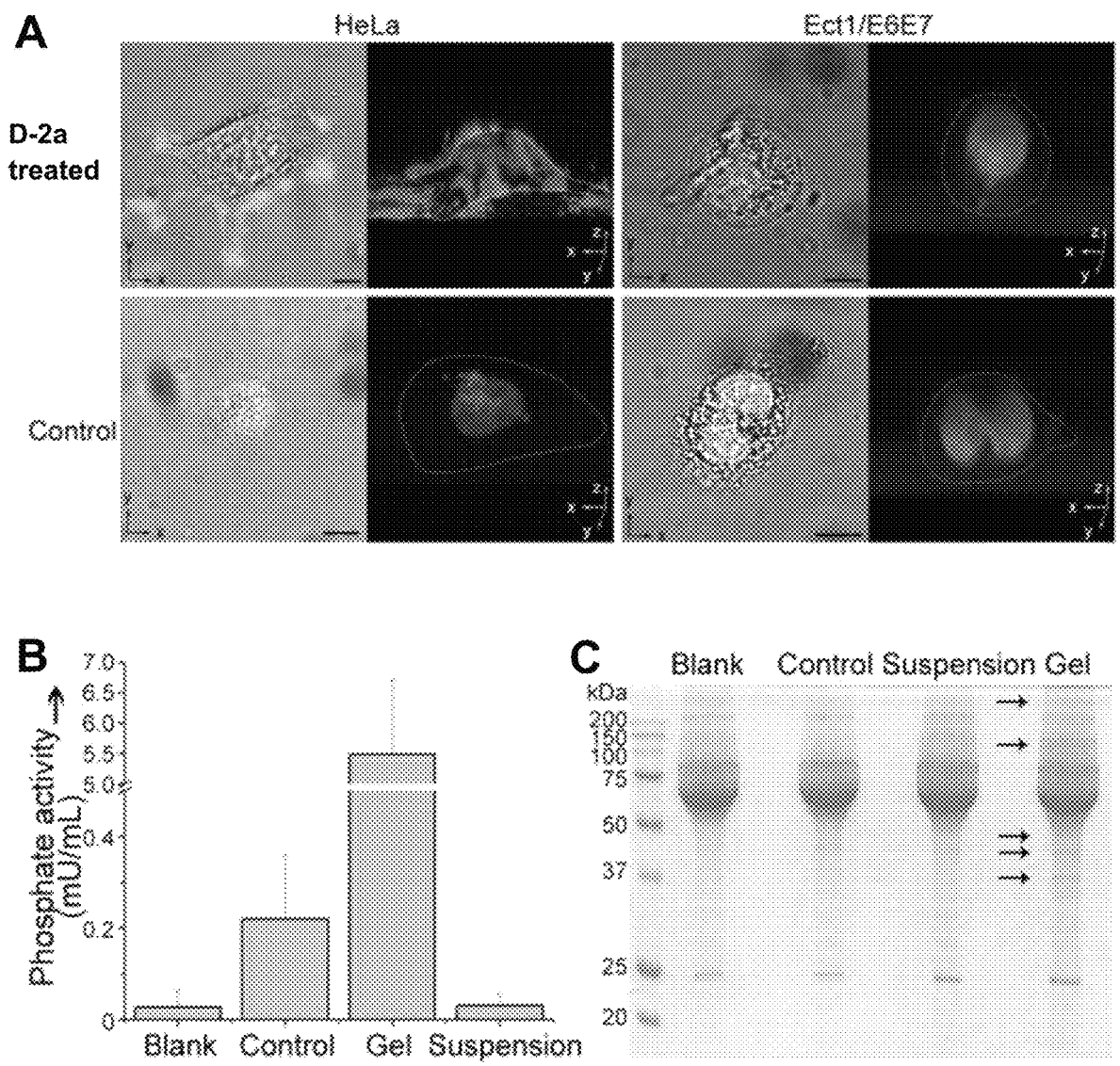
FIGS. 3A-3E illustrate the inhibition of cancer cells by pericellular hydrogel/nanonets.

ALP-Catalyzed Hydrogel/Nanonets Form Exclusively in the Pericellular Space and Prevent the Diffusion of DAPI into Cells Pericellular nanofibrils and cellular nuclei can be visualized using Congo red and DAPI, respectively (Kapuscinski, *Biotech. Histochem.* 70:220-233 (1995); Binder et al., *Angew. Chem. Int. Ed.* 45:7324-7328 (2006), each of which is hereby incorporated by reference in its entirety). The left panels of FIG. 3A shows images of HeLa cells either treated or untreated with 280 µM D-2a for 12 hours, followed by staining with Congo red/DAPI. D-2a treated HeLa cells show fluorescence (red) that outlines the cell shape, while untreated HeLa cells (i.e., the control) show little fluorescence (FIG. 3A, bottom left). Moreover, DAPI is unable to enter D-2a treated HeLa cells and instead co-localizes with Congo red, as shown in both the 2-D image and the 3-D stacked image (FIG. 3A, top left). This result differs drastically from the staining of the untreated HeLa cells (i.e., DAPI stains the nuclei) and confirms that (i) the hydrogel/nanonets form exclusively in the pericellular space and (ii) the pericellular hydrogels/nanonets prevent the diffusion of DAPI into the cells.

Since DAPI is a small molecule (M.W.=277 Da), the blocking of DAPI cell entry indicates that the pericellular hydrogel/nanonets are able to block other molecules (e.g., biomacromolecules) from entering cells. The uneven distribution of the Congo red on the surface of the D-2a treated HeLa cells agrees with the result from SEM, indicating inhomogeneous distribution of the hydrogel on the surface of the HeLa cells.

Figure 9:
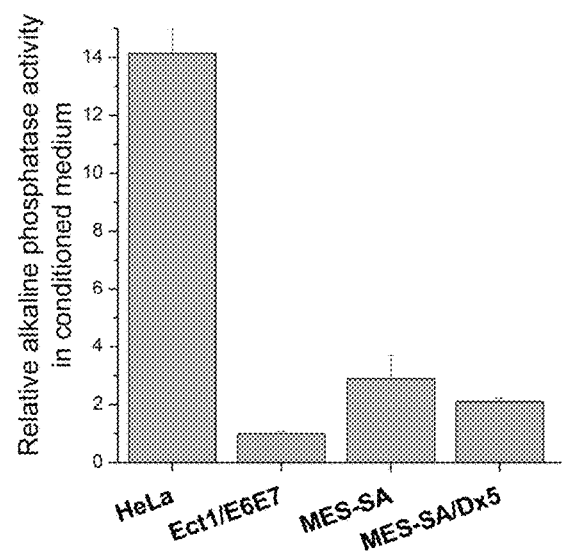
FIG. 9 is a bar graph that illustrates the amount of phosphatases in the conditioned media of HeLa, Ect/E6E7, MES-SA, and MES-SA/Dx5 cells.

Ect1/E6E7 cells (immortalized normal human cervical epithelial cells, which have same tissue and organ origins as HeLa cells) were treated with the same procedure as described for HeLa cells above. The Ect1/E6E7 cells, after being incubated for 12 hours with 560 µM D-2a, hardly display any red fluorescence (FIG. 3A, top right), which is similar to that of the untreated Ect1/E6E7 cells (FIG. 3A, bottom right). Furthermore, DAPI stains the nuclei of both the treated and the untreated Ect1/E6E7 cells (FIG. 3A, right panels). These results agree with the finding that hydrogels hardly form on Ect1/E6E7 cells, even following a prolonged incubation time of 48 hours (FIG. 8). The difference of hydrogel/nanonets formation by D-2a conversion to D-2b on HeLa cells and Ect1/E6E7 cells agrees with the notion that HeLa cells have higher levels of phosphatase activity than Ect1/E6E7 cells (FIG. 9).

Example 5

Pericellular Hydrogel/Nanonets Block Cellular Mass Exchange Between Cells and their Environment To verify whether the pericellular hydrogel/nanonets block the entry of secretory proteins/enzymes into the culture medium, the amount of phosphatases in four experimental samples was evaluated: blank medium (Blank), medium incubated with untreated HeLa cells (Control), the pericellular hydrogel from HeLa cells treated with 560 µM D-2a for 12 hours (Gel), and the suspension of the medium of HeLa cells treated with D-2a after removing the hydrogel (Suspension). The amount of phosphatases accumulated in the Gel is about 27 times higher than that found in the Control (FIG. 3B). Consequently, the amount of phosphatases in the Suspension is significantly lower than that in the Control (FIG. 3B). These results indicate that the pericellular hydrogel/nanonets capture the secretory proteins/enzymes from the cells, blocking them from entering the surrounding culture medium. Moreover, analysis of the protein composition in the four samples by SDS-PAGE and Coomassie staining (FIG. 3C) shows that the Gel lane contains more bands than in the lanes of the Control and the Suspension, indicating that the pericellular hydrogel/nanonets block diffusion to enrich secretory proteins. In other words, the pericellular hydrogel/nanonets largely block cellular mass exchange between the cells and their environment.

Example 6

Figures 3D, 3E:
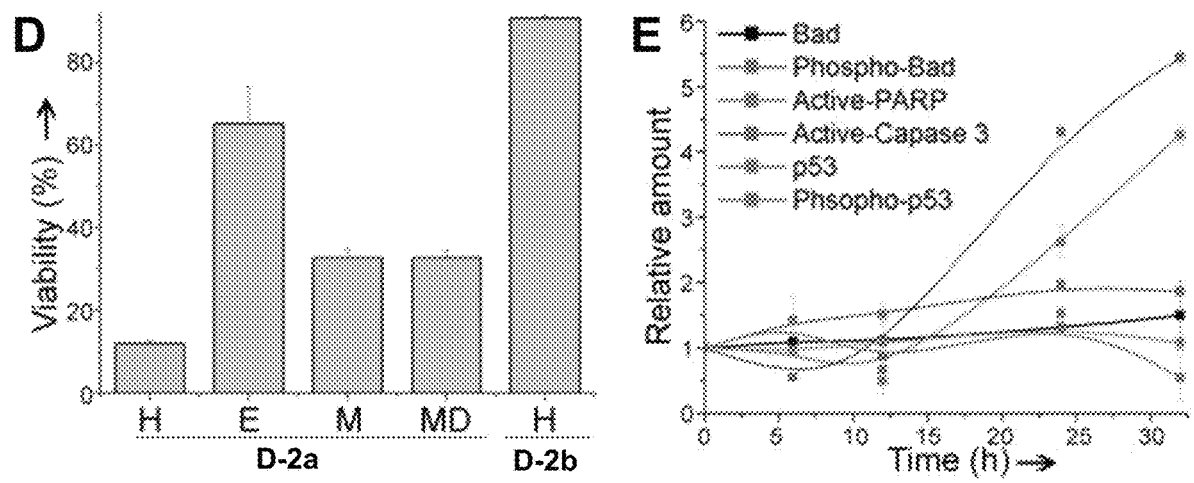
Figures 10A, 10B:
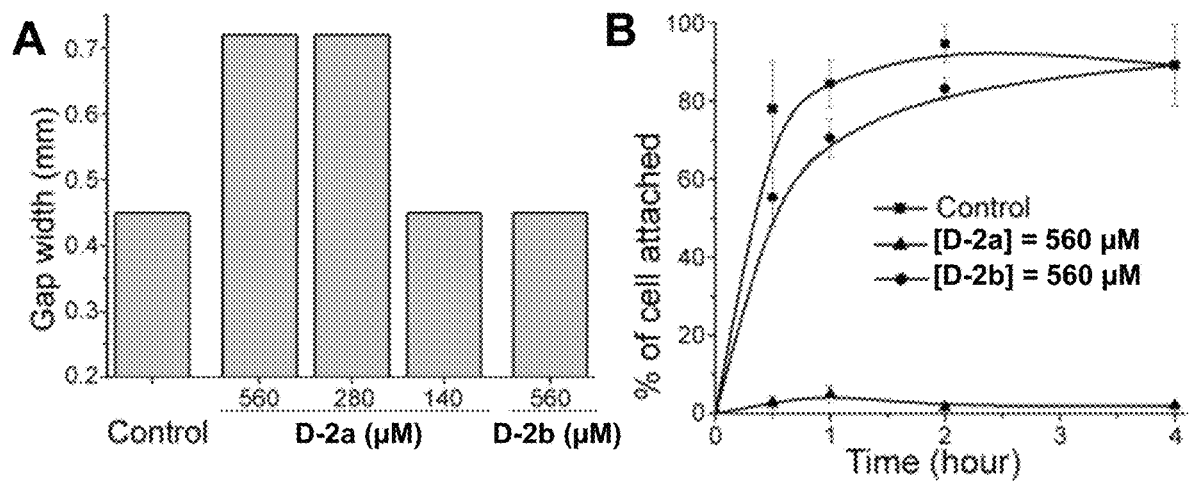
FIGS. 10A-10B illustrate the inhibitory effect of D-2a on HeLa cells.
Figure 11:
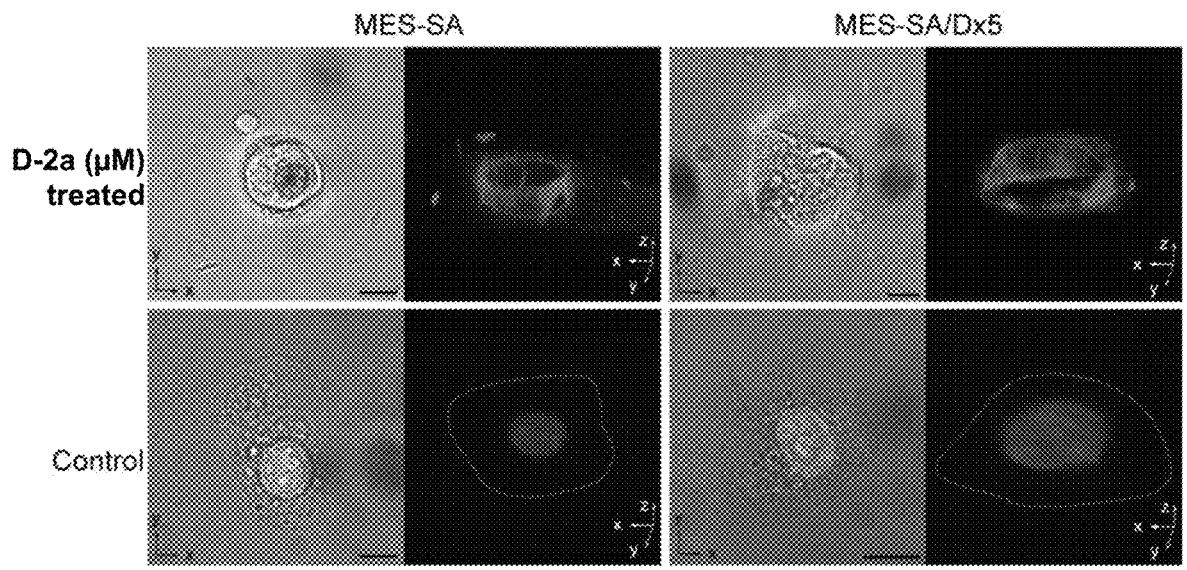
FIG. 11 illustrates overlaid and 3D stacked z-scan images of Congo red and DAPI stained MES-SA and MES-SA/Dx5 cells treated with either 280 µM D-2a (upper panel) or medium alone (control, lower panel) for 12 hours. Scale bar=10 µM. White dots outline the cells.
Figures 12A, 12B:
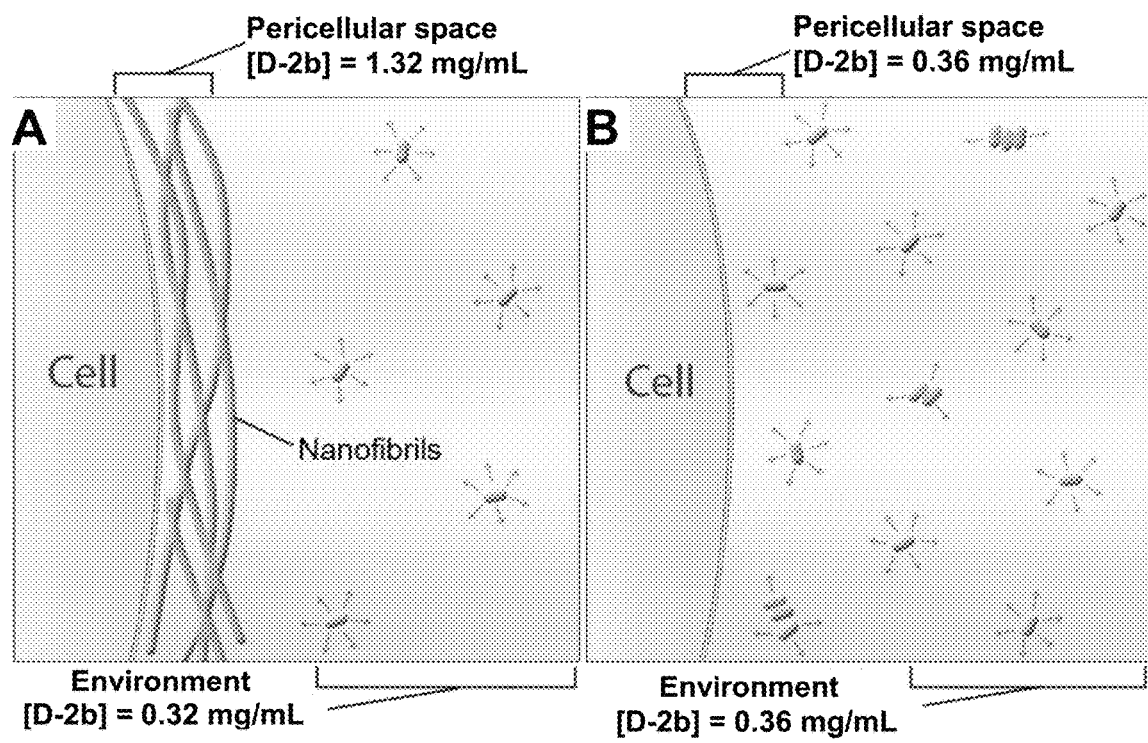
FIGS. 12A-12B illustrate the distribution of D-2b around cells.

Pericellular Hydrogel/Nanonets Affect Cancer Cell Migration, Adhesion, Proliferation, and Viability Blocking cellular mass exchange has profound effects on critical cellular activities (e.g., migration, adhesion, and proliferation) of cancer cells. According to the migration assay (Lauffenburger, *Cell* 84:359-369 (1996), which is hereby incorporated by reference) results (FIG. 10A), HeLa cells treated with either 280 or 560 μM D-2a have gaps larger than those of untreated cells (i.e., control HeLa cells), cells treated with 140 μM D-2a, or cells treated with 560 μM D-2b, confirming that the pericellular hydrogel/nanonets decrease the migration of the HeLa cells. Moreover, as shown by the time progression curve of the cell adhesion (FIG. 10B) of trypsinized HeLa cells (Humphries, in *Extracellular Matrix Protocols, Vol.* 522 (Eds.: S. Even-Ram, V. Artym), Humana Press, pp. 203-210 (2009), which is hereby incorporated by reference), the addition of 560 μM D-2a significantly delays the adhesion of HeLa cells (i.e., less than 5% cells reattach to surface after at 4 hours). The addition of 560 μM D-2b, though exhibiting a slight delay of adhesion at the beginning of incubation, hardly hampers cell adhesion (e.g., being similar to that of control, more 80% of cells reattach at 4 hours). Most importantly, as shown in FIG. 3D, 280 μM D-2a significantly decreases the viability of the HeLa cells to about 10% following 48 hour incubation. Moreover, 280 μM D-2a also forms pericellular hydrogel/nanonets (FIG. 11) and inhibits the growth of MES-SA and MES-SA/dx5 cells, regardless of the multi-drug resistance of the latter. In contrast, over 60% of the Ect1/E6E7 cells treated with 280 μM D-2a for 48 hours remain viable (FIG. 3D). The direct addition of 280 μM D-2b hardly inhibits the growth of HeLa cells. These results confirm that the pericellular dephosphorylation of D-2a leads to the self-assembly of D-2b on the surface of cancer cells, thus the network of nanofibrils on the cancer cells inhibits the viability of the entrapped cells (FIGS. 12A, 12B).

ELISA was used to quantify the amount of several key apoptosis signal molecules over time in the HeLa cells incubated with 280 μM D-2a (FIG. 3E). The amount of active Caspase 3 and active PARP was found to increase significantly at 24 and 32 hours of incubation, indicating that the cells undergo mitochondria mediated apoptosis.

Figures 13A, 13B:
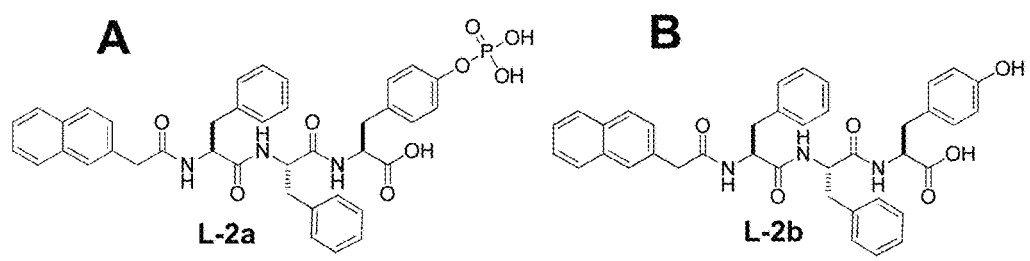
FIGS. 13A-13B illustrate the chemical structures of the L-2a (FIG. 13A) and L-2b (FIG. 13B), enantiomers of D-2a and D-2b, respectively.
Figures 14A, 14B:
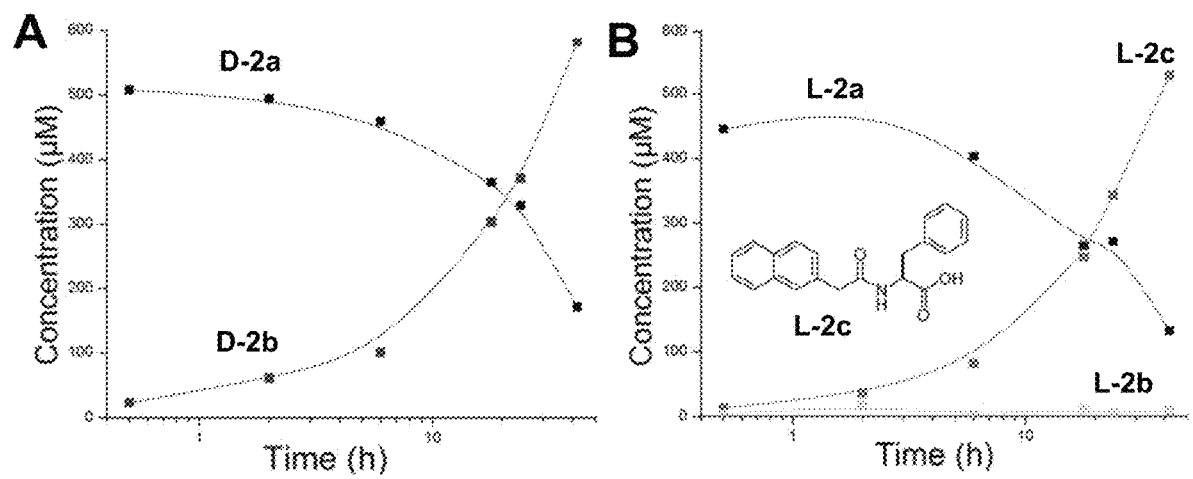
FIGS. 14A-14B are graphs illustrating that the formation (and maintenance) of pericellular hydrogel/nanofibrils is dependent on the biostability of the molecules.
Figure 15:
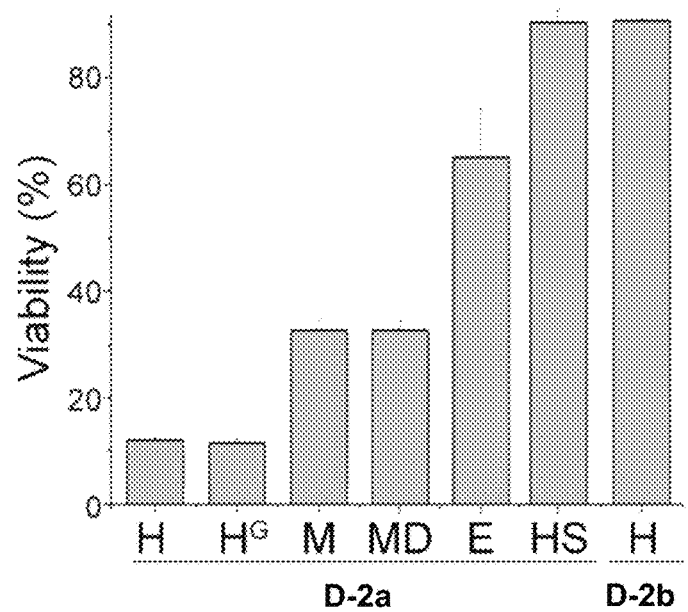
FIG. 15 is a bar graph illustrating the cell viabilities of HeLa ("H"), MES-SA ("M"), MES-SA/Dx5 ("MD"), and Ect1/E6E7 ("E") treated with 280 µM D-2a; HeLa/GFP ("$H^G$") and HS-5 ("HS") cells treated with 300 µM D-2a; or HeLa cells treated with 280 µM D-2b for 48 hours.

One key prerequisite for pericellular hydrogelation is the proteolytic stability of the small molecular precursors and hydrogelators. Incubation of HeLa cells with 560 μM L-2a, the L-peptide counterpart of D-2a (FIGS. 13A-13B), at 37° C. fails to form pericellular hydrogel/nanofibrils due to the proteolysis of L-2a in cellular environment (FIGS. 14A-14B).

Discussion of Examples 1-6

Besides serving as important internal components (e.g., cytoskeletons) of cells, fibrils outside the cells also bear significant functions. For example, fibrils formed by polysaccharides and fibrous proteins, such as fibronectin, collagens, and laminins (Persikov et al., *Proc. Natl. Acad. Sci. U.S.A.* 99:1101-1103 (2002), which is hereby incorporated by reference), afford networks that withhold extracellular fluid, and the resulting extracellular matrix maintains multicellular structures and mediates cell-to-cell communication (Mann, *Angew. Chem. Int. Ed.* 47:5306-5320 (2008), which is hereby incorporated by reference in its entirety). A recent study demonstrated that human α-defensin 6 ("HD6") self-assembles in contact with bacteria surface protein to form nanonets that entrap the bacteria and block their translocation (Chu et al., *Science* 337:477-481 (2012), which is hereby incorporated by reference in its entirety). The various functionalities of extracellular fibrils and networks formed by biomolecules suggest that it is feasible to build xenogenous fibrils extracellularly (e.g., in the pericellular space) as a new approach for regulating the interaction of cell with its microenvironment (lida et al., *Science* 342: 967-970 (2013), which is hereby incorporated by reference in its entirety), thus controlling the fate of cells.

Like self-assembling peptides and proteins, certain small organic molecules self-assemble (Lehn, *Science* 295:2400-2403 (2002); Whitesides et al., *Science* 295:2418-2421 (2002), each of which is hereby incorporated by reference in its entirety) in water to afford nanofibrils as matrices of hydrogels (Estroff, *Chem. Rev.* 104:1201-1217 (2004); Zhang et al., *Angew. Chem. Int. Ed.* 51:7011-7015 (2012); Kiriya et al., *Angew. Chem. Int. Ed.* 51:1553-1557 (2012); Tamesue et al., *Angew. Chem. Int. Ed.* 49:7461-7464 (2010), each of which is hereby incorporated by reference in its entirety), e.g., in response to biostimuli such as enzymes (Yang et al., *Adv. Mater.* 16:1440-1443 (2004); Toledano et al., *J. Am. Chem. Soc.* 128:1070-1071 (2006); Yang et al., *Acc. Chem. Res.* 41:315-326 (2008); Yuan et al., *Angew. Chem. Int. Ed.* 52:976-979 (2013); Kumar et al., *Angew. Chem. Int. Ed.* 50:9343-9347 (2011), each of which is hereby incorporated by reference in its entirety). Interestingly, a vancomycin-pyrene conjugate, which self-assembles in water to form nanofibrils (Xing et al., *J. Am. Chem. Soc.* 124:14846-14847 (2002), which is hereby incorporated by reference in its entirety), exhibits two orders of magnitude enhanced antibacterial activity against vancomycin resistant enterococci (VRE), plausibly through self-assembled multivalent vancomycin binding the receptors on bacterial cell wall (Xing, *Chem. Commun.* 2224-2225 (2003), which is hereby incorporated by reference in its entirety). However, the observation of xenogenous nanofibrils on mammalian cells has yet to be reported. While researching enzyme catalyzed self-assembly of D-peptide derivatives (Li et al., *J. Am. Chem. Soc.* 135:542-545 (2013); Li et al., *J. Am. Chem. Soc.* 135: 9907-9914 (2013), each of which is hereby incorporated by reference in its entirety), the self-assembly of a small D-peptide derivative, surprisingly, was found to form pericellular hydrogel/nanonets. These results of Examples 1-6 report the observation, the origin of formation, and a potential application (i.e., inhibiting cancer cells) for the pericellular hydrogel/nanonets.

FIG. 1A is a schematic representation of the results of Examples 1-6. In particular, these results demonstrate that (i) surface and secretory phosphatases (Wu et al., *Mol. Cell. Proteomics* 9:1100-1117 (2010), which is hereby incorporated by reference in its entirety) from cells catalytically dephosphorylate a small D-peptide derivative (e.g., D-2a) to form a hydrogelator (e.g., D-2b); (ii) the accumulation of the hydrogelator results in a network of nanofibrils as the scaffold of a hydrogel in the pericellular space; (iii) the pericellular hydrogel/nanonets entrap secretory proteins, block cellular uptake, decrease cell migration, prevent cell adhesion, and induce cell apoptosis; and (iv) the overexpression of surface and secretory phosphatases by cancer cells (Fishman et al., *Nature* 219:697 (1968), which is hereby incorporated by reference in its entirety) allows the selective formation of pericellular nanonets on the surface of cancer cells (e.g., HeLa, MES-SA, and MES-SA/Dx). Thus, these results unexpectedly show enzyme-instructed self-assembly (Yang et al., *Acc. Chem. Res.* 41:315-326 (2008), which is hereby incorporated by reference in its entirety) of nanofibrils in the pericellular space, illustrating a new way to control cell fate according to the expression and location of enzymes that regulate the spatiotemporal profiles of molecular nanofibrils.

Example 7

In vivo Use of Peptide D-2a to Treat Uterine Cancer Model

MES-SA/Dx5 cells are an established model cell-line (human uterine sarcoma) for evaluating the efficacy and toxicity of new drugs in vivo.

Nine nude mice were used for experiments to define the tumor growth curve. $1 \times 10^7$ MES-SA/Dx5 cells were implanted into the mice via intraperitoneal injection using a 25 G needle. Three of the tumor-bearing mice were used to define the tumor growth curve with control treatment, and six mice were given D-2a. The mice were injected subcutaneously and peritumorally (6 times, every 3 days starting at Day 1) with either 100 μL of D-2a at 8 μg/μL (800 μg dose or ~32 mg/kg) in PBS buffer (experimental) or 100 μL of PBS buffer (control). Tumor volume measurements were made every three days, also starting on Day 1. Volume of tumors was measured by caliper.

Figures 16A, 16B:
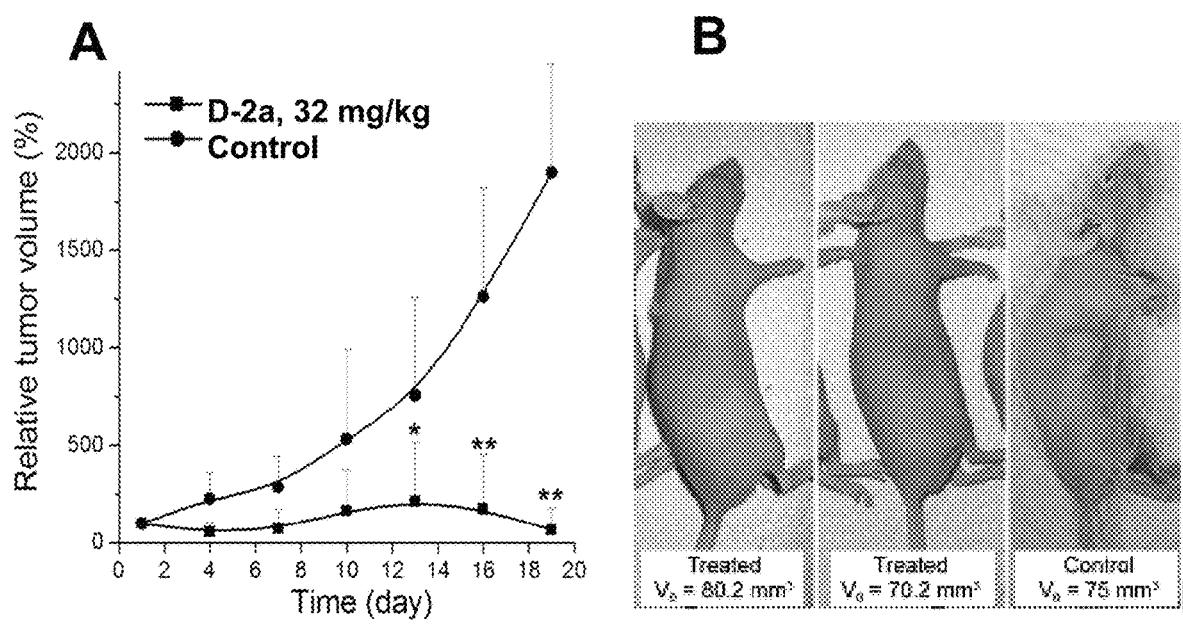

FIG. 16A shows the relative tumor volume in both treated and control mice as a function of time. As can be seen, treatment with D-2a inhibited tumor growth. Statistically significant differences between experimental and control groups were observed by Day 13. This is consistent with the in vitro results demonstrating reduced cell viability following enzymatically induced nanonet formation. FIG. 16B shows images of representative animals treated with D-2a and an untreated control animal, which had similar initial tumor volumes ($V_o$). In the control animal, but not those receiving D-2a, the tumor mass is readily apparent.

Example 8

Pericellular Nanonet/Hydrogel Isolation

Figures 19A, 19B, 19C, 19D:
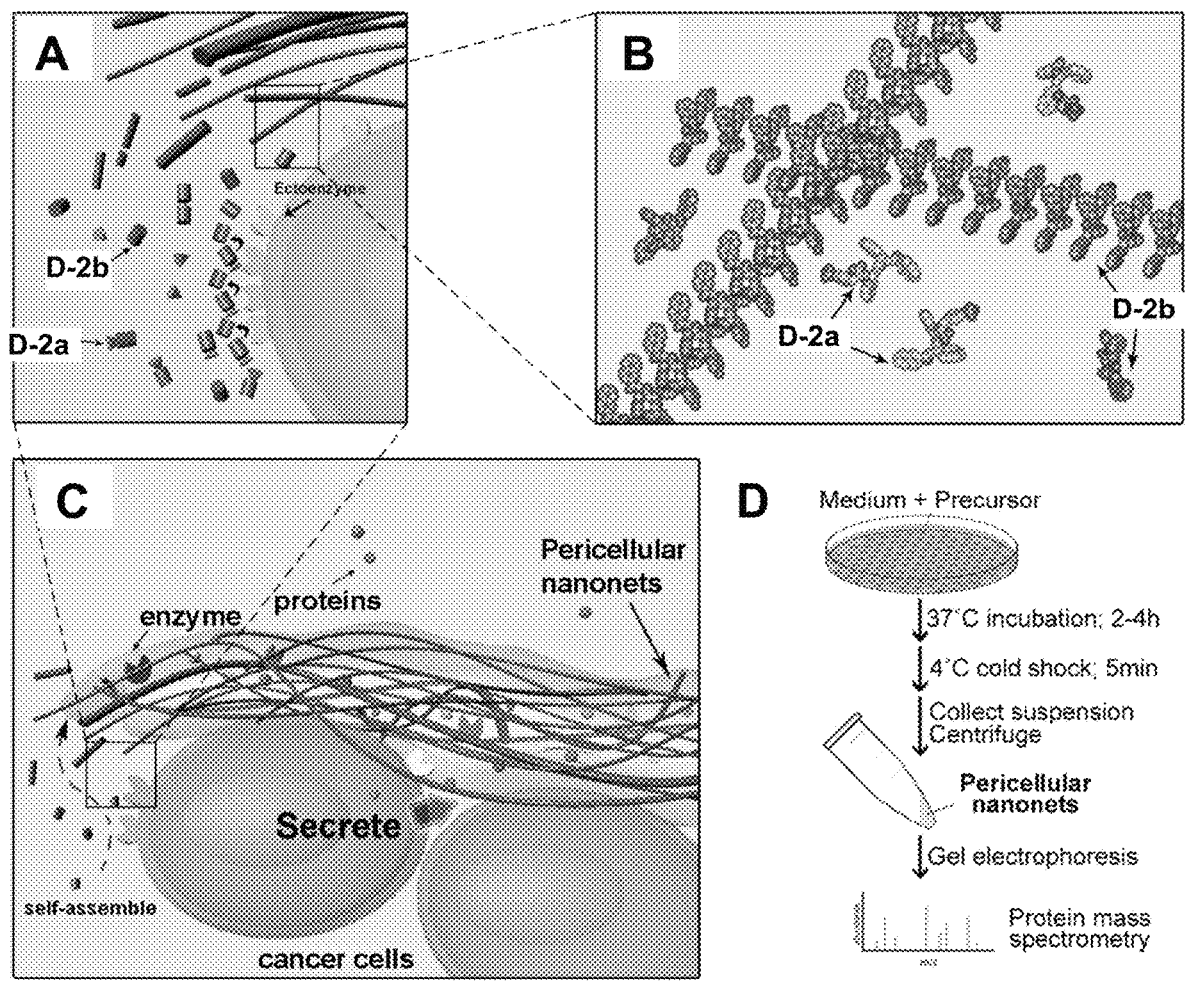
FIGS. 19A-19D schematically illustrate collection of the cancer secretome by pericellular nanonets.

Since pericellular nanonets/hydrogels were able to self-assemble following enzyme-catalyzed activation of the precursor hydrogelator molecule D-1a (FIGS. 32A-32C), applicants developed the slightly more hydrophobic precursor hydrogelator, D-2a (FIG. 1B). As described above, D-2a is a naphthalene ("Nap") capped tripeptide comprising D-amino acids and a phosphorylated tyrosine residue (abbreviated as Nap-D-Phe-D-Phe-D-Tyr(PO$_3$H$_2$); Nap-$^D$F$^D$F$^D$Y$_p$). Phosphatase-catalyzed dephosphorylation converts D-2a to the hydrogelator D-2b (abbreviated as Nap-D-Phe-D-Phe-D-Tyr; Nap-$^D$F$^D$F$^D$Y) (FIG. 1B). Incubation of D-2a with HeLa cells, which overexpress ectophosphatases, enables the formation of hydrogels around the cancer cells following 2 hours of incubation (FIG. 2A). Congo red staining of nanofibrils (Yang et al., *Soft Matter* 2:515 (2007), which is hereby incorporated by reference in its entirety) followed by confocal microscopy confirmed that the nanonets/hydrogel of D-2b form on the surface of cancer cells (FIG. 3A). Moreover, TEM images confirm that nanonets of D-2b act as the matrices of the hydrogel (FIG. 2F). In addition, the amount of phosphatase accumulation in the hydrogel is approximately 27 times higher than in the control (see FIG. 3B), indicating the enrichment of secretory phosphatases in the nanonets/hydrogel. These studies demonstrate that the overexpression of phosphatases by cancer cells (Fishman et al., *Nature* 219:697 (1968), which is hereby incorporated by reference in its entirety) leads to the formation of the pericellular nanonets/hydrogel selectively on the cancer cells and indicate that the pericellular nanonets/hydrogel can sequester other secretory proteins from cancer cells—that is, pericellular nanonets/hydrogel can collect the cancer secretome. In view of these findings (FIGS. 19A-19C), a simple procedure was developed for the isolation of pericellular nanonets from cells in the absence of cell rupture (FIG. 19D).

$3 \times 10^5$ HeLa cells in 2 mL of complete MEM medium were seeded into a 35 mm Petri dish. Following 24 h incubation, the medium was removed, and the cells were washed with 2 mL fresh complete MEM medium once. For collection of medium, the cells were applied with 1 mL of complete MEM medium and were incubated at 37° C. for either 2 or 24 hours. 100 μL of the medium was collected after incubation. For the collection of nanonets/hydrogels, the cells were treated with 1 mL of complete MEM medium containing D-2a (also Nffy(p) or Nap-$^D$F$^D$F$^D$Y$_p$) at 0.4 mg/mL (diluted from a 20× stock solution in PBS buffer). After 2 hour incubation at 37° C., the dish was taken out of incubator and placed in a 4° C. cool room for 5 minutes to cold-shock the cells, thereby inducing cell contraction and detachment of the nanonets. The dish was tilted and knocked on a bench to collect the detached nanonets/hydrogels in medium. Using a wide mouth transfer pipette, the medium was collected into a 1.5 mL Eppendorf® tube and centrifuged at 7500 rpm for 1 minute to separate the nanonets/hydrogel pellet from the cell culture medium (see FIG. 19D). The suspension medium was carefully removed using a 200 μL pipette. For each of the experiments, the samples were obtained from the same batch of cells. After collection, both the medium and the nanonets/hydrogels were immediately frozen at −80° C., and later subjected to analysis (see FIG. 19D).

Example 9

Figure 33A:
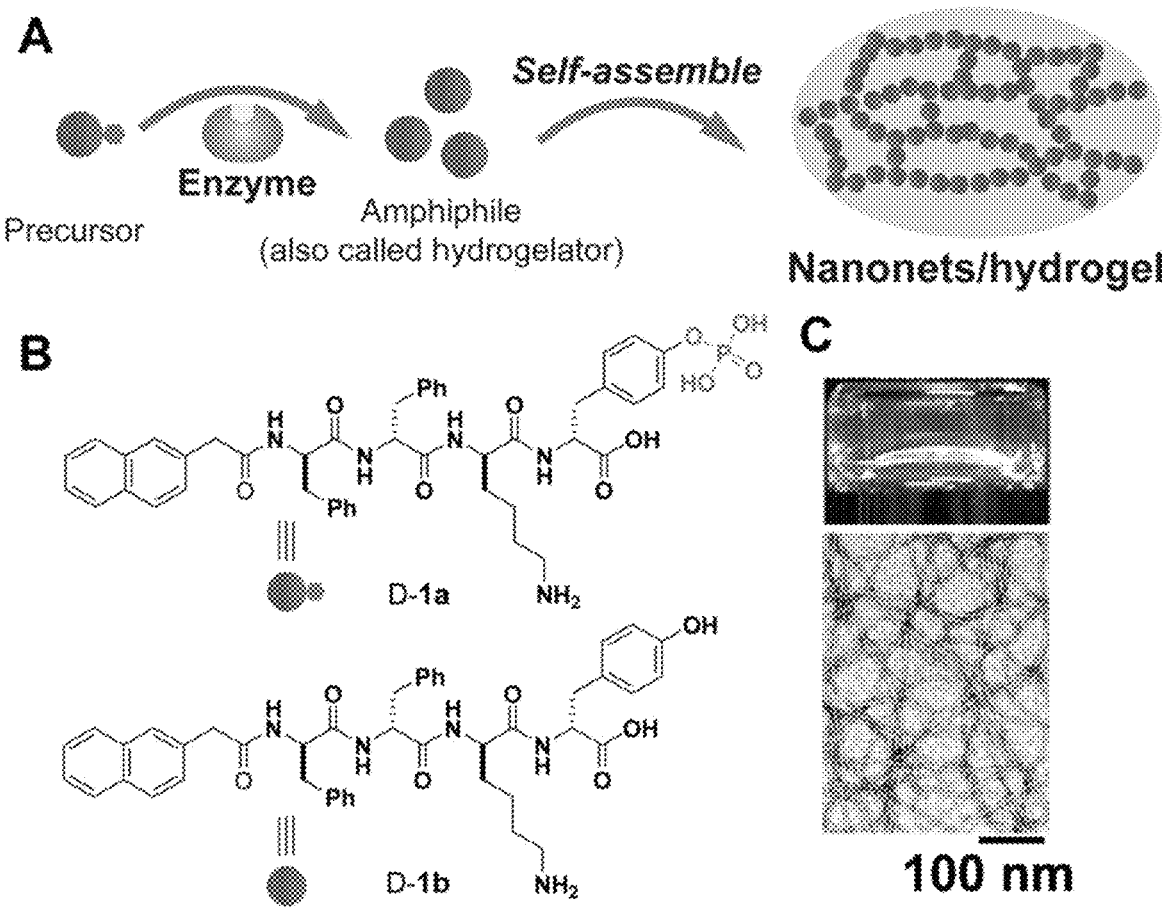
FIGS. 33A-33B show the cell compatibility of the use of nanonets/hydrogel for collecting cancer secretome.

Collection of Pericellular Nanonets within 6 Hours of Incubation with D-2a is Suitable for Collection of the Cancer Secretome from HeLa Cells To select the optimal incubation time for the collection of nanonets/hydrogel, HeLa cells were incubated with D-2a (for 3, 6, or 9 hours, respectively) to allow nanonet formation. The amount of tubulin (an indicator of autolysis) present in the nanonets/hydrogels at various time points was evaluated by Western blot and compared to the amount of tubulin present in conditioned media ("CM") collected following 24 hours of incubation (FIG. 33A). Nanonets collected after either 3 or 6 hours of incubation contain less tubulin than CM (FIG. 33A), which suggests that, within 6 hours of incubation, the nanonets/hydrogel contain less proteins resulting from the autolysis of cells than CM collected at 24 hours. The results also indicate the cell compatibility of the incubation and collection process for nanonets/hydrogel.

Figure 33B:
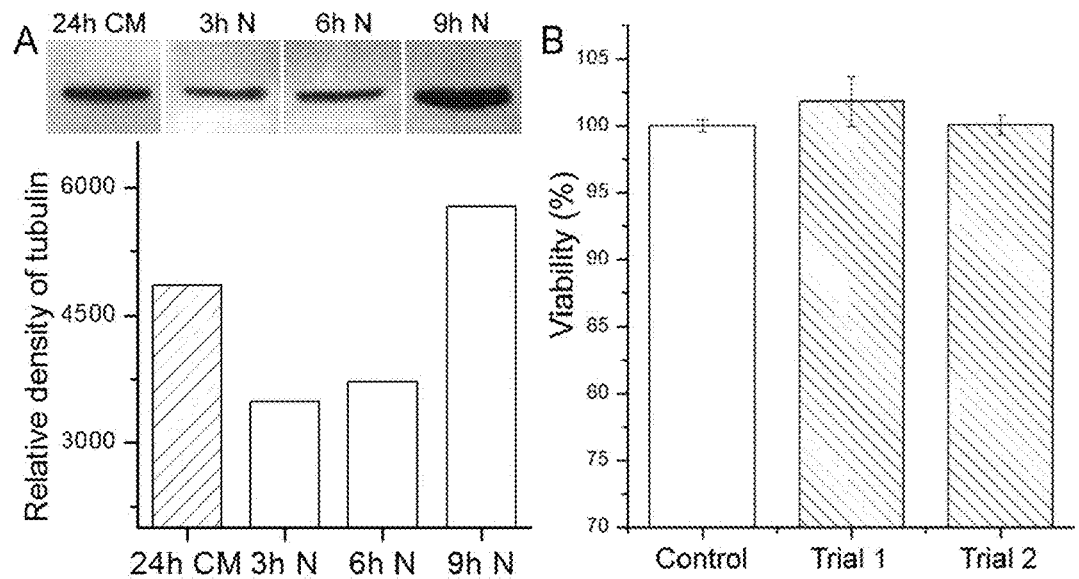

In another experiment the viability of cells following nanonet collection was evaluated following 4 hour incubation with D-2a and cold shock. FIG. 33B shows that the nanonet collection protocol (cold shock and medium removal) hardly affected cell viability. These results, collectively, confirm that cold shock nanonets/hydrogel protocol comprising an incubation time of less than 6 hours is suitable for the collection of the cancer secretome.

Example 10

Pericellular Nanonets/Hydrogel Increase the Yield of Cancer Secretome

Figures 20A, 20B, 20C, 20D, 20E, 20F, 20G, 20H, 20I:
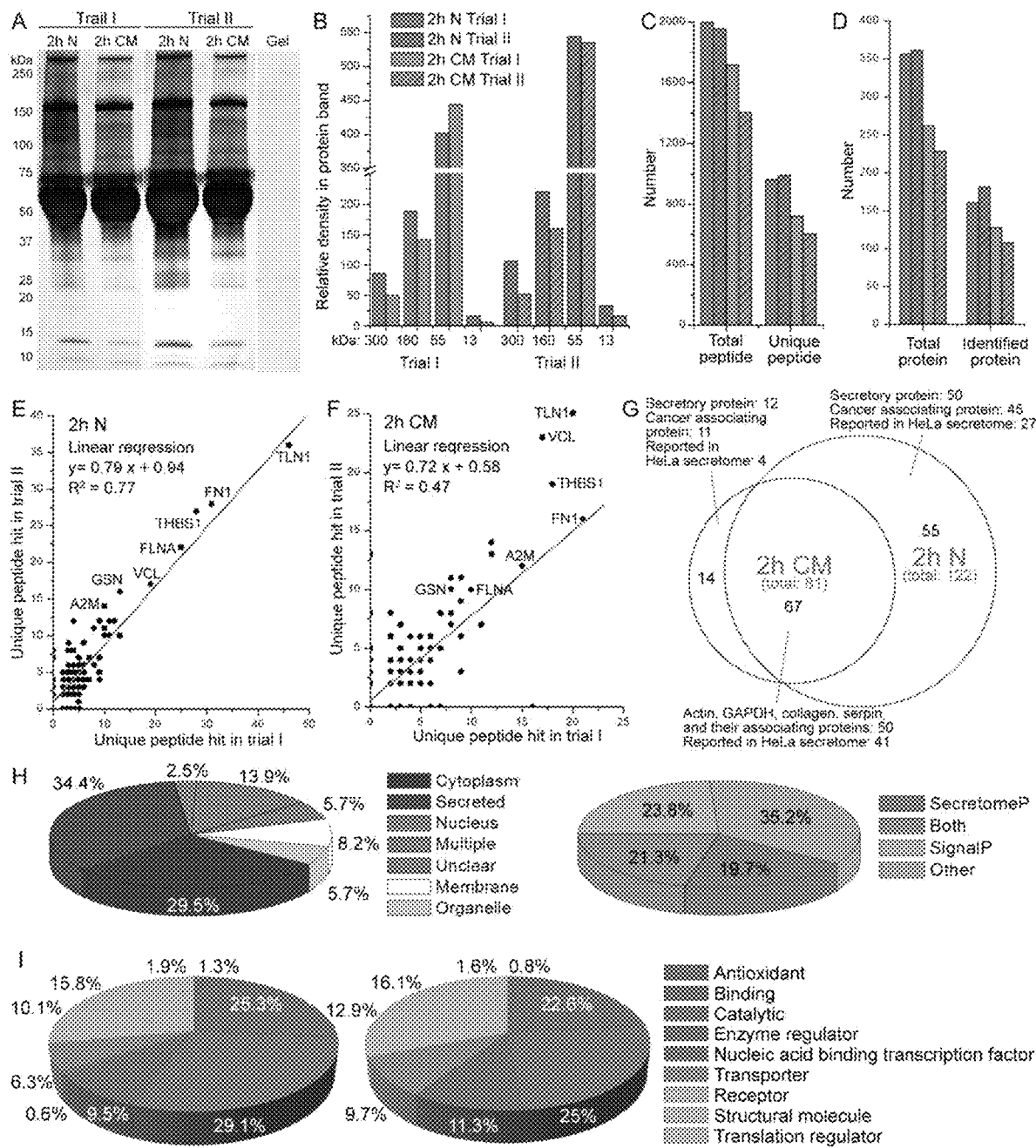
FIGS. 20A-20I show that nanonets collect more secretory proteins with lower pre-analytical variations than culture medium.

To serve as a suitable material for sampling the cancer secretome, the nanonets/hydrogel must collect a similar or greater amount of proteins from the pericellular space of cancer cells than that collected from conditioned media ("CM") of cancer cells. To demonstrate that the nanonets/hydrogels of D-peptides in the pericellular space rapidly collect more secretory proteins than CM, pericellular nanonets/hydrogels were separated from HeLa cells treated with D-2a for 2 hours in complete culture medium ("2 h N"). As a control, HeLa cell CM was collected following 2 hours of incubation in the absence of D-2a ("2 h CM"). Without additional processing, electrophoresis was directly applied to the collected samples. Because they form by non-covalent interactions, the nanonets/hydrogel dissociate into monomeric D-2b upon mixing with Laemmli loading buffer. Due to its small molecular weight (643 Da), D-2b runs out of the agarose gel during electrophoresis and has little effect on gel staining or subsequent proteolytic analysis. Despite being masked by serum proteins (mostly bovine albumins), silver stain of SDS-PAGE gels of the two trials of "2 h N" and "2 h CM", demonstrates that "2 h N" has a darker stain than "2 h CM" (FIG. 20A). Image J (Tan et al., *Opt. Commun.* 281:3013-3017 (2008), which is hereby incorporated by reference in its entirety) analysis of the silver stained gel shows that, in both trials, the bands corresponding to 300, 160, and 13 kDa all have a higher density in the lanes corresponding to "2 h N" than in the lanes corresponding to "2 h CM" (FIG. 20B). These results confirm that there are more proteins in the bands corresponding to "2 h N" than in the bands corresponding to "2 h CM" (FIG. 20B). However, the band corresponding to 55 kDa, consisting mainly of bovine albumin from the culture medium, has a higher density in the "2 h CM" lane than in the "2 h N" lane corresponding to trial 1, whereas the same bands in trial 2 have similar densities. These results indicate that the additional proteins collected by the nanonets are the secretory proteins from HeLa cells rather than the serum proteins from the culture medium, a result that is consistent with the localization of the nanonets/hydrogel at the pericellular space.

Figures 21A, 21B, 21C, 21D, 21E:
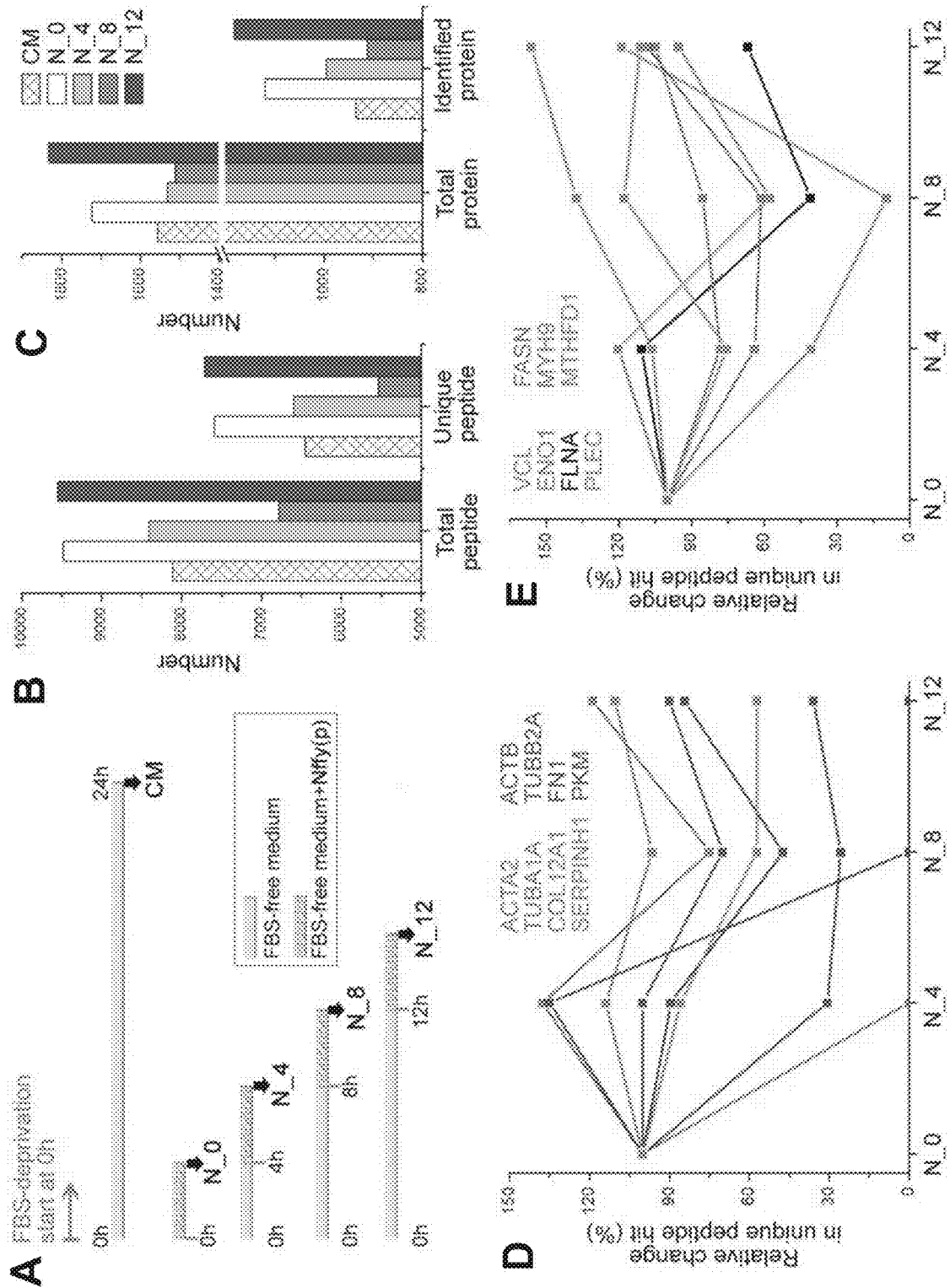
FIGS. 21A-21E show that pericellular nanonets collect transient secretome of cancer cells to build a dynamic profile of the cancer cell secretome.

Tandem protein mass spectrometry ("LC-MS/MS") shows that there are more total peptides and unique peptides (peptide that exists only in one protein in human proteome) in "2 h N" than in "2 h CM" (FIG. 20C). Similar to the trend in peptide coverage, "2 h N" also contains considerably more total proteins and identified proteins (i.e., the protein with 2 or more unique peptides) than does "2 h CM" (FIG. 20D). In fact, the nanonets/hydrogel are able to collect more secretory proteins in 4 hours than CM does in 24 hours (FIG. 21A-B). Thus, the cancer secretome can be effectively sampled using the pericellular nanogel/hydrogel method.

Example 11

Pericellular Nanonets/Hydrogel Reduce Pre-Analytical Variation

Protein mass profiling (i.e., LC-MS/MS) was used to evaluate the pre-analytical variation of the cancer secretome collected using the nanonet/hydrogel method compared to the cancer secretome collected from conditioned media ("CM"). The HeLa cell cancer secretome was collected and evaluated in duplicate following 2 hour incubation using either the nanonets/hydrogel method or CM method. Collected secretomes were evaluated by LC-MS/MS. Proteins identified in each trial were plotted (done by different operators) against the number of unique peptides, i.e., number of unique parent ions, for each protein (Ishihama et al., *Mol. Cell. Proteomics* 4:1265-1272 (2005), which is hereby incorporated by reference in its entirety). According to the number of total peptides and unique peptides observed from proteins of the collected HeLa secretome, the correlation of the proteins collected by nanonets/hydrogel is significantly higher than that of proteins collected by CM (FIGS. 20E-20F). These results confirm that the nanonets/hydrogel method for secretome collection has reduced pre-analytical variation as compared to the CM method.

Figure 26:
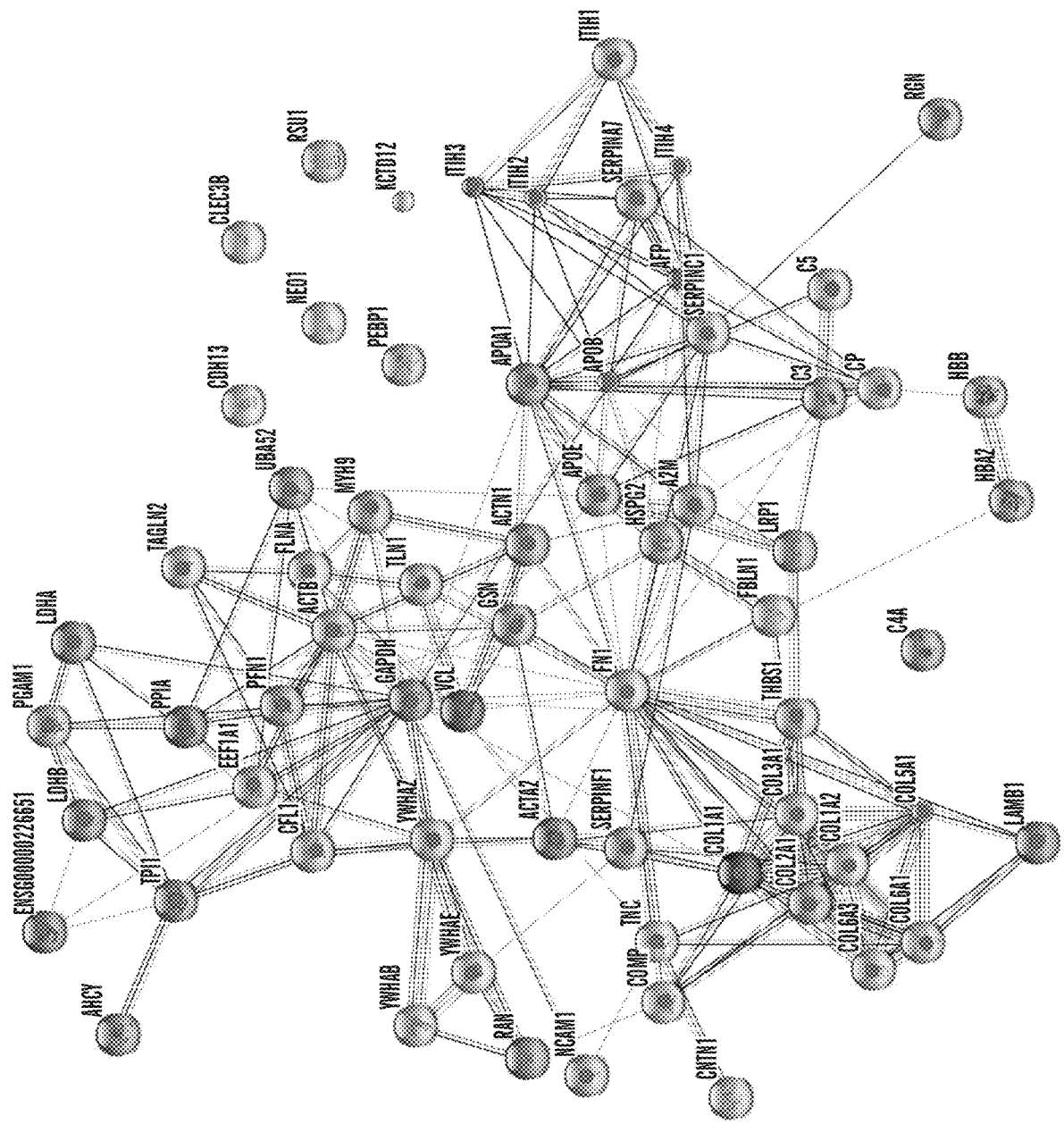
FIG. 26 shows the network of the 67 proteins identified in the two trials of 2 h N and 2 h CM. Actins, serpins, GAPDH, collagens, and their directly interacting proteins are marked by dots.
Figure 27:
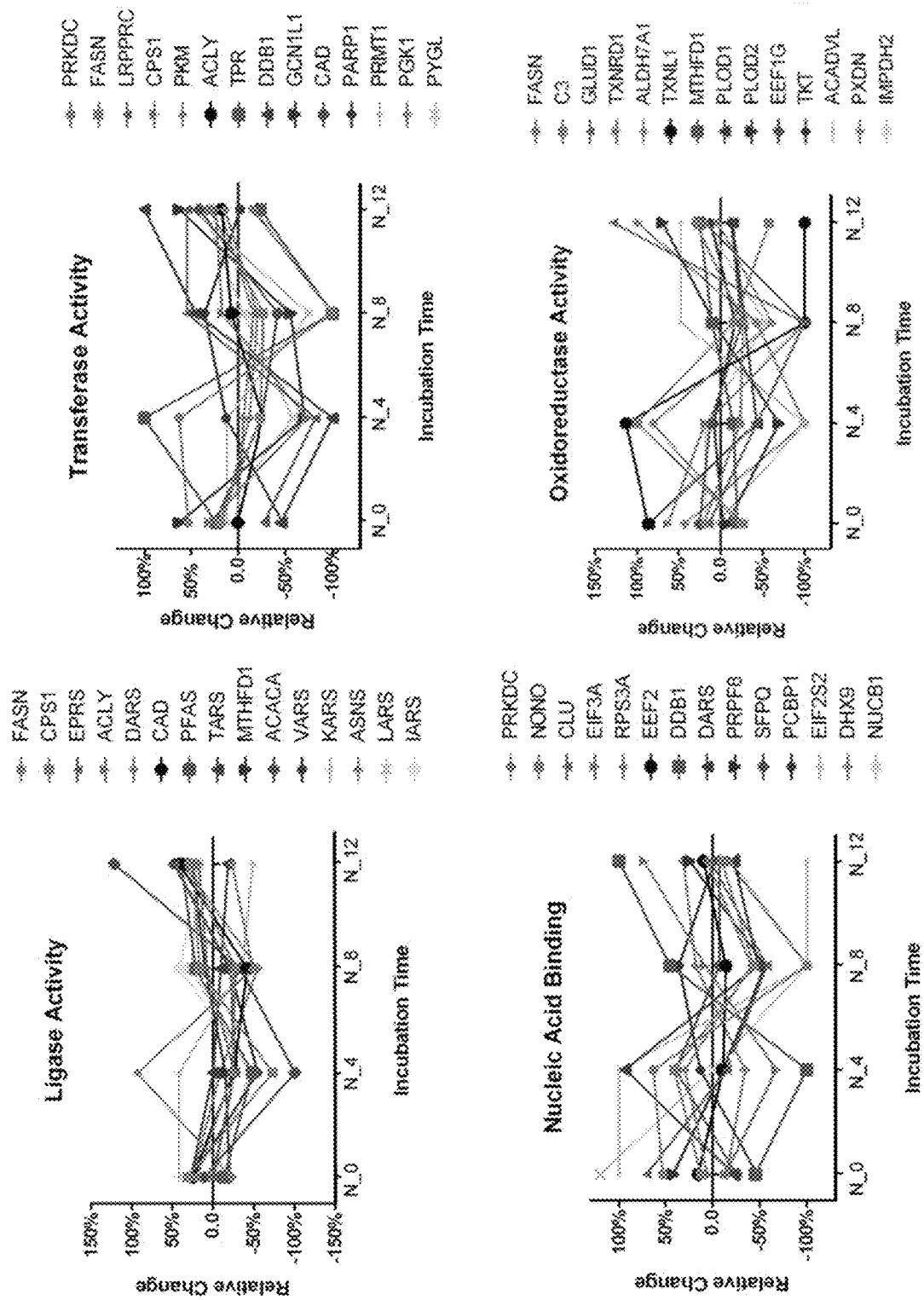
FIG. 27 shows plots which represent the temporal relative change of secretome amount in ligase activity, transferase activity, nucleic activity, and oxidoreductase activity during the FBS-deprivation for different lengths of time (N_0, N_4, N_8 and N_12).
Figure 28:
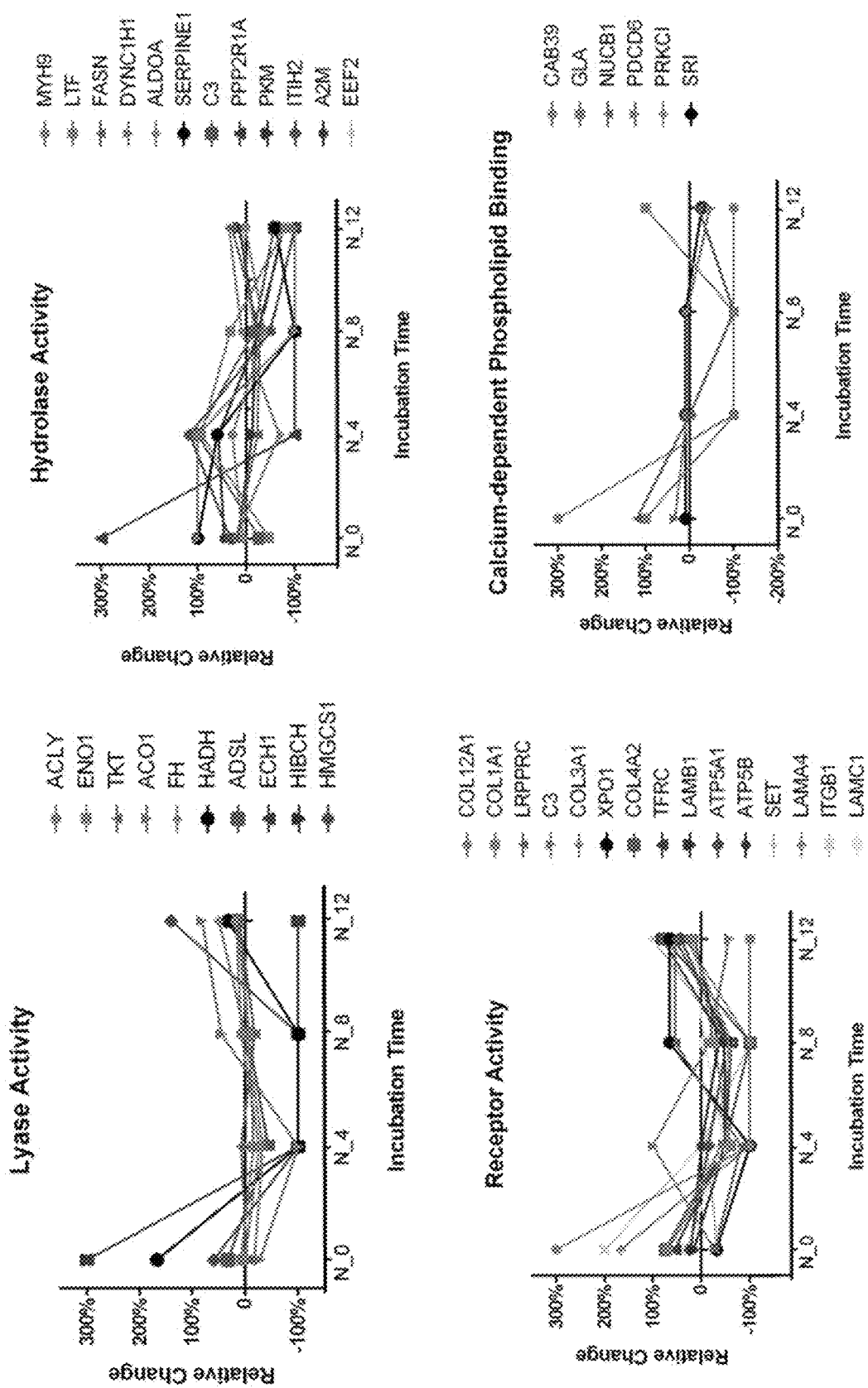
FIG. 28 shows plots which represent the temporal relative change of secretome amount in lyase activity, hydrolase activity, receptor activity and calcium-dependent phospholipid activity during the FBS-deprivation for different lengths of time (N_0, N_4, N_8, and N_12).
Figure 29:
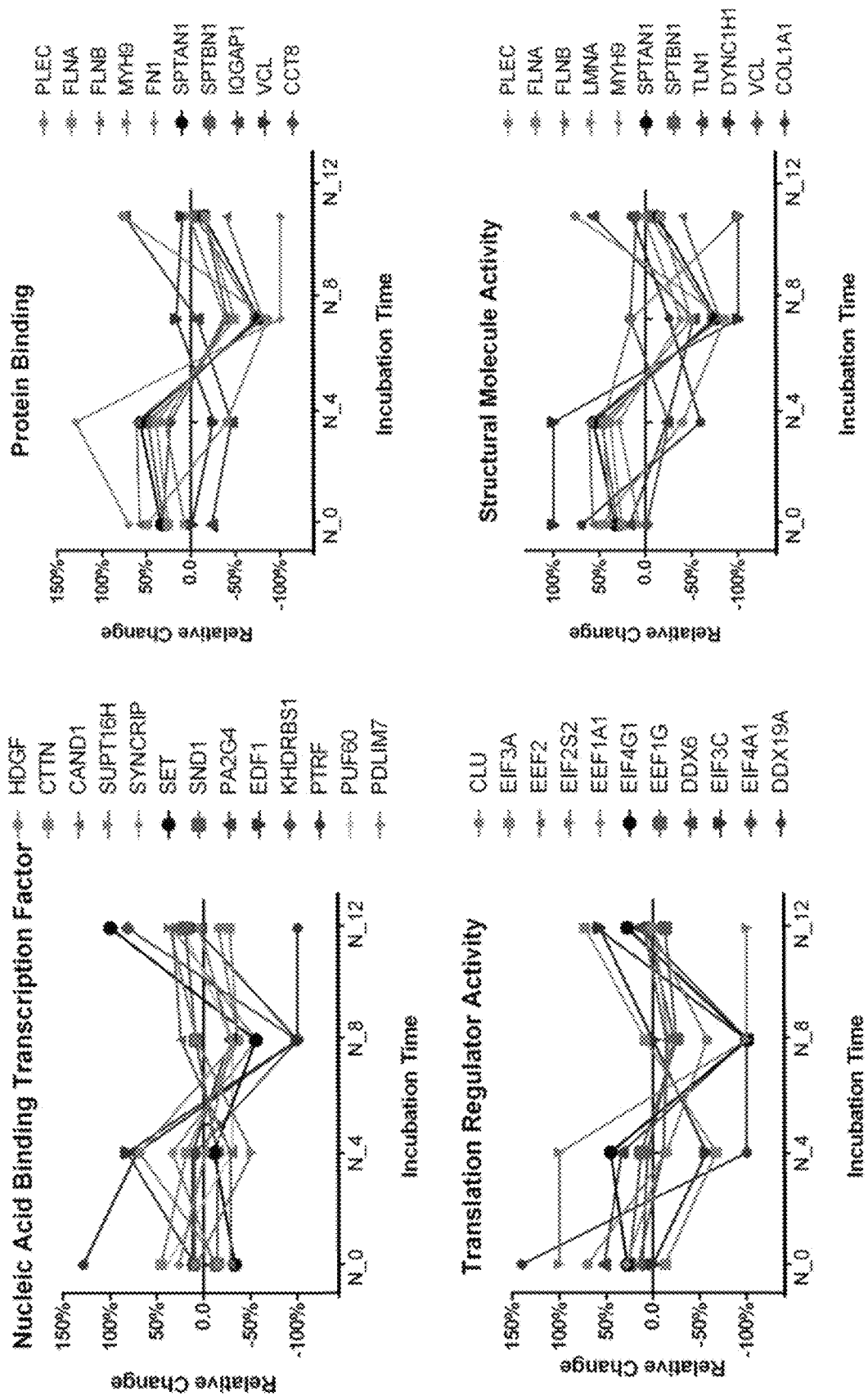
FIG. 29 shows plots which represent the temporal relative change of secretome amount in ligase activity, lyase activity, nucleic acid binding and nucleic acid binding transcription factor during the FBS-deprivation for different lengths of time (N_0, N_4, N_8, and N_12).
Figure 30:
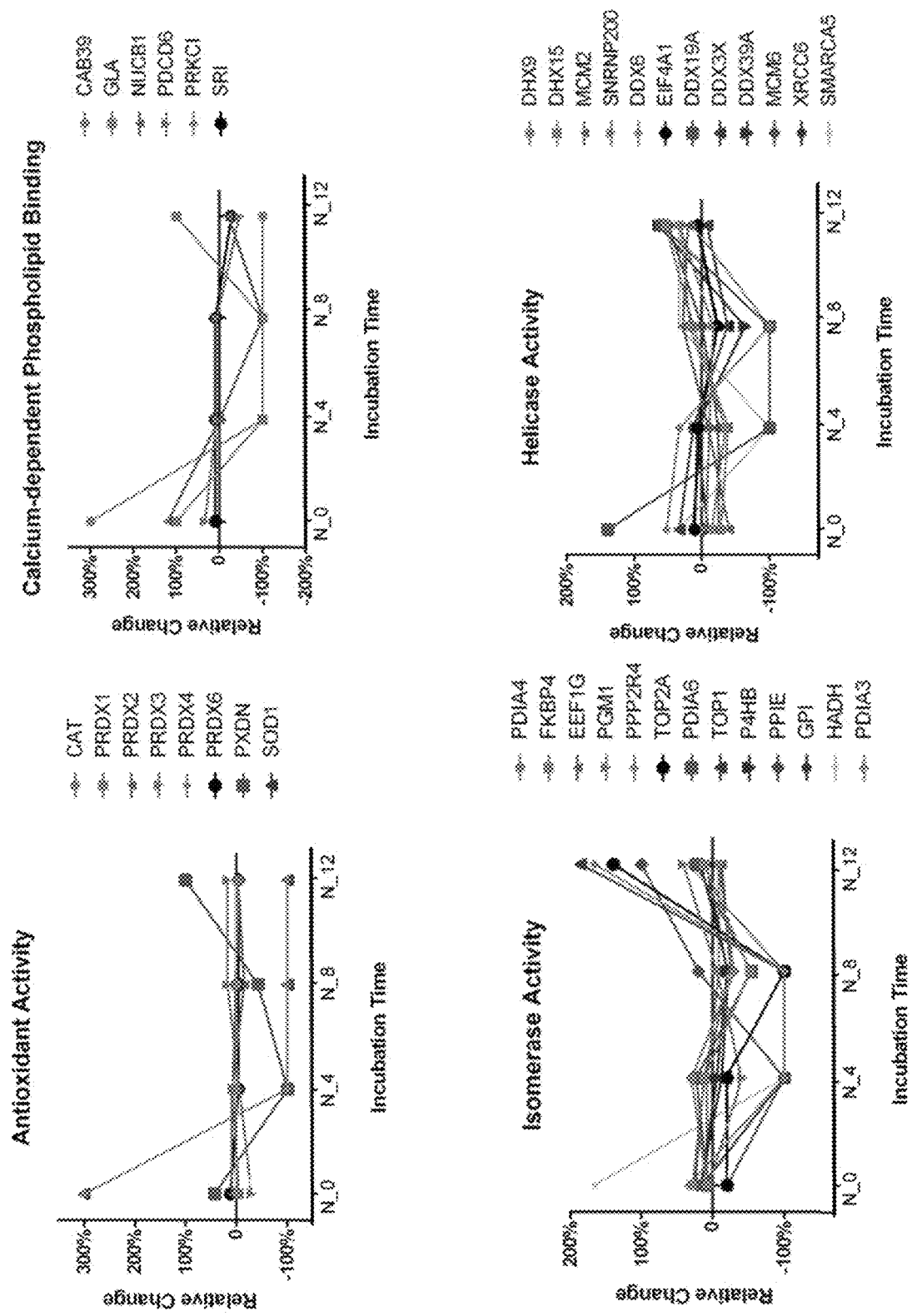
FIG. 30 shows plots which represent the temporal relative change of secretome amount in enzyme regulator activity, hydrolase binding, isomerase activity and helicase activity during the FBS-deprivation for different lengths of time (N_0, N_4, N_8, and N_12).
Figure 31:
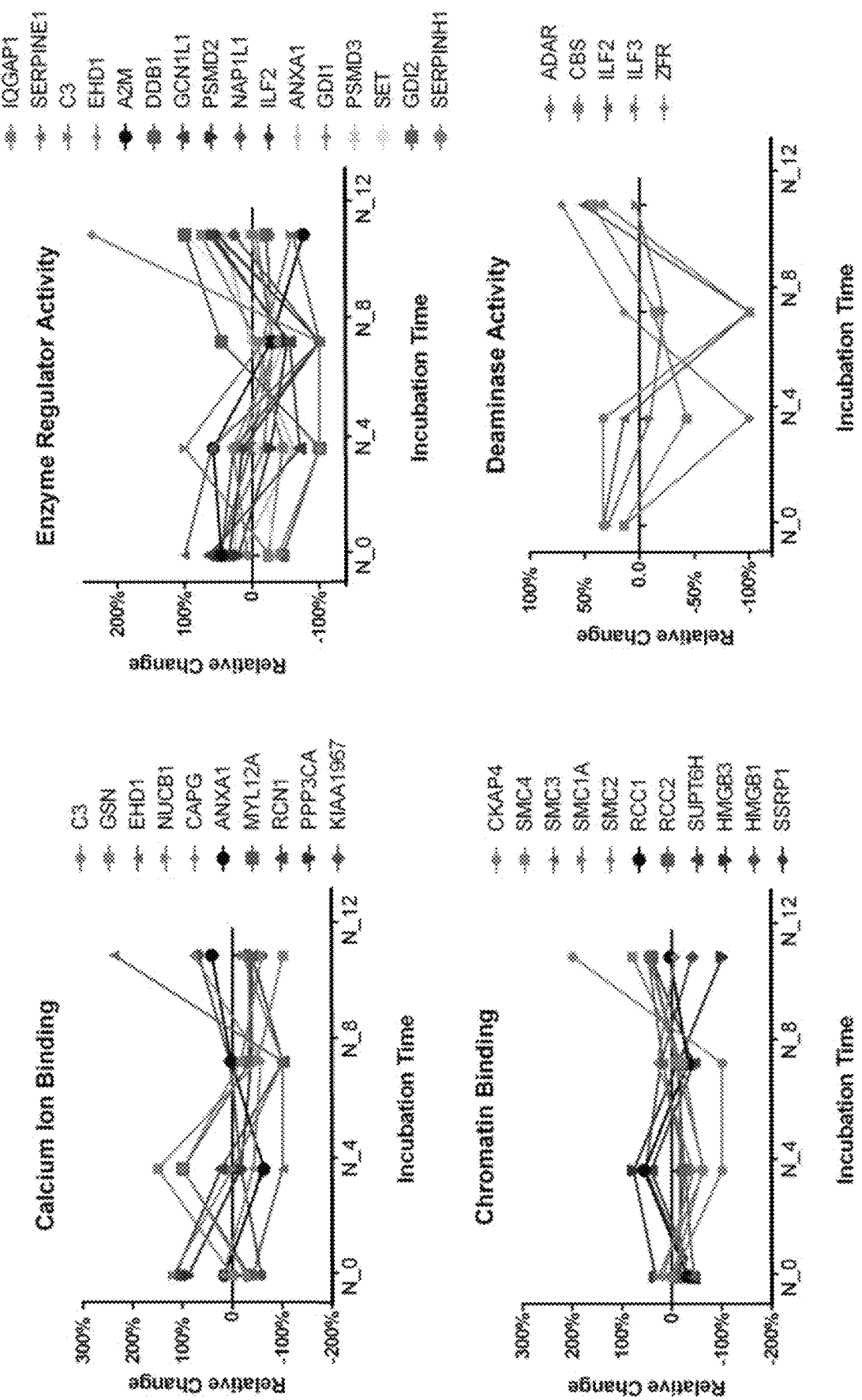
FIG. 31 shows plots which represent the temporal relative change of secretome amount in calcium ion binding, calcium-dependent phospholipid binding, chromatin binding, and deaminase activity during the FBS-deprivation for different lengths of time (N_0, N_4, N_8, and N_12).

Proteins identified in both trials of "2 h N" (122 proteins) were compared with proteins identified in both trials of "2 h CM" (81 proteins) (FIG. 20G). Results show that there are 67 overlapping proteins between "2 h N" and "2 h CM". By exploring the protein-protein interaction network (Snel et al., *Nucleic. Acids. Res.* 28:3442-3444 (2000), which is hereby incorporated by reference in its entirety) of the 67 proteins (FIG. 26), it was found that most of those proteins (50 proteins; 75%) are actins, serpins, collagens, tubulins and their interacting proteins. Despite being of cytosolic origin, actins, tubulins and serpins commonly present in the secretome of human cells, including the secretome of cancer cells (Lin et al., *BBA-Proteins Proteomics* 1834:2360-2371 (2013); Yang et al., *Angew. Chem. Int. Ed.* 46:8216-8219 (2007), each of which is hereby incorporated by reference in its entirety), which agrees with the characteristic of unconventional protein secretion (Yang et al., *Angew. Chem. Int. Ed.* 46:8216-8219 (2007), which is hereby incorporated by reference in its entirety). Besides the overlapping proteins, "2 h N" contains 55 unique proteins, 45 of which are reported to associate with the progression of certain types of cancers. Of the 55 proteins observed only in "2 h N", 50 of them have been observed in the secretome of other cancer cells. However, only 27 of the 55 proteins have been documented in the secretome of HeLa cells (obtained from ultra-filtrated CM of HeLa cells incubated with serum-free medium) (Wu et al., *Mol. Cell. Proteomics* 9:1100-1117 (2010), which is hereby incorporated by reference in its entirety). On the other hand, "2 h CM" has only 14 unique proteins other than the overlapping proteins with "2 h N". These results indicate that "2 h N" is more sensitive in collecting secretory proteins than "2 h CM".

Interestingly, only 34.4% of the 122 identified proteins in "2 h N" are secretory proteins and most of the rest are intracellular proteins, as categorized by UniProt (Magrane & Consortium, "UniProt Knowledgebase: A Hub of Integrated Protein Data," Database-Oxford, (2011)). However, feature-based prediction shows that over 60% of the proteins are classical (by SignalP, Peterson et al., *Nat. Methods* 8:785-786 (2011), which is hereby incorporated by reference in its entirety) or non-classical (by SecretomP, Bendtsen et al., *Protein Eng. Des. Sel.* 17:349-356 (2004), which is hereby incorporated by reference in its entirety) secretory proteins (FIG. 20H). This data is similar to the observation of body fluid of which the secretome contains classical and non-classical secretory proteins, as well as intracellular proteins (Brown et al., *BBA-Proteins Proteomics* 1834:2454-2461 (2013), which is hereby incorporated by reference in its entirety. PANTHER (a web-based classification system) was used to analyze data from protein mass spectrometry of the samples of "2 h N" and "2 h CM". While the percentages of most categories of the identified proteins are quite similar in the samples of "2 h N" and "2 h CM", there are higher percentage of proteins for catalytic, antioxidant, and binding in the secretome collected by the nanonets (FIG. 20I). The above results validate the self-assembly of nanonets as a more accurate and sensitive method for collecting the cancer secretome than CM.

Example 12

Pericellular Nanonets/Hydrogel Register the Temporal Profiles of the Cancer Secretome Because the nanonets/hydrogel collect the cancer cell secretome directly from the pericellular space of cancer cells, this method allows for the detection of high yields of secretory proteins following relatively short incubation times and should allow the detection dynamic changes in the cancer secretome. To test this hypothesis, HeLa cells were incubated in FBS-free medium for defined lengths of time (i.e., 0 hours, 4 hours, 8 hours, or 12 hours) prior to incubation with D-2a for 4 hours (FIG. 21A). During the 4 hour incubation, overexpressed phosphatases on the surface of the HeLa cells convert the hydrogelator precursor D-2a to the hydrogelator D-2b, inducing the formation of pericellular nanonets/hydrogels for secretome collection. Conditioned media ("CM") collected from HeLa cells incubated with FBS-free medium for 24 hours was used as a control for the collection of the HeLa cell secretome (Mbeunkui et al., *J. Proteome Res.* 5:899-906 (2006) which is hereby incorporated by reference in its entirety). Analysis of samples using protein mass spectrometry indicates that the amounts of total peptide and unique peptides collected using the nanonets/hydrogel method are greater than the amounts of total peptide and unique peptides collected by CM (FIG. 21B). The numbers of total and identified proteins of these samples follow the same trend (FIG. 21C). Moreover, the amount of total peptides and unique peptides collected by the nanonets/hydrogels decreases in the time period between 0-8 hours and increases during the time period between 8-12 hours. The amount of total peptides is slightly higher at 12 hours than at 0 hours (FIG. 21B). These results suggest that the protein secretion of HeLa cells is a dynamic process. The decreased protein secretion is consistent with the observed decrease of protein synthesis of cells after short time of FBS-deprivation (Zetterberg et al., *P. Natl. Acad. Sci. USA* 82:5365-5369 (1985), which is hereby incorporated by reference in its entirety). After prolonged FBS-deprivation, the cells starting to synchronize in G0/G1 phase (Walter et al., *J. Cell Biol.* 160:685-697 (2003); Jackman & O'Connor, in *Current Protocols in Cell Biology* (*John* Wiley & Sons, Inc. (2001), each of which is hereby incorporated by reference in its entirety), in other words, the cells begin to enter senescence (Vicencio et al., *Gerontology* 54:92-99 (2008), which is hereby incorporated by reference in its entirety). The change in the condition of the cells likely shifts the behavior of protein secretion by the cells. Although conditioned media provides useful cumulative data of the HeLa cell secretome, it is unable to capture the dynamic changes in the proteins secreted by the cells.

Example 13

Evaluation of the Temporal Profiles of Selected Essential Proteins in the HeLa Cell Secretome Following FBS-Starvation Since the nanonets/hydrogel method allows for the previously unattainable detection of dynamic changes in the cancer cell secretome, the temporal profile of several HeLa cell secreted essential proteins was evaluated. HeLa cells were incubated with FBS-free medium, secretome samples were collected, and hydrogels were analyzed using mass spectrometry. The temporal profile of individual secretory proteins of the HeLa secretome was established by comparing the number of unique peptides detected for each protein (FIGS. 21D-21E). As shown in FIG. 21D, the amounts of alpha-actin 2 ("ACTA2") and beta-actin ("ACTB") change very little over time (from 0-4 h (N_0) to 12-16 h (N_12)). The amount of alpha-tubulin 1A ("TUBA1A") and beta-tubulin 2A ("TUBB2A") also showed only slight variation over time, agreeing with the observation that actins and tubulins have a constant presence in the secretome of mammalian cells (Lin et al., *BBA-Proteins Proteomics* 1834: 2360-2371 (2013); Yang et al., *Angew. Chem. Int. Ed.* 46:8216-8219 (2007), each of which is hereby incorporated by reference in its entirety). On the contrary, the amounts of both collagen alpha-1(XII) ("COL12A1") and fibronectin ("FN1") decreased drastically, that is, the collagen alpha-1 (XII) disappears from N_4 to N_12, and the fibronectin is absent in N_8 and N_12. The amount of two enzymes, serpin H1 ("SERPINH1") and pyruvate kinase ("PKM"), also decreases significantly from N_0 to N_12. These results demonstrate that, to cope with the starvation induced by FBS-deprivation, HeLa cells significantly decrease or reabsorb the extracellular matrix proteins and the secreted enzymes in order to maintain proteostasis (Balch et al., *Science* 319:916-919 (2008), which is hereby incorporated by reference in its entirety).

Several proteins with large numbers of unique peptides were also examined (FIG. 21E). Notably, the amount of plectin ("PLEC") undergoes the biggest change from N_0 to N_12. While the decrease of plectin from N_0 to N_8 likely is to maintain proteostasis, the sudden increase of plectin in N_12 marks the alleviated release of exosome (Shin et al., *P. Natl. Acad. Sci. USA* 110:19414-19419 (2013), which is hereby incorporated by reference in its entirety), agreeing with the behavior of the starving cancer cells that attempt to manipulate tumor microenvironment (i.e., stimulate stromal and endothelial cells) for aiding their progression (Kahlert et al., *J. Mol. Med.* 91:431-437 (2013); Bobrie et al., *Cancer. Res.* 72:4920-4930 (2012) each of which is hereby incorporated by reference in its entirety). Another interesting observation is that, while the amounts of all other proteins show a certain degree of decrease in at least one sample of nanonets, the amount of pyruvate kinase ("PKM") gradually increases over time. As pyruvate kinase is the rate-limiting enzyme in glycolysis (Tanaka et al., *J. Biochem.* 62:71-91 (1967); Stetak et al., *Cancer. Res.* 67:1602-1608 (2007), each of which is hereby incorporated by reference in its entirety), the increased level of pyruvate kinase is likely for meeting the need for ATP production by the cells.

Example 14

Figures 22A, 22B, 22C:
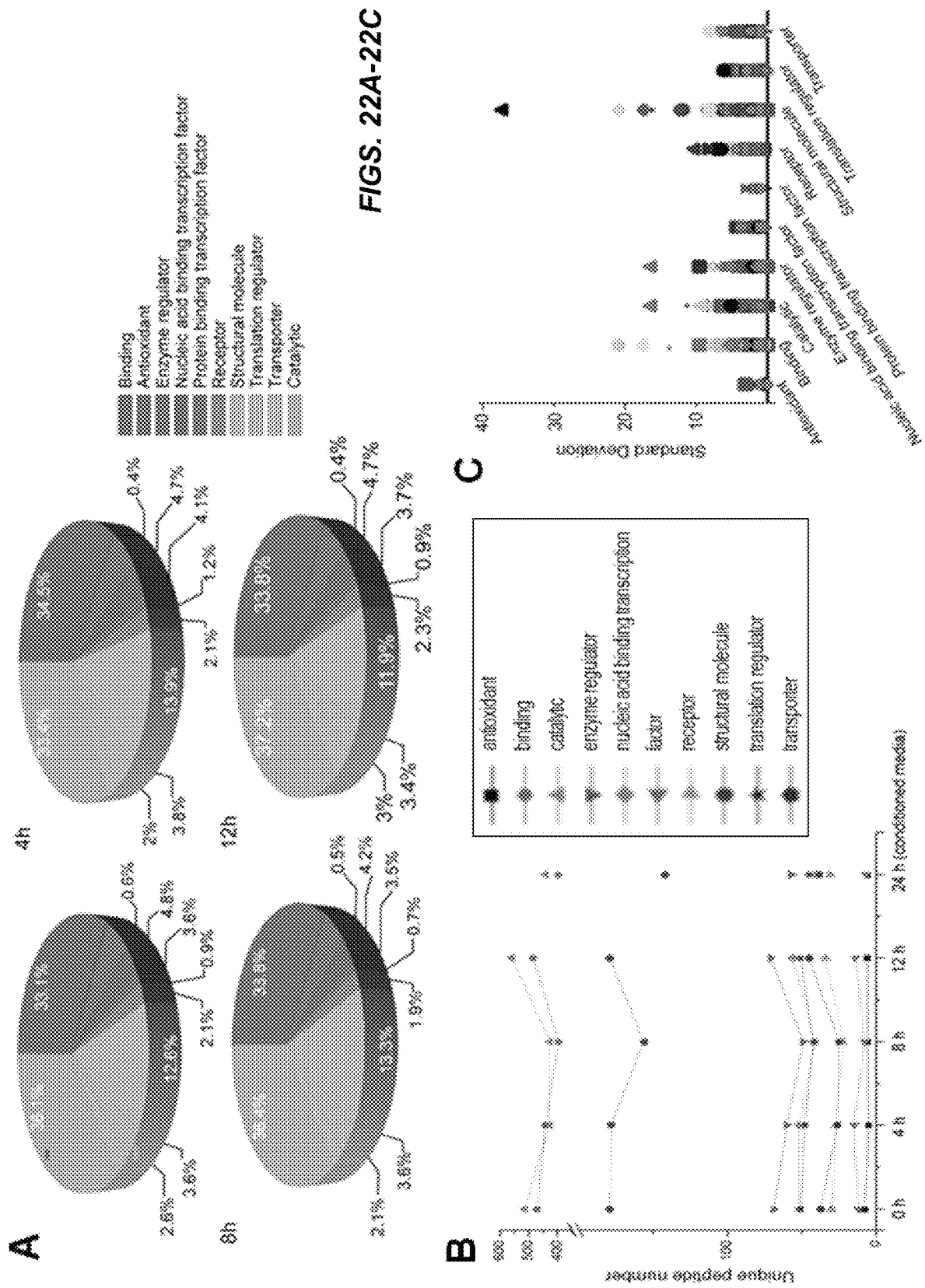
FIGS. 22A-22C show the temporal profile of the categorized cancer cell secretome.

Evaluation of the Temporal Profiles of Categories of Protein in the HeLa Cell Secretome Following FBS-Starvation Although certain individual proteins in the secretome exhibit considerable variation over time, the functional categories of the proteins, as a whole in the secretome, remain rather constant. PANTHER analysis (a web-based classification system) of the data from protein mass spectrometry of the FBS-free samples described above was used to analyze the temporal profiles of categories of protein in the HeLa secretome (FIG. 22A). The percentage of each category of identified protein remained comparable to the results obtained from conditioned media. Eight often categories of the secretome proteins evaluated show the same trend for the amounts of proteins, decreasing followed by increasing over time (FIG. 22B). The fluctuations in the amount of antioxidant and protein binding transcription factors detected shows the different responses to the deprivation of nutrients (i.e., FBS free medium), which is the slight increase in short term (N_4) for antioxidant, and midterm (N_8) increase in protein binding transcription factors. However, both these categories of proteins share the comparatively low baseline levels of protein amount. Thus, the large variation of individual proteins may be compensated for and the general trend reacting to FBS-deprivation still stands constant. The percentage of each category of protein following 24 hour incubation in conditioned media was included as a reference. In general, the amount of protein with conditioned media stays close to the average amount of secretome during temporal change (from N_0 to N_12). This result implies that the overall cellular activities likely remain balanced during the deprivation of FBS. In addition, these results also indicate that 4 hours of incubation with the nanonets leads to minimal perturbation of the secretome.

To understand the temporal change of the secretome in a more precise manner, the relative protein amounts (FIGS. 27-31) and standard deviation values in each category of protein were also calculated. As shown in FIG. 22C, the distribution of the standard deviation of temporal change is different for each protein category. For example, while the secreted proteins in the category of structural molecule activity and binding have standard deviation values larger than 20, the secreted proteins in the category of antioxidant and protein binding transcription factor activity has a standard deviation value lower than 5. This distinct distribution plot indicates that the extent of the responses to FBS-deprivation varies in each category of secretory proteins.

Figure 23:
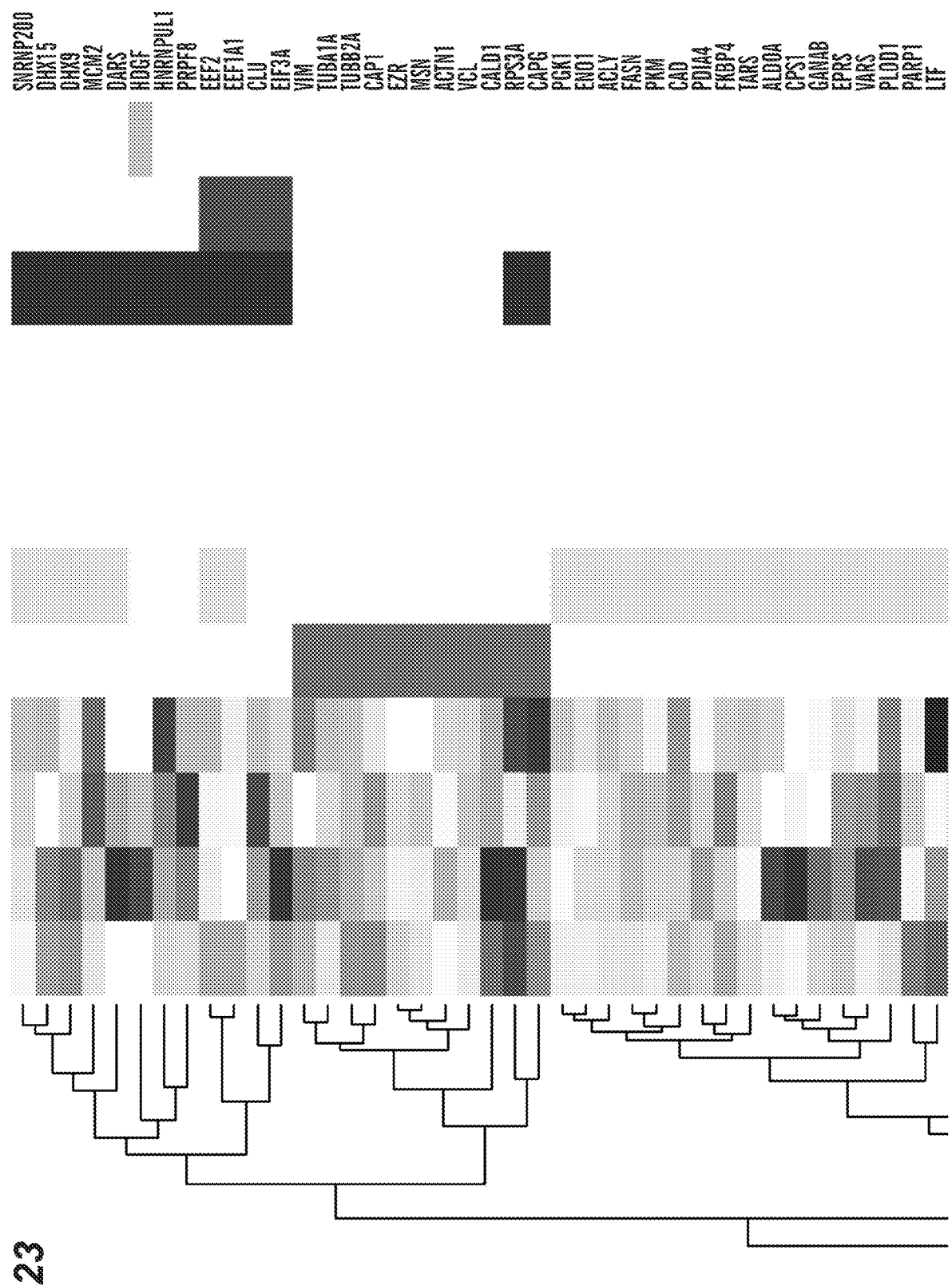
FIG. 23 is a heat map showing the temporal relative change and the functional category of each protein based on GO database annotation for 69 proteins selected by sorting standard deviation from largest to smallest. In the color version of this figure, negative values are indicated by increasing intensity of the color black (−1), neutral is white, and positive values are indicated by the shift from red (+1) to purple (+2) to blue (+3, +4).
Figure 23:
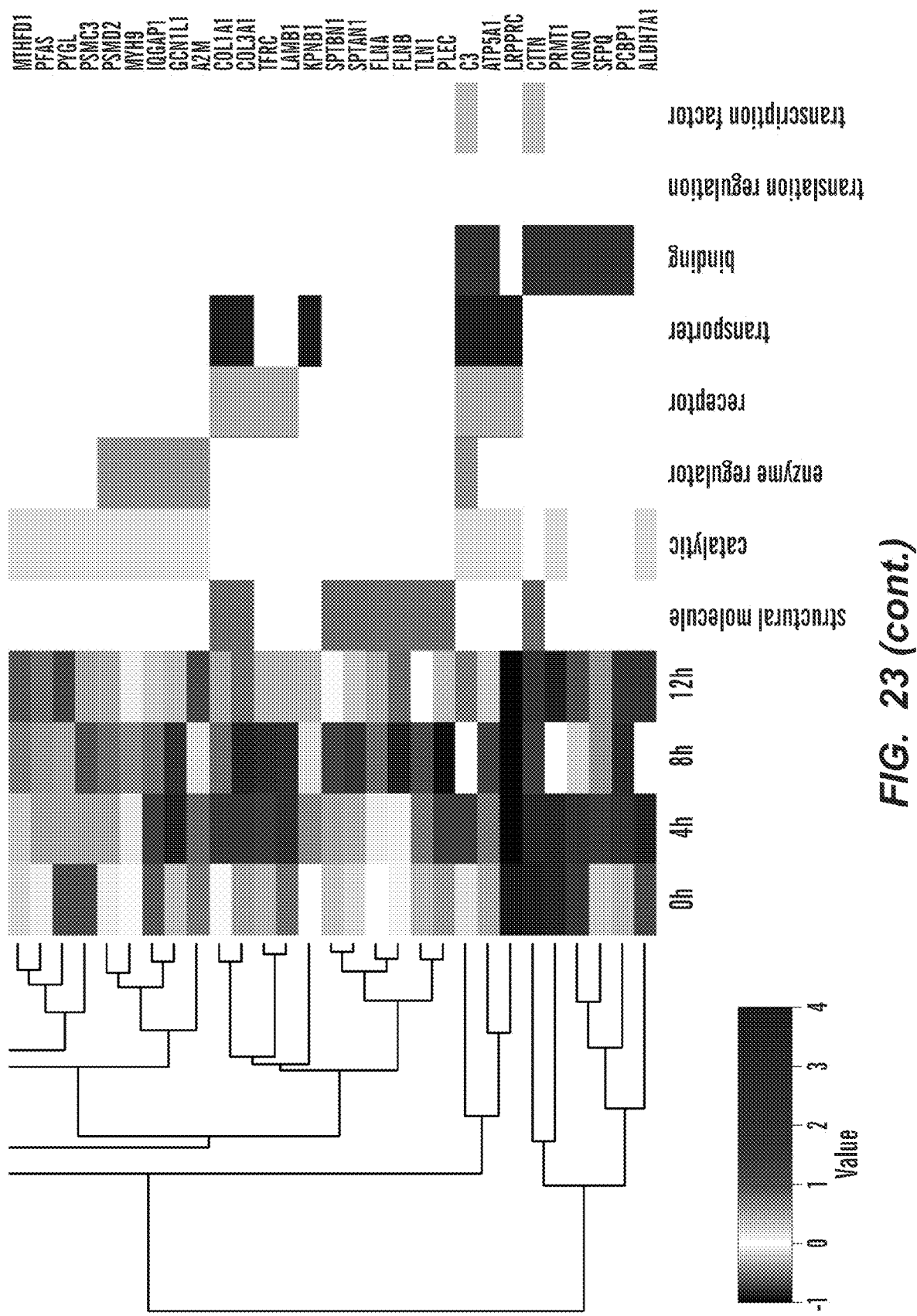

The relative change in protein amount, on the other hand, shows the unbiased changing secretome profile. The definite difference between each time point was divided by the results of the control group (24 hour incubation in FBS-free medium) for each data point in the experimental time period to calculate the relative change ("RC value"). In particular, the relative change (RC value) of each secretome is calculated using the following formula: RC value=unique peptide number of each time point/unique peptide number of control −1. Comparison of temporal change patterns based on the RC values of selected 69 proteins of significant changing profiles is illustrated in FIG. 23. Since certain proteins may belong to more than one category, the functional category of each protein is included in the heat map. The overall range of RC values (from −86% to 100%) reflects the general trend of stable protein secretion of cancer cells during the stimulus of FBS-deprivation. Several proteins exhibit a rather large RC value (PCBP1, ALDH7A1, PRMT1, CALD1, etc.), likely due to a small number of detected unique peptides in the control. This result further indicates that the use of nanonets is a more powerful method than culture medium for collecting the cancer cell secretome.

From 0 to 4 hours, 42 out of 69 proteins (shown in color red to blue) exhibit positive RC values (FIG. 23), indicating an increase in the amounts of the proteins in response to a lack of nutrients. After another 4 hours, the general pattern is a decrease in secretion, as evidenced by the observation that 38 of the 69 proteins have negative RC values (shown in color grey to black). The 8-12 hour and 12-16 hour groups also show a similar decreasing trend since the amount of secretion exhibits negative RC values for 46 and 39 proteins in the groups of 8-12 hours and 12-16 hours, respectively.

A categorized analysis (FIG. 23) of the cancer secretome reveals that most of the proteins within the same functional category rarely share a common trend of temporal profiles of secretion upon stimulation. However, for the proteins that perform more than a single function (i.e., belong to different functional categories), their temporal profiles usually exhibit similar trends over the entire time. For example, proteins grouped into functional categories of both binding and catalytic activity, such as MCM2, DHX9, DHX15, SNRNP200, all show a decrease for the first 4 hours, and an increase for the rest of time in response to FBS-deprivation, but the rest of proteins in only one of these two categories (either binding or catalytic category) hardly show common features. This character apparently is unique for "multifunctional" proteins. In particular, GCN1L1, PSMD2, and IQGAP1, which belong to both catalytic and enzymatic activities, exhibit the same amount of secretion increase for 4 hours at the beginning, but show decrease afterward. This phenomenon was unknown previously, and it certainly warrants further studies.

Example 15

Figures 24A, 24B:
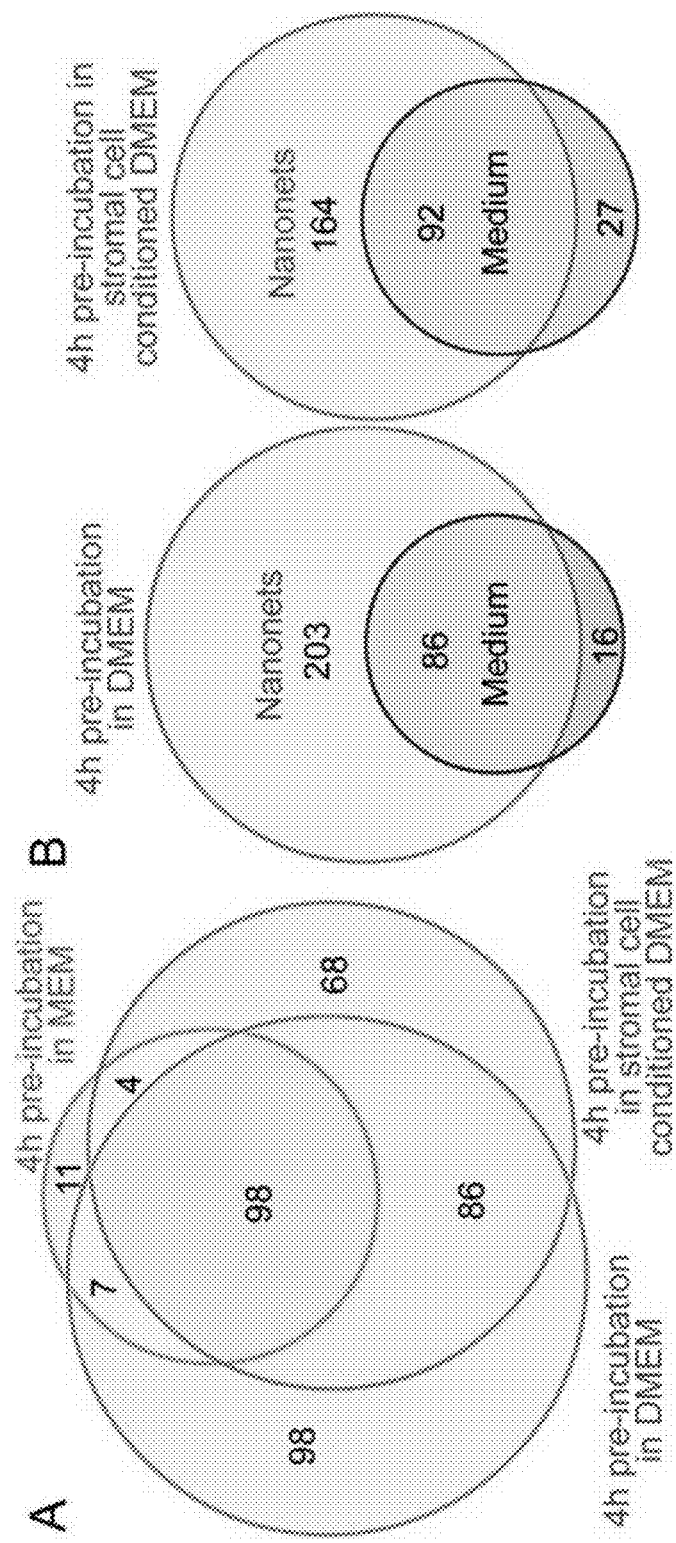
FIGS. 24A-24C shows that nanonets collect different secretory proteins from HeLa cells pretreated by different culture media.

Nanonets Reveal the Response of the Cancer Secretome to Signals from Stromal Cells To demonstrate that the nanonets also are able to register changes in the cancer secretome triggered by other types of stimulation, HeLa cells were pre-treated under different culture media conditions for 4 hours prior to collection of the secretome. FIG. 24A shows the comparison of proteins in the secretome collected from pericellular nanonets from HeLa cells pre-incubated with DMEM for 4 hours, HeLa cells pre-incubated with stromal cell (HS-5) conditioned DMEM for 4 hours, and HeLa cells incubated with complete MEM (control). The results indicate that substantially more protein is collected from pre-treated HeLa cells than from HeLa cells evaluated in the absence of pretreatment (FIG. 24A).

Figure 24C:
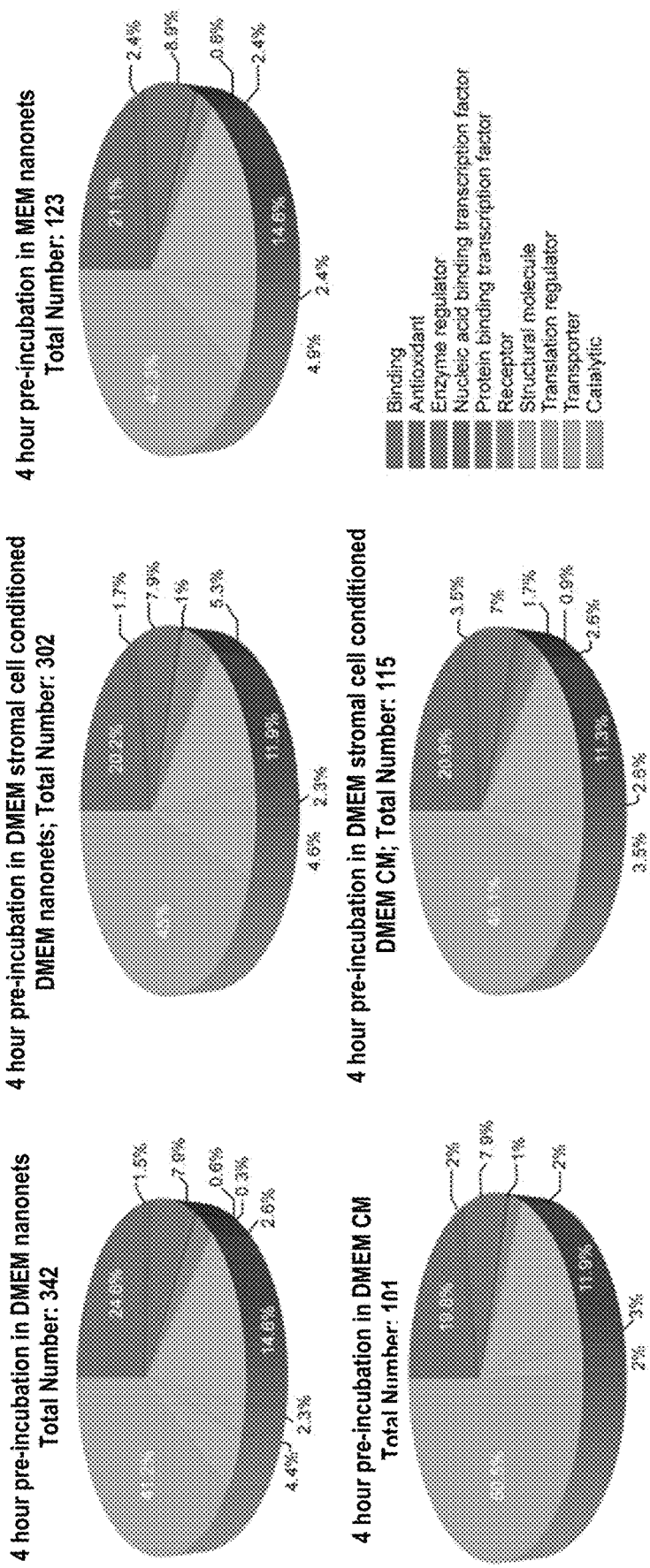

Protein profiling studies demonstrate that the secretory protein profile observed from cells pre-incubated with stromal-cell conditioned medium differs considerably from the profile observed from cells pre-incubated with unconditioned medium (i.e., DMEM) (FIGS. 24B-24C). Of the 289 proteins identified in the nanonets of cells preincubated with unconditioned DMEM, 184 overlap with the 256 proteins identified from the nanonets of cells preincubated with stromal cell conditioned medium (FIG. 24A). These results suggest that the HeLa cells secrete different proteins in response to different stimuli.

Some proteins identified in high abundance for both experimental conditions (cell pretreated with either unconditioned or conditioned medium) showed similar unique and total peptide numbers. For example, ENO1 and PKM show the largest unique and total peptide hits in both secretome profiles, which are 29/93 and 22/57 in untreated DMEM, 29/89 and 25/53 in HS-5 stromal cells conditioned DMEM. This similarity also applies to other proteins with significantly large unique and total peptide hits, such as ACTA2, ACTN4, GAPDA, HSPA5, HSPA8, TUBA1A and TUBB2A.

The change in media conditions also induces approximately double or half of the secretion of some proteins. For example, proteins CPS1, VCL and ATIC have twice the amount of unique and total peptide hits with the unconditioned DMEM comparing to that with HS-5 conditioned media. Proteins A2M, AHCY, and EEF1A1 behave in an opposite way and have about half amount of unique and total peptide hits with the unconditioned DMEM comparing to that with HS-5 conditioned media. Just like the previous demonstration of a more complete secretome profile captured by pericellular nanonets than CM (FIG. 21B), in the experiment of changing stimuli, the pericellular nanonets obtained with a short time span of 4 hours also clearly collect more secretory proteins than CM do over 24 hours of incubation after the pre-treatments. That the CM gathers fewer proteins than pericellular nanonets indicates that the increase of protein secretion after the stimulation is a rather transient process, agreeing with the dynamics of cancer cells.

Figure 25:
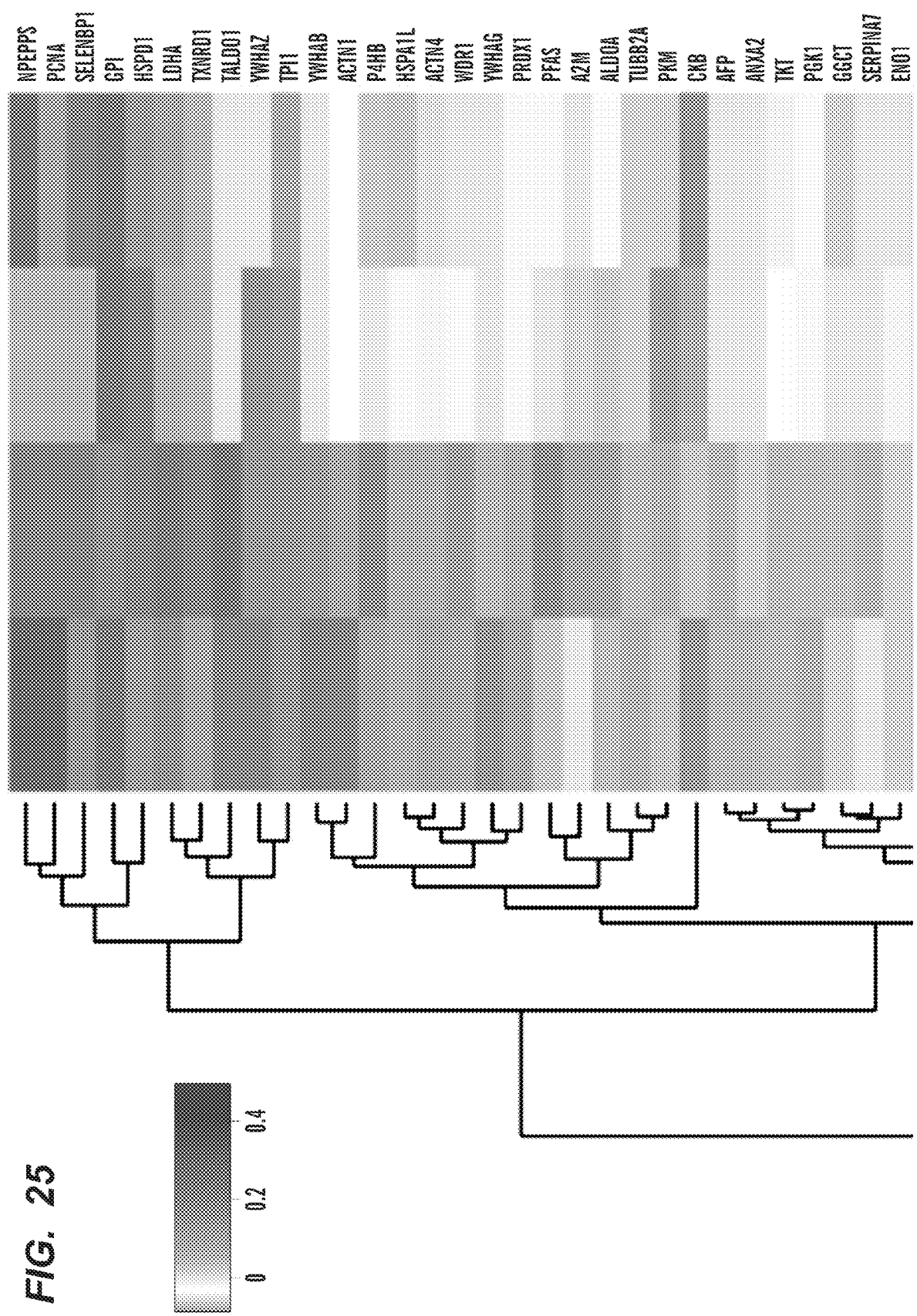
FIG. 25 is a heat map showing the relative change of 54 proteins selected by sorting standard deviation from largest to smallest. In the color version of this figure, an increase in the relative change value ("RC") is indicated by the increasing intensity of red color and a decrease in the RC value is indicated by the increasing intensity of blue color. A white spot on the heat map indicates a neutral response.
Figure 25:
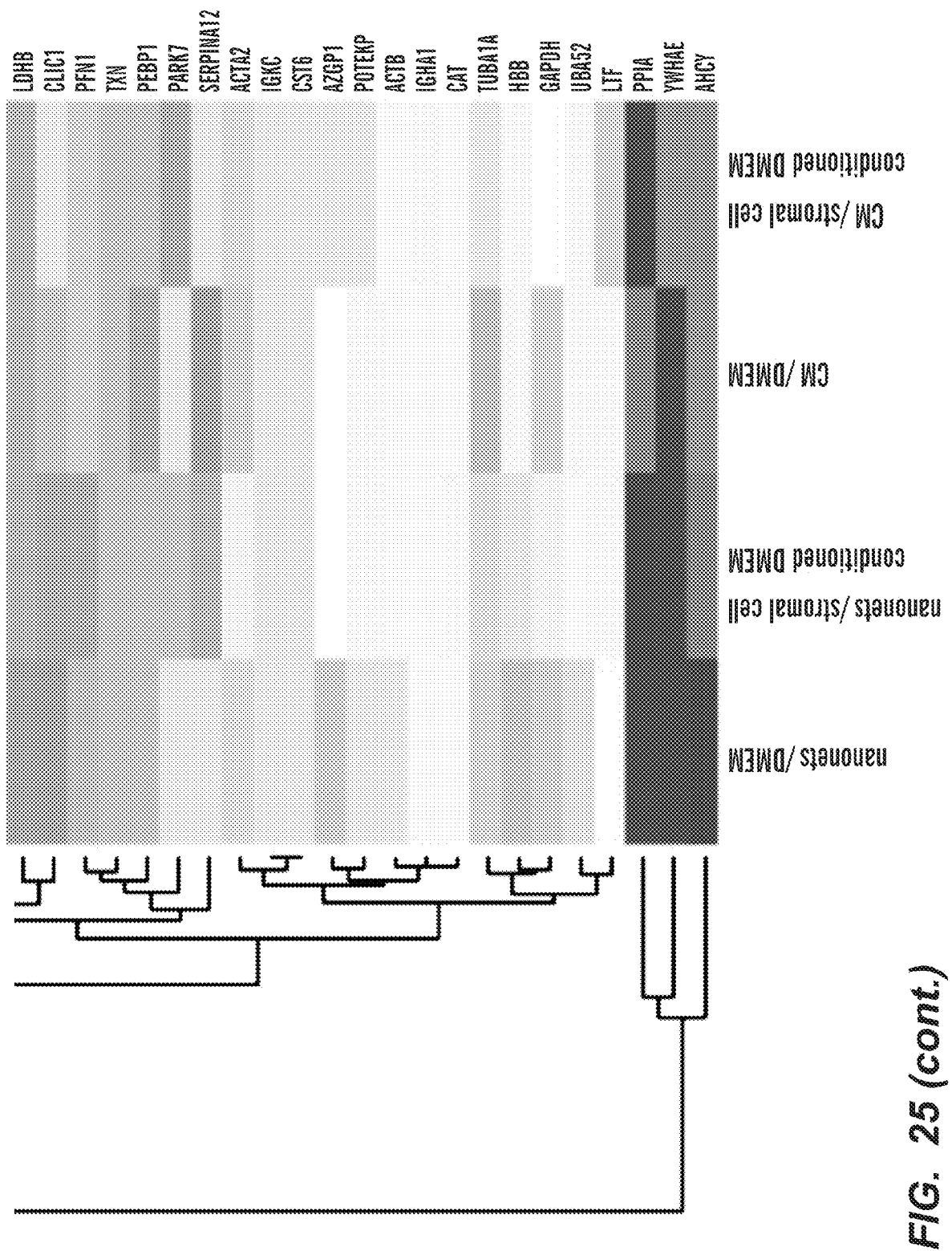

The differences between the secretome collected for each experimental (preincubation with unconditioned or stromal cell-conditioned DMEM) and control condition (preincubation with MEM) is illustrated in the heat map of FIG. 25. For the control condition, the switch of media from MEM to DMEM results in increased secretion of secretory proteins (the relative change ("RC") value, which indicates either an increase or decrease in the total amount of unique peptide hits for each indicated protein in an experimental group compared to the control group, is represented by the intensities in FIG. 25). As expected, nearly all the negative RC values are from the secretome results of CM collection, which also validates the previous observation that higher yield of secretome is obtained in the nanonets than in CM. This increase in protein secretion is consistent when the extent of relative change is less than 50% and most of them show less than 20% increase. This small range of RC indicates that the additional amino acids and vitamins from DMEM (compared to MEM) only induces a limited change to the secretion of the HeLa cells.

The first two columns of FIG. 25 document and compare the secretomes captured from nanonets following HeLa cell pre-incubation with either unconditioned medium (i.e., unconditioned DMEM) or stromal cell conditioned medium (i.e., stromal cell (HS5) conditioned DMEM). HS5-conditioned media is known to promote differentiation (Iwata et al., *Stem Cells and Development* 23:729-740 (2014), which is hereby incorporated by reference in its entirety) of monocytes to dendritic cells and may provide additional cytokines and interleukins (Roecklein et al., *Blood* 85:997-1005 (1995), which is hereby incorporated by reference in its entirety) that help cell growth. Notably, some proteins show relatively different profiles. For instance, the amount of CKB (a cytoplasmic enzyme involved in energy homeostasis, Lei et al., *PloS one* 9:e107746 (2014), which is hereby incorporated by reference in its entirety) is lower in HS-5-conditioned media (unique peptide hits=5) than unconditioned DMEM (unique peptide hits=7)(FIG. 25). This difference, however, unlikely reflects the difference in cell response because the sum of the unique peptide hits of CKB from nanonets and CM indicates that the total amount of peptide hits stay almost the same (12 in HS-5-conditioned media and 11 in untreated DMEM). Thus, in the conditioned media, CKB tends to accumulate more in CM than in nanonets, suggesting that the secretion of CKB may be stable upon the switch of the media, but abundance of CKB in CM is greater than that in nanonets with HS-5-conditioned media.

These results not only reveal that HeLa cells regulate the secretome to cope with the change of environment (Richards & Sutherland, *Trends. Biochem. Sci.* 22:432-436 (1997), which is hereby incorporated by reference in its entirety), but also indicate that the use of pericellular nanonets ultimately leads to an effective method to document the transient changes and the dynamics of cancer secretome in tumor microenvironment (Lu et al., *J. Cell Biol.* 196:395-406 (2012), which is hereby incorporated by reference in its entirety) and identify proteins that may be abnormally secreted, shed, or overexpressed upon stimulation.

Discussion of Examples 8-15

The results described herein demonstrate that the integration of the biochemical catalysis (i.e., enzymatic dephosphorylation) of cancer cells with the collection process enables the rapid, direct and comprehensive collection of cancer secretome from pericellular space. The higher yield of proteins collected by the nanonets (in most cases); the observation of autocrine AFP—a potential cancer biomarker (Esteban et al., *Int. J. Cancer* 49:425-430 (1991); Wang et al., *Life Sci.* 64:17-23 (1998), each of which is hereby incorporated by reference in its entirety) that has not been documented in HeLa secretome (Wu et al., *Mol. Cell. Proteomics* 9:1100-1117 (2010), which is hereby incorporated by reference in its entirety) in a relatively short period of time (4 hours); and the observation of the exosomal protein, plectin, together demonstrate the high sensitivity of using nanonets for profiling secretory proteins. Yet, exception in respect of higher abundance of protein in nanonets exists, such as protein mass spectrometry identified a little less secretory proteins from the nanonets (1,120 identified protein in N_0) than from ultrafiltration concentrated CM (1,223 identified protein) (Wu et al., *Mol. Cell. Proteomics* 9:1100-1117 (2010), which is hereby incorporated by reference in its entirety), with both the nanonets and the CM obtained from the HeLa cells in FBS-free medium. Despite this different result in FBS-free medium, it is still an effective method for collecting the cancer secretome. Moreover, the collection procedure using nanonets is simple and eliminates the need for additional purification or concentration steps. The collection procedure of nanonets, which significantly reduces pre-analytical variation between trials and improves sensitivity, indicates that it is not only suitable to combine pericellular nanonets with other proteomic techniques, such as SILAC (Polacek et al., *J. Orthop. Res.* 28:1040-1049 (2010), which is hereby incorporated by reference in its entirety), for accurate and comprehensive mapping of cancer secretome, but also may evolve into a low-cost diagnostic method for developing regions (Martinez et al., *Anal. Chem.* 82:3-10 (2010), which is hereby incorporated by reference in its entirety). The short time of incubation also enables the nanonets to capture changes in the cancer secretome in response to stimulation, which may reveal new insights on cancer drug resistance. The examination of the dynamics of cancer secretome using pericellular nanonet, undoubtedly, will generate important information for understanding the complex roles of secretome in the progression of cancer, and might provide the venue for the discovery of cancer biomarkers. Moreover, the spatiotemporal control on the formation of the nanonets ultimately may lead to the single cell analysis (Jeffries et al., *Nano. Lett.* 7:415-420 (2007); Whitaker et al., *J. Biol. Chem.* 286:21623-21632 (2011), each of which is hereby incorporated by reference in its entirety) of secretome in tumor microenvironment.

Example 16

Figures 17A, 17B, 17C:
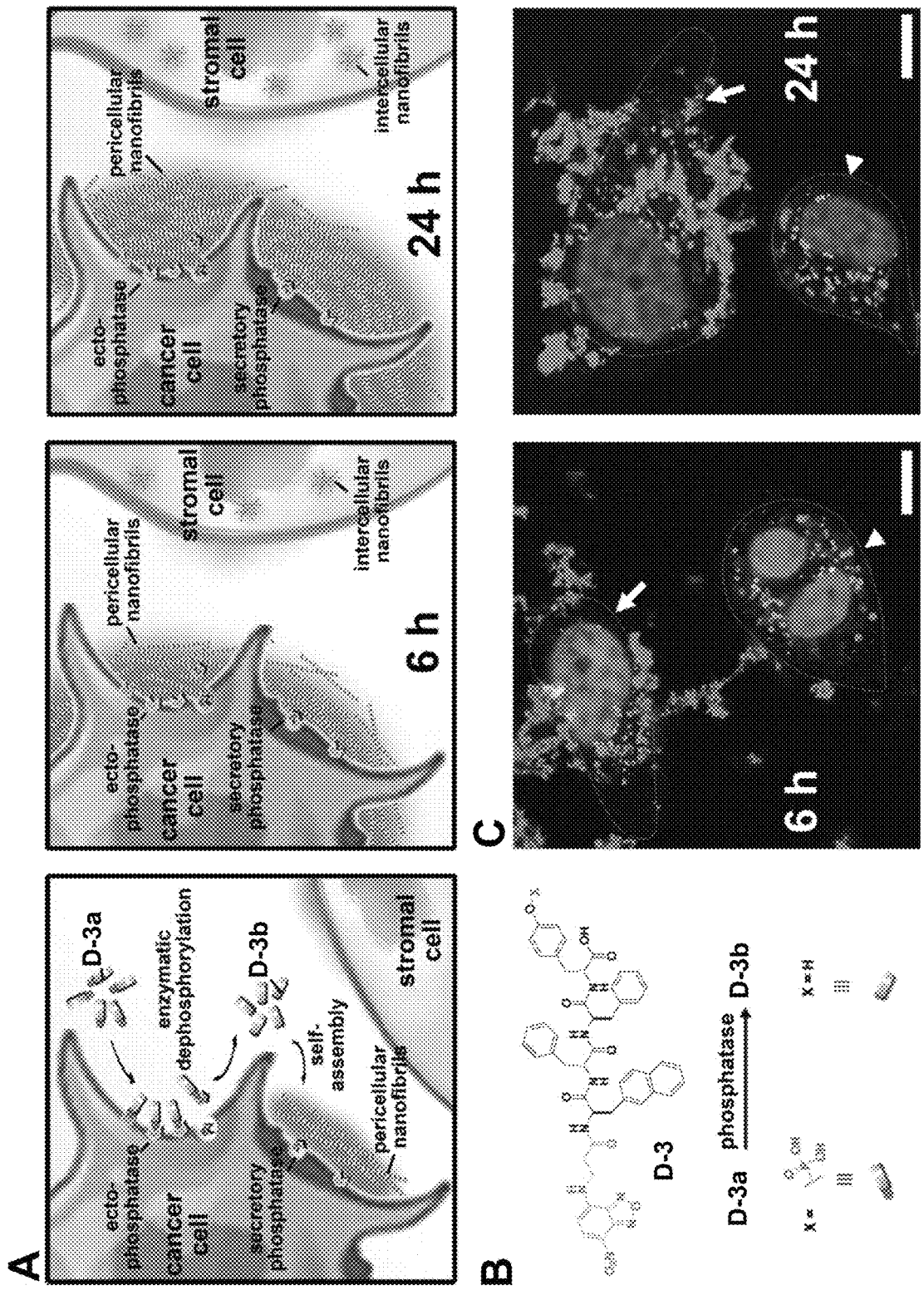
FIGS. 17A-C illustrates that phosphatases catalyze self-assembly to form fluorescent nanofibrils with high spatiotemporal resolution.

Design and Synthesis of the Hydrogelator Precursor D-3a and the Hydrogelator D-3b As demonstrated in Example 1-6, applicants unexpectedly observed the alkaline-phosphatase catalyzed selective formation of D-peptide nanofibrils in the pericellular space surrounding cancer cells (see FIG. 17A). Benefiting from the low affinity to endogenous proteins and proteolytic stability of D-peptides, the unusual spatiotemporal control exhibited by this enzyme-catalyzed self-assembly process (Yang et al., *Acc. Chem. Res.* 41:315-326 (2008), which is hereby incorporated by reference in its entirety) led to the development of a novel precursor hydrogelator molecule, D-3a (FIG. 17B). The precursor hydrogelator D-3a (FIG. 17B) includes a fluorophore (4-nitro-2,1,3-benzoxadiazole ("NBD")) and a tetrapeptide containing (D-3-(2-naphthyl)alanine, two D-phenylalanine, and tyrosine phosphate, or NBD-D-Nal-D-Phe-D-Phe-D-$_p$Tyr. Dephosphorylation of $_p$Tyr by a phosphatase converts the precursor D-3a to the hydrogelator D-3b. Molecule D-3b is more hydrophobic than D-3a and is able to self-assemble to form nanofibrils that result in a hydrogel in physiological conditions (Estroff et al., *Chem Rev* 104:1201-1217 (2004), which is hereby incorporated by reference in its entirety). The NBD motif, which gives an enhanced fluorescent signal in a hydrophobic environment, can indicate nanofibril formation (Gao et al., *Nat. Commun.* 3:1033 (2012), which is hereby incorporated by reference in its entirety). The D-amino acid residues as the peptide backbone ensure the proteolytic stability and reduce endocytosis of D-3a and D-3b. The aromatic groups of the D-Nal and D-Phe provide sufficient hydrophobic interactions to allow the self-assembly of D-3b into nanofibrils. Based on this design, after coupling β-alanine with NBD-Cl to obtain the NBD-NH(CH$_2$)$_2$COOH, D-3a was prepared by solid phase peptide synthesis ("SPPS") (Chan & White, eds., *Fmoc Solid Phase Peptide Synthesis: A Practical Approach* (Oxford Univ Press, 2000), pp. 346, which is hereby incorporated by reference in its entirety). Purification of the crude product by a reverse phase HPLC affords D-3a in 60% yield.

Example 17

Fluorescent Nanonets/Hydrogels Selectively Form on the Surface of Cancer Cells, but not Stromal Cells Co-culture of cancer cell (i.e., HeLa cells) and stromal cells (i.e., HS-5 cells) mimics the tumor microenvironment (Straussman et al., *Nature* 487:500-U118 (2012), which is hereby incorporated by reference in its entirety). Incubation with D-3a results in the selective formation of bright yellow (NBD) fluorescence on the surface of the cancer cells over time (FIG. 17C), indicating that significant ectophosphatase-catalyzed dephosphorylation of D-3a occurs on the surface of HeLa cells. In contrast, only yellow puncta are observed inside the HS-5 stromal cells (FIG. 17C). These results indicate that D-3a is able to detect the global spatiotemporal profiles of phosphatases within and on the surface of cells and that nanonets/hydrogels selectively form on the surface of cancer cells, but not on stromal cells. This approach also offers a method for the visualization of live cells that express ectophosphatases.

Example 18

Figures 18A, 18B, 18C, 18D, 18E, 18F, 18G, 18H:
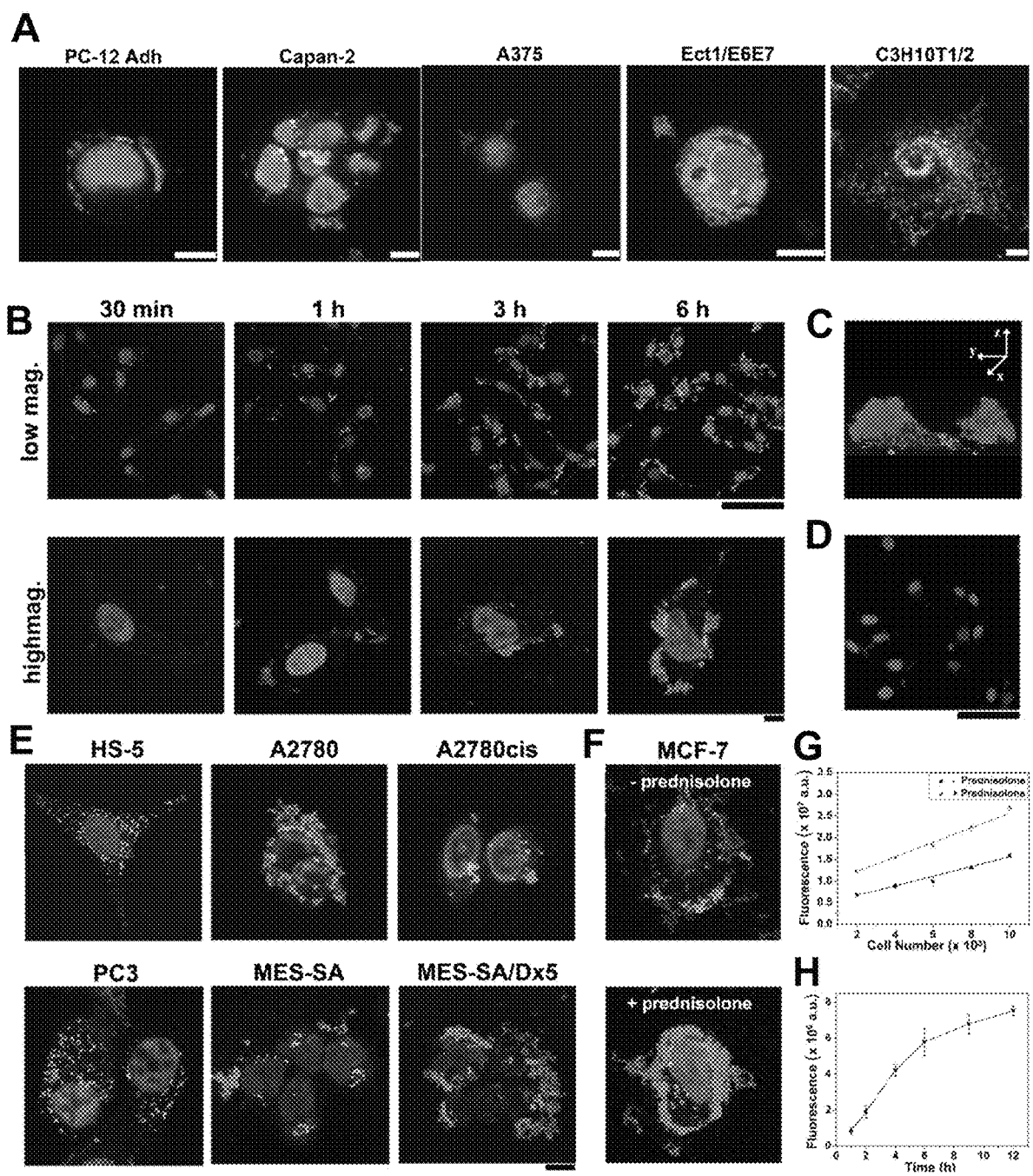
FIGS. 18A-H show imaging and ectophosphatase quantification of live cells incubated with D3-a.

Enzymatic Transformation and Nanofibril Self-Assembly for Spatiotemporal Profiling the Activities of Phosphatases of Live Cells To validate D-3a as an effective agent for the detection of phosphatase activity on a wide variety of cells, the cellular ectophosphatase activity of various cell lines, including PC-12, Capan-2, A375, Ect1/E6E7, and C3H$_{10}$T1/2, was evaluated following 24 hour incubation of cells with 500 μM D-3a (FIG. 18A). In particular, the cell line PC-12 Adh, derived from a pheochromocytoma of the rat adrenal medulla, showed moderate expression of ectophosphatase, with more than 50% of its surface exhibiting NBD fluorescence. In contrast, the cell lines Capan-2 (from human pancreas) and A375 (from human skin) show either weak or no fluorescence, respectively, indicating the presence of low amounts of ectophosphatases on the cell membrane. Ect1/E6E7, an immortalized cervical epithelial cell line, exhibits strong fluorescence in the cytosol, probably resulting from membrane permeability and/or overexpression of phosphatases within cells. The pluripotent murine C3H$_{10}$T1/2 cell line exhibits sporadic fluorescence on cell surface, indicating a fair level of ectophosphatase expression.

To investigate the spatiotemporal resolution of D-3a fluorescence, HeLa cells were incubated with 500 μM D-3a for varying amounts of time (30 minutes, 1 hour, 3 hours, and 6 hours, respectively) and imaged by confocal microscopy (FIG. 18B). Nuclei were stained with Hoechst 33342. FIG. 18B shows that cells exhibit increased cell surface fluorescence with time. HeLa cells incubated for 6 hours with D-3a showed cell surface fluorescence (FIG. 18C). Imaging of HeLa cells incubated with fresh medium for 24 hours following 6 hour incubation with D-3a shows only nuclear dye fluorescence (FIG. 18D). Quantification of ectophosphatase activity on the surface of HeLa cells treated with 500 μM of D-3a is shown in FIGS. 18G-18H as a function of cell number or time, respectively.

This method was also used to image the cancer cell lines A270, A270cis, MES-SA, MES-SA/dx, and PC3 and the stromal cell line HS-5 (FIG. 18E). Ectophosphatase imaging revealed differences between the paired drug sensitive/drug resistant cell lines A270/A270cis and MES-SA/MES-SA/dx (FIG. 18E). Difference in the ectophosphatase activity of the MCF-7 cells incubated in the presence and absence of hormonal stimulus were also observed (FIG. 18F). These results validate D-3a as an effective agent for spatiotemporal imaging of the activities of phosphatases on a wide variety of cells (FIGS. 18A-18H).

Discussion of Examples 16-18

Being controlled by kinase/phosphatase enzyme switch, protein phosphorylation/dephosphorylation is one of the most common mechanisms for modulating the functions of proteins in a wide range of cellular processes (Lodish et al., *Molecular Cell Biology*, W.H. Freeman, ed. 7$^{th}$ (2012), which is hereby incorporated by reference in its entirety). Emerging evidence has revealed that phosphatases play key regulatory roles in many physiological processes, including immune response (Khalil et al., *Science* 336:1178-1181 (2012); Vivier et al., *Science* 306:1517-1519 (2004), each of which is hereby incorporated by reference in its entirety), pathogen virulence (Broberg et al., *Science* 329:1660-1662 (2010), which is hereby incorporated by reference in its entirety), cancer cell proliferation and metastasis (Fishman et al., *Nature* 219:697 et seq. (1968); Pospisil et al., *BMC Bioinformatics* 7:11 (2006); Ruark et al., *Nature* 493:406-U152 (2013); Saha et al., *Science* 294:1343-1346, each of which is hereby incorporated by reference in its entirety), and host and microbe interaction (Bates et al., *Cell Host Microbe* 2:371-382 (2007), which is hereby incorporated by reference in its entirety). Particularly, recent data mining of phosphatases suggests significant overexpression of ALP on the surface of tumor cells (Pospisil et al., *BMC Bioinformatics* 7:11 (2006), which is hereby incorporated by reference in its entirety).

As a type of ectoenzyme, ALP anchors in the membrane, exposing its catalytic domain on the outside surface of the plasma membrane of cells. The evaluation of the activities of ectophosphatases is rather difficult and largely neglected. Because they are membrane proteins, the ectopic expression of green fluorescent protein ("GFP") to ALP can lead to mislocation of ALP (Kweon et al., *Mol. Biol. Cell* 14:1868-1881 (2003), which is hereby incorporated by reference in its entirety) and the routine preparation of cell lysates often misses ALP due to their co-precipitation with membrane components (Claude, *J. Exp. Med.* 84:51-59 (1946), which is hereby incorporated by reference in its entirety) or because ectopic ALP is indistinguishable from secretory alkaline phosphatases ("SEAP") in this context. These results and facts underscore an unmet need to profile the activities of phosphatases for understanding the functions of phosphatases in whole cell or tissue level.

In fact, ectophosphatases (e.g., placental alkaline phosphatases), have been implicated to associate with cancers for over sixty years (Fishman et al., *Nature* 219:697 et seq. (1968); Bernhard et al., *Science* 118:114-115 (1953), each of which is hereby incorporated by reference in its entirety) and have served as tumor markers for certain cancers, e.g., seminoma (Lange et al., *Cancer Res.* 42:3244-3247 (1982), which is hereby incorporated by reference in its entirety). Thus, the activity profiling of ectophosphatases would provide important information for understanding cancer biology. Despite the increasing recognition of the importance of ectoenzymes in cellular activities (Lange et al., *Cancer Res.* 42:3244-3247 (1982); Salmi et al., *Nat Rev Immunol* 5:760-771 (2005); Cosentino-Gomes et al., *J. Bioenerg. Biomembr.* 43:89-92 (2011); Malavasi et al., *Blood* 118:3470-3478 (2011); Vergote et al., *Obstetrics and Gynecology* 69:228-232 (1987), each of which is hereby incorporated by reference in its entirety), there is little development on imaging the activities of ectophosphatases on live cells (Kawaguchi et al., *J. Am. Chem. Soc.* 133:12021-12030 (2011); Jiang et al., *J. Am. Chem. Soc.* 131:1658 et seq. (2009), each of which is hereby incorporated by reference in its entirety).

Several agents for detecting or imaging phosphatases still suffer serious shortcomings. The conventional color assay, p-nitrolpenyl phosphate (PNPP) (Lorenz, *Curr Protoc Immunol.*, Chapter 11, Unit 11.17 (2011), which is hereby incorporated by reference in its entirety), though being able to detect the presence of phosphatases, is unsuitable for live cell imaging due to the lack of spatial resolution and sensitivity. The fluorescent staining agent ELF®97, which bases on restricting bond rotation to generate fluorescent colloids (Larison et al., *J. Histochem. Cytochem.* 43:77-83 (1995), which is hereby incorporated by reference in its entirety), requires cell fixation and the inhibition of ALPP by L-phenylalanine (Fernley and Walker, *Biochem. J.* 116:543 et seq. (1970), which is hereby incorporated by reference in its entirety) during the histological sample preparation (Cox and Singer, *J. Histochem. Cytochem.* 47:1443-1455 (1999), which is hereby incorporated by reference in its entirety). As such, ELF®97 is unsuitable for activity profiling of phosphatases. The recently reported quinazolinone derivatives, as an analog of ELF®97, are unable to achieve satisfactory result on live cells due to its irreversible nucleated crystallization (Wang et al., *Bioconjugate Chem.* 18:754-764 (2007), which is hereby incorporated by reference in its entirety) or significant cytotoxicity (Kim et al., *Chem. Commun.* 47:9825-9827 (2011), which is hereby incorporated by reference in its entirety).

These results, along with the results in preceding Examples, demonstrate that self-assembled nanofibrils allow phosphatase activity to be quantified using a plate reader, and that nanofibrils are readily reversible and cell compatible for periods of time. These results also illustrate the integration of enzyme catalysis and self-assembly of small molecules as a new approach to interrogate the expression level of ectophosphatases in the pericellular space of cells, thus providing a fundamentally new way for broadly and effectively evaluating phosphatase activity in the most prominent domain of tumor microenvironment (lida et al., *Science* 342:967-970 (2013), which is hereby incorporated by reference in its entirety). In addition, the versatility of this approach also offers additional advantages for developing a cell-based assay to screen agonists and antagonists of phosphatases.

Prospective Example 19

Establishing the Temporal Profiles of the Cancer Secretomes from Various Cancer Cell Lines Preceding Examples 8-15 establish the capability of nanonets/hydrogel to register the temporal profiles of cancer secretome of HeLa cells, and preceding Examples 16-18 confirm the ability of nanonets/hydrogel to form on various forms of cancer. The quantities (e.g., total protein amounts) and composition of the proteins (by LC-MS/MS analysis) in the secretome collected by the nanonets/hydrogel from the pericellular space of these cells will be examined to evaluate how the secretome and its corresponding temporal profiles correlate with the genetic mutation, molecular signature, and tissue type of the tumor cells. By establishing that the cancer secretome, collected by the nanonets/hydrogel, is able to reflect the differences of those tumor cells, this research will further advance the utility of nanonets/hydrogel of D-peptides for collecting the cancer cell secretome.

Since cancer is comprised of over 200 distinct disease lineages, it is impossible for cells of different tumors to have the same secretome. Therefore, nanonets/hydrogel, as a sampling method, should be able to collect secretome from different cancer cell lines for evaluating secreted proteins of different type of tumors. To establish the generality and scope of nanonets/hydrogel of D-peptides, nanonets/hydrogel collection will be employed to collect cancer secretomes from different cancer cell lines. Table 2 below lists the cell lines that will be used for the collection of cancer secretome.

TABLE 2

Tumor Cells for the Collection of Secretome

| Cell Line | ATCC # | Tissue | Mutation | Signature | Drug | Reference |
|---|---|---|---|---|---|---|
| Caov-3 | HTB75 | Ovary | | | paclitaxel | Gunawardana et al., *J Proteome Res* 8: 4705 (2009) |
| LNCap | CRL-1740 | Prostate | | | curcumin | Sardana et al., *J Proteome Res* 7: 3329 (2008) |
| PANC-1 | CRL-1469 | Pancreas | TP53 | | artesunate | Gronborg et al., *Mol Cell Proteomics* 5: 157 (2006) |
| A-549 | CCL-185 | Lung | RAS | EGFR | reticulol | Huang et al., *Lung Cancer* 54: 87 (2006) |
| MDA-MB-468 | HTB-132 | Breast | | FGFR | paclitaxel | Kulasingam et al., *Mol Cell Proteomics* 6: 1997 (2007) |
| HCT116 | CCL-247 | Colon | | | cisplatin | Kang et al., *J Agric Food Chem* 62: 2353 (2014) |

*Each of the listed references is hereby incorporated by reference in its entirety.

The cell lines in Table 2 are commercially available from the ATCC. These tumor cells are being chosen not only because they originate from different tissues, but also because their secretomes exist in the literature and are therefore readily available for referencing and comparison. Among these cell lines, PANC-1 has a well-documented TP53 mutation, A-549 has a definitive RAS mutation, MDA-MD-468 over-expresses EGFR, and HCT116 has the amplification of FGFR. These six tumor cell lines offer adequate diversity in terms of tissue type, genetic mutation, and molecular signature. The cancer secretome will be collected in the presence and absence of a proper anticancer drug for a specific tumor cell line. Thus, the comprehensive cell parameters provided by these tumor cell lines will allow the evaluation of the use of nanonets/hydrogel of D-peptides as a general approach to register temporal profiles of cancer secretome.

Figure 34:
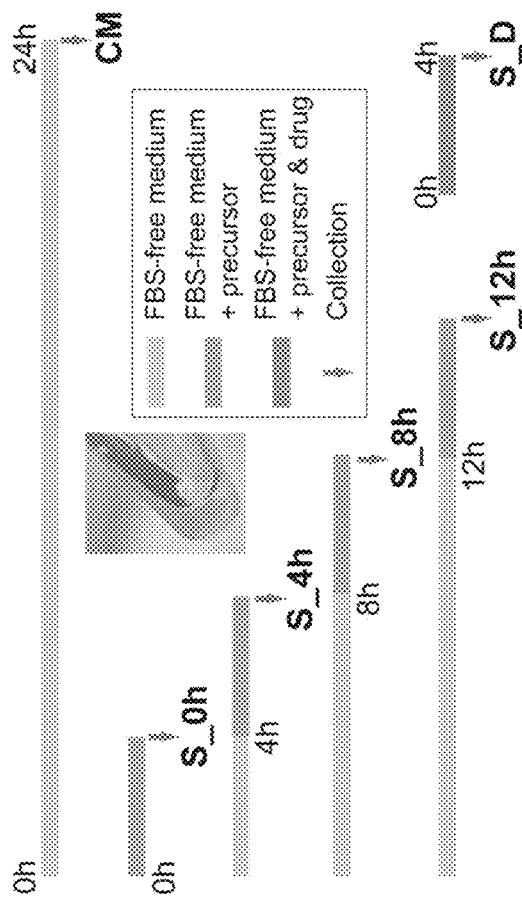
FIG. 34 shows the scheme for the collection of the cancer secretome of different tumor cells at different times or under different conditions. The illustration shows the use of nanonets/hydrogel to collect cancer secretome from the tumor cells exposed in FBS-free medium for different lengths of time or exposed to drug. As a control, CM will be collected from the corresponding tumor cells after incubated in FBS-free medium for 24 hours. Photo inset showing an example of the nanonets/hydrogel (containing cancer secretome) obtained according to the cold shock procedure in FIG. 19D.

Because the nanonets/hydrogel are able to collect more secretory proteins in 4 hours than CM does in 24 hours, as demonstrated in the preceding Example 4 hours will be used as the collection time of the nanonets/hydrogel. FIG. 34 illustrates the collection of nanonets/hydrogel from the tumor cells incubated in FBS-free medium for different lengths of time or treated by the proper drugs. As a control, CM will be collected from the tumor cells incubated in FBS-free medium for 24 hours. In general, the tumor cells will be seeded into a 35 mm Petri dish. Following 24 hour incubation in proper growth medium, the medium will be replaced with FBS-free MEM medium. For the collection of CM, the cells will be incubated with FBS-free MEM for 24 hours. For the collection of the secretome by the nanonets/hydrogel for registering the temporal profiles, cells will be incubated with FBS-free MEM medium for 0, 4, 8, or 12 hours prior to the addition of the nanonet precursors (e.g., D-2a, D-3a, or D-4a). After the additional 4 hour incubation in the presence of the nanonet precursors, the secretome will be collected in the nanonets/hydrogel. In the case of anti-cancer drug treatment, the drug will be added simultaneously with the nanonet precursors at 0 hours. The purpose of adding the drug at 0 hours is to minimize the effect of FBS-free MEM medium. Thus, the nanonets/hydrogel will be able to capture the secretome that reflects the presence of the drug. Following the 4 hour incubation in the presence of the nanonets/hydrogel and the drug, the nanonets/hydrogel will be collected using the procedures described in Example 8. The 4 hour incubation was also chosen to minimize autolysis induced by the drug.

After the collection of the secretory proteins in the nanonets/hydrogel, gel electrophoresis will be used to prepare proteomic samples. Generally, each sample will be mixed with Laemmli loading buffer. The solution will be mixed and incubated at 95° C. for 5 minutes. Then the solution will be used for SDS-PAGE. For protein mass analysis, the gel will be stained by Coomassie, and each lane will be cut into three sections with molecular weight ranges at: 250-80 kDa; 80-40 kDa; and 40-10 kDa. Protein bands will be pooled into three groups according to the ranges of molecular weights to allow sufficient resolution without the expense of efficiency and accuracy. (If sample resolution is insufficient, then gradient gels will instead be used (Kato et al., *Cell* 149:753 (2012), which is hereby incorporated by reference in its entirety).) After the sample preparation, the samples will be analyzed by LC-MS/MS (Aebersold and Goodlett, *Chem Rev* 101:269 (2001), which is hereby incorporated by reference in its entirety). The identification of protein will be conducted using the SEQUEST algorithm. The final report of the proteins will rule out all contaminants.

The temporal profile of cancer secretome will be constructed first by merging data lists from different time points. The whole list of confidently identified proteins will be categorized by the online gene classification system PANTHER (Mishra et al., *Neurobiol Aging* 34(4): 1310.e11-23 (2013), which is hereby incorporated by reference in its entirety). Data with missing information on the functional classification will not be input. All the output files with GO information will be combined to generate the categorized secretome profile. The matching records between the temporal and functional profiles based on the same protein UniProt ID will be conducted by using Febrl (Christen, *IEEE T Knowl Data En* 24:1537 (2012), which is hereby incorporated by reference in its entirety) and manually edited due to the fact that proteins can have more than one GO molecular function. The results of GO classification will be plotted in overview pie charts to show the functional composition of secretome at each time point. The sum of unique peptide number of every GO function will be displayed in line-dot-plot to depict the general changing trend of temporal secretion. The merged profile of cancer secretome will be structured according to information such as protein ID, unique peptide number, total peptide number at each time point, and GO molecular functions. The data, including an average peptide number of different time points, standard deviation, and relative change value throughout the time period, will be processed for statistical analysis to calculate the statistical trend. In this quantification process, the relative change value will be devised from the difference between unique peptide number and average peptide number. Based on the comparison of different time points (e.g., 0 h, 4 h, 8 h, and 12 h), the SD value will be used to select appropriate protein to present the categorized profiling instead of showing the non-changing trend of the majority. In each GO category, for selected proteins that have significantly large change over the time with SD value ≥3, GraphPad Prism 6 will be used to illustrate the trends associated with protein temporal profiles. Using the secretome of 0 hours and CM to reference the secretome of tumor cells treated by the anticancer drugs according to the design in Table 2, the ability of the nanonets/hydrogel for revealing the effects of the drugs on the secretomes of the tumor cells will be evaluated.

Due to the fact that the overexpression of phosphatases is a general feature of cancer cells (Pospisil et al., *BMC Bioinformatics* 7:11 (2006); Yang et al., *Chem Biol Drug Des* 78:923 (2011), each of which is hereby incorporated by reference in its entirety), the formation of pericellular nanonets/hydrogel on the chosen cancer cell lines is expected to allow the collection of the cancer secretomes. This study will confirm the breadth of nanonets/hydrogel of D-peptides as a fundamentally new sampling method for registering the dynamics (i.e., temporal profile) of the cancer secretome for discovering clinically meaningful cancer biomarkers. By comparing the amounts and the compositions of the proteins in the secretome collected by the nanonets/hydrogel from different tumor cells at different time points with the secretome collected by CM, the collection efficiency of the nanonets/hydrogel will be established to be superior to that of CM, and the advantages of the nanonets/hydrogel will be demonstrated. It is expected, based on the preceding Examples, that the nanonets/hydrogel will collect up to 5 fold more total proteins than that of CM. The comparison of the amounts and compositions of the proteins with the cancer secretome of these tumor cells documented in literature will further confirm the advantages of the nanonets/hydrogel approach. By comparing the secretome of the cells in response to the treatment of anticancer drugs, it is expected to be able to obtain the magnitude of the changes in the secretome, thus validating the nanonets/hydrogel as a general approach for collecting cancer secretome that will serve as a mean of prognosis of cancer.

Prospective Example 20

Nanonets/Hydrogel Collect Cancer Secretome in the Tumor Microenvironment

Figure 36:
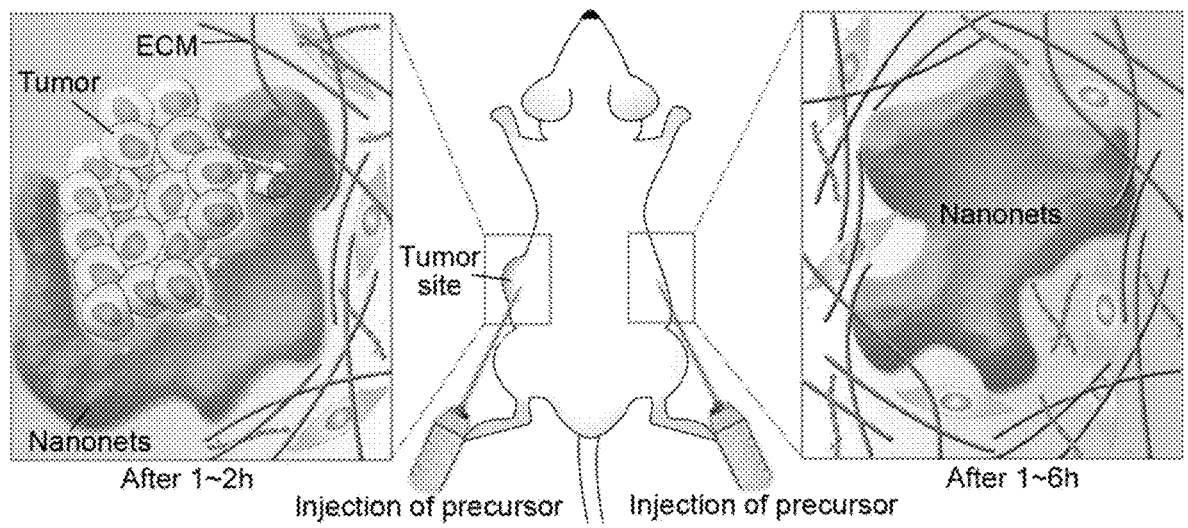
FIG. 36 shows the use of nanonets/hydrogel to collect secretome of ovarian cancer in vivo. It shows injection of precursor in mice to afford nanonets/hydrogel around the ovarian tumor to sequestrate secretome and collect the control at the normal ovarian site.

The advancement of cancer biology in the past decade has revealed the great complexity of cancer (Hanahan and Weinberg, *Cell* 144:646 (2011), which is hereby incorporated by reference in its entirety). Many factors contribute to secretome alterations in cancer, which impacts the tumor microenvironment that reciprocally plays a deterministic role in cancer progression (Paltridge et al., *BBA-Proteins Proteomics* 1834:2233 (2013), which is hereby incorporated by reference in its entirety). Therefore, the direct collection of the cancer cell secretome from the tumor microenvironment becomes an unavoidable starting point for interrogating the functional constituents in tumor microenvironment, which is becoming necessary and fundamental knowledge for understanding cancer biology and prognosis. Because nanonet precursors made of small D-peptides can easily diffuse into the interstitial spaces present within the tumor microenvironment to form nanonets/hydrogel, the pericellular nanonets/hydrogel of D-peptides, offer a unique opportunity for the collection of the cancer secretome from the tumor microenvironment. FIG. 36 shows the general design for the use of the nanonets/hydrogel of D-peptides to collect the cancer secretome from the co-culture of cancer and stromal cells that mimic tumor microenvironment (Straussman et al., *Nature* 487:500 (2012), which is hereby incorporated by reference in its entirety). Because the growth factors for tumor proliferation are regulated in the pericellular space (Hanahan and Weinberg, *Cell* 144:646 (2011), which is hereby incorporated by reference in its entirety), the collection of the cancer secretome from the pericellular space of cancer cells in the presence of the stromal cells will help establish a sampling method for understanding the identities and sources of the proliferative signals from normal tissues and the corresponding controlling mechanisms.

Figure 35:
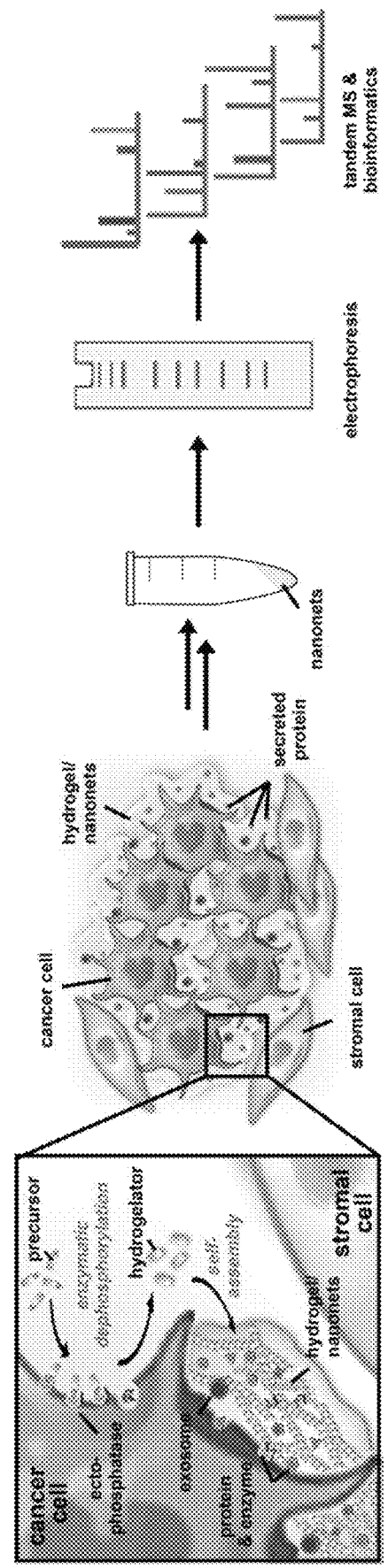
FIG. 35 shows the selective formation of pericellular nanonets/hydrogel on cancer cells in tumor microenvironment. It is an illustration of the formation of pericellular nanonets/hydrogel, via phosphatases catalyzed self-assembly of hydrogelators, for the selective collection of cancer secretome in tumor microenvironment containing cancer and stromal cells.

Examples 8-15 confirm the advantage of using nanonets/hydrogel to collect cancer secretome from the pericellular space of the cancer cells in the presence of environmental stimuli from other cells. In the case of co-culture of HeLa cells and HS-5 cells, the nanonets/hydrogel formed on the surface of the cancer cells, but not on the surface of stromal cells (FIG. 17C). These results confirm that the process shown in FIG. 35 is feasible, thus the nanonets/hydrogel will be able to collect cancer secretome from the pericellular space of tumor cells in tumor microenvironment.

These studies are designed to further advance the use of nanonets/hydrogel of D-peptides as a new sampling method for collecting the cancer secretome from the tumor microenvironment. Since the nanonets/hydrogel form gradually due to enzymatic transformation, they will have minimal impact on the communication of the cancer cells and the stromal cells in the co-culture. This feature is uniquely advantageous for understanding the proliferative signals in tumor microenvironment. The quantities and composition of the proteins in the secretome collected by the nanonets/hydrogel from the pericellular space of the cancer cells in the co-culture that mimics tumor microenvironment will be examined. How the secretome and its corresponding temporal profiles correlate with the type of the nurture cells will be evaluated. By evaluating the ability of nanonets/hydrogel to collect cancer secretomes from the co-culture of cancer cells with different nurture cells (e.g., stromal or cancer associated fibroblast ("CAF") cells), this research will further advance the capability of nanonets/hydrogel of D-peptides for collecting cancer secretome.

To validate that nanonets/hydrogel of D-peptides are able to collect cancer secretome in the tumor microenvironment, the ability of the nanonets/hydrogel to collect and to differentiate the secretomes from different co-cultures as the mimics of tumor microenvironment will be examined. Specifically, the co-culture of cancer cells (HeLa) and stromal cells (e.g., HS-5) in one case (Straussman et al., *Nature* 487:500 (2012), which is hereby incorporated by reference in its entirety), and the co-culture cancer cells (HeLa) with cancer-associated fibroblast cells (L929) in another case will be used (Gao et al., *Biomaterials* 35:2181 (2014), which is hereby incorporated by reference in its entirety). The same cancer cell line (HeLa) but different types of nurture cells for the co-culture will be used to allow the comparison of cancer secretomes with the data in the literature and evaluate the versatility of nanonets/hydrogel for different tumor microenvironment.

To confirm that nanonets/hydrogel of D-peptides are able to register the temporal profile of cancer secretome in the tumor microenvironment, the nanonets/hydrogel will be used to collect cancer secretomes from the co-culture of cancer and stromal cells at different time points in 4 h interval from 4-24 hours. Specifically, nanonet precursors will be added to the co-cultures at 4, 8, 12, 16, and 20 hours after the starting of co-culture, and collect the secretome at 8, 12, 16, 20, and 24 hours, respectively.

After the collection of the secretory proteins in the nanonets/hydrogel, gel electrophoresis will be used to prepare proteomic samples, followed by LC-MS/MS as described in Prospective Example 19.

The temporal profile of the cancer sercretome will be constructed from the co-cultures using the similar analysis process outlined above. The protein profiles of HeLa cells collected by CM and the secretome of HeLa cells in the literature (Wu et al., *Mol Cell Proteomics* 9:1100 (2010), which is hereby incorporated by reference in its entirety) will be used as the control and the reference. By examining the temporal profiles of cancer secretome from the co-cultures, we will establish the ability of pericellular nanonets/hydrogel for capturing the intercellular signaling processes between cancer and stromal cells, an important aspect of cancer biology. Secretory proteins from pericellular space of cancer cells will be correlated with the type of the nurture cells (e.g., HS-5 or L929). By profiling the proteins in the pericellular hydrogels of the cancer cells obtained at different time (e.g., different stages of signaling process), the ability of nanonets/hydrogel to reveal how the change of microenvironment affects the enzymes/proteins secretion of cancer cells will be evaluated. Overall, this study will establish pericellular nanonets/hydrogel as a paradigm-shift method to register the dynamic and complexity of cancer secretome in tumor microenvironment.

Prospective Example 21

Nanonets/Hydrogel Collect Cancer Secretome at Lesion Proximal Sites In Vivo

Because it is estimated that disease biomarkers in local tumor microenvironment is ~1000-1500 times higher than that in blood (Ahn et al., *Proteom Clin Appl* 1:1004 (2007), which is hereby incorporated by reference in its entirety), a minimally invasive sampling method to collect cancer secretome at the lesion-proximal sites would have the most significant clinical impact. The selective formation of pericellular nanonets/hydrogel promises such a minimal invasive sampling method that has high protein recovery, reduces pre-analytical variations, and registers the dynamics of cancer secretome at the lesion-proximal site. FIG. 36 shows the general design for using the nanonets/hydrogel of D-peptides to collect cancer secretome from the lesion-proximal sites of ovarian cancer mouse models (see Vanderhyden et al., *Reprod Biol Endocrinol* 1:67 (2003); Dinulescu et al., *Nat Med* 11:63 (2005), each of which is hereby incorporated by reference in its entirety). Ovarian tumor was chosen because the anatomy of ovary and peritoneal cavity allows relatively precise localization of the nanonets/hydrogel. To distinguish the nanonets/hydrogel from tissues and to facilitate the collection of the secretome, fluorescent nanonets/hydrogel will be used. Moreover, because the nanonets/hydrogel can flow under shearing, it is easy to use simple suction to collect the fluorescent nanonets/hydrogel after their formation. Nanonet precursors (e.g., D-3a or D-4a) will also be injected into the peritoneum and ovary of normal mice to form nanonets/hydrogel, then those nanonets/hydrogel will be collected as the control.

Figure 37:
FIG. 37 shows subcutaneous formation of nanonets/hydrogel. The optical image is of the hydrogel formed subcutaneously one hour after injecting the precursors into the mice.

To use the nanonets/hydrogel for collecting cancer secretome from the lesion-proximal site, one prerequisite is enzymatic formation of the nanonets/hydrogel in vivo. A previous study has confirmed that the subcutaneous injection of the solution of a precursor of a hydrogelator in mice results in the formation of the nanonets/hydrogel in vivo after 1-6 hr of injection (Yang et al., *Small* 3:558 (2007); Yang et al., *J Am Chem Soc* 128:3038 (2006), each of which is hereby incorporated by reference in its entirety). See also FIG. 37. These results indicate that, for the collection of cancer secretome in vivo, it is feasible to form nanonets/hydrogel selectively on cancer cells at the lesion-proximal sites by designing appropriate small D-peptide-based precursors of nanonets/hydrogel.

Figures 38A, 38B:
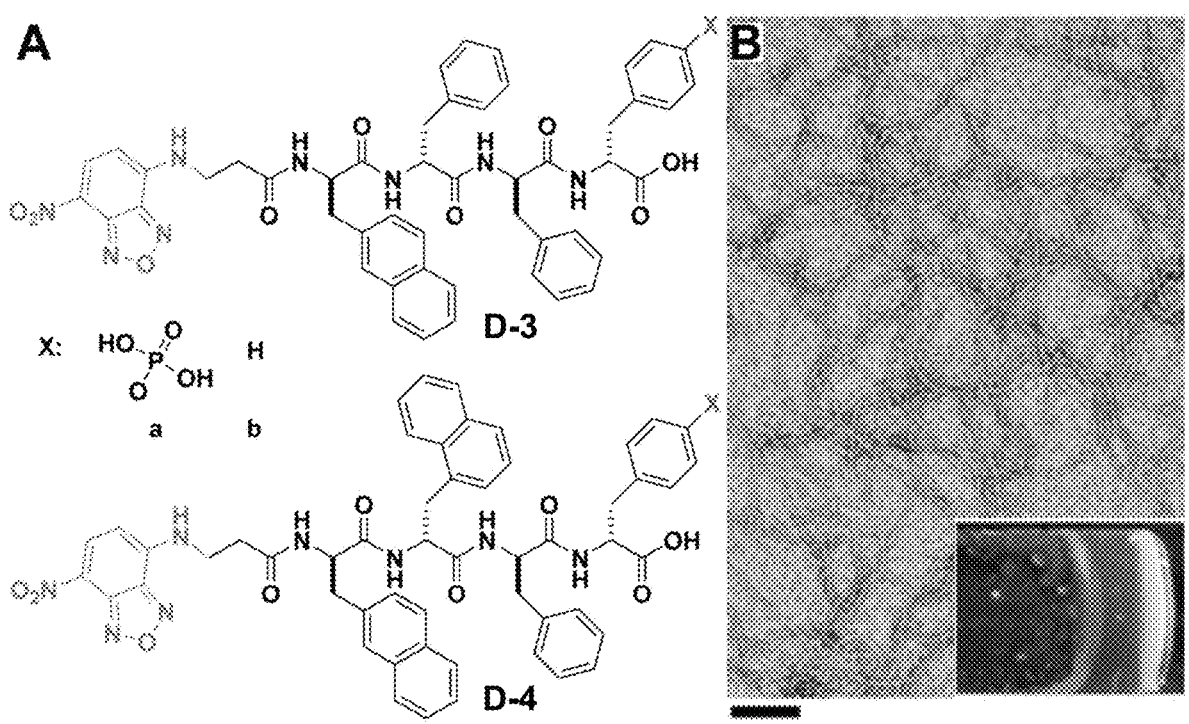
FIGS. 38A-38B show phosphatase-catalyzed self-assembly to form fluorescent nanonets/hydrogel.

The complexity in the animal models obviously will make the lesion-proximal sites in vivo a more challenging environment than cell culture in vitro. One major issue is how to locate the nanonets/hydrogel from the background of other tissues and organs. To address this issue, NBD-fluorescent nanonets/hydrogel will be used. Applicants have previously developed a hydrogelator that fluoresces only when forming nanonets (Gao et al., *Nat Commun* 3:1033 (2012), which is hereby incorporated by reference in its entirety). Based on that result, the hydrogelator precursor molecule D-3a was designed and synthesized as an analog of D-2a. As shown in FIGS. 38A-38B, phosphatases can catalyze the dephosphorylation of D-3a to form D-3b, which self-assembles to form the fluorescent nanonets/hydrogel. Also shown are precursor molecule D-4a and its corresponding hydrogelator D-4b, which differ from D-3a/D-3b by the replacement of a phenylalanine residue with a napthylalanine residue at the second position. The preceding Examples demonstrate that, for the collection of cancer secretome in vivo, it is feasible to form fluorescent nanonets/hydrogel selectively on cancer cells to facilitate the collection of secretome at the lesion-proximal sites despite the background colors of tissues and organs.

The resistance to adjuvant chemotherapy remains a major obstacle in treating ovarian cancers because of the lack of early detection of ovarian cancer and the almost inevitable relapse in the patients with advanced ovarian cancer (American Cancer Society, Cancer Facts & Figures 2013, Atlanta: American Cancer Society (2013); Yap et al., *Nat Rev Cancer* 9:167 (2009), each of which is hereby incorporated by reference in its entirety). Therefore, the validation of the use of nanonets/hydrogel to collect cancer secretome on the lesion-proximal sites of ovarian cancer animal model will be a significant contribution to the research of ovarian cancer and clinical care. Using a previously developed genetic mouse model of de novo high-grade serous carcinoma (HGSC) that presents tumors in fallopian tube, ovary, and peritoneum provides an ideal platform for testing the capability of the nanonets/hydrogel as a sampling method that collects cancer secretome at lesion-proximal sites in vivo (see Perets et al., *Cancer Cell* 24:751 (2013), which is hereby incorporated by reference in its entirety).

According to the lesion sites of tumor in the HGSC mouse model, pericellular nanonets/hydrogel will be used to collect cancer secretomes from tumors at three types of sites: fallopian tube, ovary, and peritoneum. Specifically, precursors will be injected at those three tumor sites and suction will be used to collect the fluorescent nanonets/hydrogel via shear flow. Collection will be carried out at two different time points (e.g., 6 hours and 12 hours). After collection, low-speed centrifugation will be used to separate the nanonets/hydrogel from the extracellular fluids, similar to the procedure shown in FIG. 19D.

As a control, the secretome of normal tissues will also be collected by forming the nanonets/hydrogel at peritoneum and ovary of normal mice, but with prolonged in vivo reaction time or with the addition of exogenous alkaline phosphatases, if necessary. The normal secretome will also be collected in peritoneum of mice at 6 hours and 12 hours.

After the collection of the secretory proteins in the nanonets/hydrogel, gel electrophoresis will be used to prepare proteomic samples and the samples will be analyzed by LC-MS/MS as described in Prospective Example 19. By comparing the protein compositions obtained from different mice, the reproducibility will be estimated, with an expected correlation of $(R^2)>0.72$ as a milestone of success.

The dynamics of cellular environment in vivo obviously is a more demanding situation than cell culture. One possible issue may be that the rheological stability of the nanonets/hydrogel of D-3b is insufficient in vivo. If this problem arises, precursors/hydrogelators will be optimized for in vivo application. To increase the rheological stability of the nanonets/hydrogel in vivo, an additional naphthylalanine ("Nal") will be used in the form of D-4a/D-4b (FIG. 38A), because it has already been confirmed that Nal enhances the ability of self-assembly (Wu et al., Chem Commun 50(16): 1992-4 (2014), which is hereby incorporated by reference in its entirety). If metabolism and circulation in vivo leads to undesirable diffusion, then the concentration of the precursors will be increased to ensure fast formation of nanonets/hydrogel at the lesion-proximal sites.

Discussion of Examples 19-21

Directly collecting cancer secretome from pericellular space in accordance with the present invention promises a fundamentally new sampling method for exploring cancer secretome. The present invention affords rapid sampling technology for maximizing the quality and utility of secreted proteins or signaling substances of cancer cells for cancer research and/or clinical care. Specifically, coupling the generic difference, e.g., overexpression of phosphatases, between cancer and normal cells with the collecting process, i.e., pericellular nanonets/hydrogel, significantly increases the amounts of the proteins collected, reduces pre-analytical variations, and reveals the spatiotemporal profiles of cancer secretomes.

While conducting research on enzyme-catalyzed formation of supramolecular nanofibrils, applicants unexpectedly observed the selective formation of nanonets/hydrogel of a small D-peptide in pericellular space of cancer cells due to the overexpressed phosphatases on the cancer cells (see Examples 1-6). Because D-peptides resist proteases, the nanonets/hydrogels of the D-peptides are relatively stable in vivo when collecting the secretome. Moreover, Examples 8-15 confirm that the pericellular nanonets/hydrogel, within 2-4 hours, not only collect more of total secretory proteins from HeLa cells than the conditioned media (e.g., the media cultured with cancer cells for 24 hours) do, but also reduce pre-analytical variations and register temporal profile of the secretome. Thus, the use of pericellular nanonets/hydrogel of D-peptide is a powerful technique for collecting cancer secretomes. There exists a need for a general sampling method for rapid and selective collection of cancer secretomes from tumor microenvironment or lesion-proximal sites. Moreover, the collection process is compatible with current pre-analytic approaches, e.g., microfluidics (Duffy et al., *Anal Chem* 70:4974 (1998); Easley et al., *Proc Natl Acad Sci USA* 103:19272 (2006); Miller et al., *Proc Natl Acad Sci USA* 109:378 (2012); Link et al., *Phys Rev Lett* 92:4 (2004); Schneider et al., *Anal Chem* 85:10417 (2013); Fiorini et al., *Biotechniques* 38:429 (2005), each of which is hereby incorporated by reference in its entirety), and SILAC (Ong et al., *Mol Cell Proteomics* 1:376 (2002), which is hereby incorporated by reference in its entirety), and analytic technologies, e.g., gel electrophoresis, microarray (Albert et al., *Chem Rev* 100:2595 (2000); Michael et al., *Anal Biochem* 273:168 (1999); Walt et al., *Abstr Pap Am Chem Soc* 246:1 (2013), each of which is hereby incorporated by reference in its entirety), and LC-MS/MS, which are commonly used in the quantitative proteomic analysis.

The present invention will provide innovative approaches for discovering new insights and establishing new paradigms of cancer secretome. The knowledge obtained concerning secretory signaling substances (e.g., proteins, exosomes, and miRNAs) in vitro and in vivo, will ultimately bring new understanding to cancer biology and clinical care. Moreover, accurate mapping of the dynamic cancer secretome will contribute to the discovery of cancer biomarkers for early detection of cancers, thus reducing mortality caused by cancers (Yap et al., *Nat Rev Cancer* 9:167 (2009), which is hereby incorporated by reference in its entirety).

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed:

1. A method for forming a pericellular nanofibril network on or near the surface of a target cell, the method comprising:

contacting a target cell that expresses a cell surface-bound enzyme having hydrolytic activity, secretes an enzyme having hydrolytic activity, or both, with one or more peptides each being three to five D-amino acids in length, including a plurality of aromatic D-amino acid residues and a carboxy-terminal D-amino acid residue that is phosphorylated, wherein the one or more peptides do not contain lysine residues and do not comprise a nucleobase capping moiety; wherein the target cell is a cancer cell; and wherein said contacting is effective to hydrolyze the phosphate group and cause self-assembly of the dephosphorylated one or more peptides to form a pericellular nanofibril network on or near the surface of the target cell.

2. The method according to claim 1, wherein said contacting is effective to inhibit cancer cell migration, inhibit cancer cell survival, inhibit cancer cell growth, and/or inhibit passage of intracellular signaling molecules to or from the pericellular nanofibril network-covered cancer cell.

3. The method according to claim 1, wherein the one or more peptides are selected from the group consisting of:

NapAc-(D-Phe)-(D-Phe)-(D-Tyr(phospho));

NBD-Prop-(D-Nal)-(D-Phe)-(D-Phe)-(D-Tyr(phospho)); and

NBD-Prop-(D-Nal)-(D-Nal)-(D-Phe)-(D-Tyr(phospho));

where NapAc is a 2-naphthalenyl-acetyl group and NBD-Prop is a (7-nitro-1,2,5-benzoxadiazolyl amino)proprionyl group.

4. The method according to claim 1, wherein each of the plurality of aromatic D-amino acid residues is selected from D-tyrosine (Tyr), D-phosphotyrosine (Tyr(phospho)), D-phenylalanine (Phe), and D-naphthylalanine (Nal).

5. The method according to claim 1, wherein the one or more peptides comprise a capping moiety selected from the group consisting of 2-naphthalenyl-acetyl group and (7-nitro-1,2,5-benzoxadiazolyl amino)proprionyl group.

6. The method according to claim 1, wherein the one or more peptides comprise the structure of CAP-$X_1$-$X_2$-$X_3$-DTyr(phospho), wherein CAP is

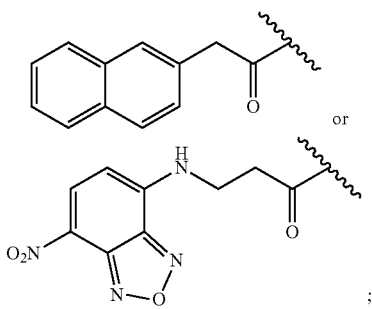

$X_1$ is a $_D$Nal or $_D$Phe residue;
$X_2$ is a $_D$Nal or $_D$Phe residue; and
$X_3$ is a direct link between $X_2$ and the $_D$Tyr(phospho) residue, or a $_D$Nal or $_D$Phe residue.

7. The method according to claim 1, wherein the one or more peptides are present at a concentration of at least about 280 μM up to about 1 mM.

8. A method for collecting a target cell secretome comprising:
   forming a pericellular nanofibril network on or near the surface of a target cell according to claim 1, whereby the pericellular nanofibril network retains the target cell secretome from the pericellular space of the target cell;
   separating the target cell secretome from the pericellular nanofibril network; and
   collecting the separated target cell secretome.

9. The method according to claim 8, further comprising raising antibodies against the target cell secretome, wherein the antibodies recognize the target cell.

10. The method according to claim 8, wherein the one or more peptides are selected from the group consisting of:
    NapAc-(D-Phe)-(D-Phe)-(D-Tyr(phospho));
    NBD-Prop-(D-Nal)-(D-Phe)-(D-Phe)-(D-Tyr(phospho)); and
    NBD-Prop-(D-Nal)-(D-Nal)-(D-Phe)-(D-Tyr(phospho));
    where NapAc is a 2-naphthalenyl-acetyl group and NBD-Prop is a (7-nitro-1,2,5-benzoxadiazolyl amino)proprionyl group.

11. A screening method for a target cell secretome comprising:
    collecting a target cell secretome according to claim 8; and
    analyzing the target cell secretome.

12. The method according to claim 11, wherein the screening method is carried out in parallel over a period of time, and said analyzing is effective to register a temporal profile of the target cell secretome.

13. A method of in vivo imaging, the method comprising:
    forming a pericellular nanofibril network on or near the surface of a target cell according to claim 1, wherein the one or more peptides include a fluorophore or contrasting agent; and
    imaging the pericellular nanofibril network.

* * * * *